(12) United States Patent
McAlpine et al.

(10) Patent No.: US 7,655,646 B2
(45) Date of Patent: *Feb. 2, 2010

(54) DIBENZODIAZEPINONE ANALOGUES, PROCESSES FOR THEIR PRODUCTION AND THEIR USE AS PHARMACEUTICALS

(75) Inventors: James B. McAlpine, Montreal (CA); Arjun H. Banskota, St. Laurent (CA); Mustapha Aouidate, St. Laurent (CA)

(73) Assignee: Thallion Pharmaceuticals, Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/962,855

(22) Filed: Dec. 21, 2007

(65) Prior Publication Data

US 2008/0161291 A1  Jul. 3, 2008

Related U.S. Application Data

(63) Continuation-in-part of application No. 11/253,658, filed on Oct. 20, 2005, now abandoned, which is a continuation-in-part of application No. 11/235,398, filed on Sep. 27, 2005, now Pat. No. 7,304,054, which is a continuation-in-part of application No. 10/762,107, filed on Jan. 21, 2004, now Pat. No. 7,101,872, said application No. 11/235,398 is a continuation-in-part of application No. 10/951,436, filed on Sep. 27, 2004, now Pat. No. 7,186,713, said application No. 10/951,436.

(60) Provisional application No. 60/492,997, filed on Aug. 7, 2003, provisional application No. 60/518,286, filed on Nov. 10, 2003, provisional application No. 60/625,653, filed on Nov. 8, 2004, provisional application No. 60/647,381, filed on Jan. 28, 2005, provisional application No. 60/701,472, filed on Jul. 22, 2005.

(30) Foreign Application Priority Data

Feb. 11, 2005  (CA) .................................... 2497031

(51) Int. Cl.
*C07D 243/10* (2006.01)
*A61K 31/55* (2006.01)

(52) U.S. Cl. ...................... 514/220; 540/495
(58) Field of Classification Search ................. 540/495; 514/220

See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 5,039,660 A | 8/1991 | Leonard | |
| 5,393,665 A | 2/1995 | Fayerman et al. | |
| 5,466,590 A | 11/1995 | Sariaslani et al. | |
| 5,523,288 A | 6/1996 | Cohen et al. | |
| 5,541,181 A | 7/1996 | Ohkuma | |
| 5,556,772 A | 9/1996 | Sorge et al. | |
| 5,561,122 A | 10/1996 | Pettit | |
| 5,783,561 A | 7/1998 | Horwitz et al. | |
| 5,830,695 A | 11/1998 | Serizawa et al. | |
| 6,140,306 A | 10/2000 | Lambert, Jr. et al. | |
| 6,423,753 B1 | 7/2002 | Dougherty | |
| 6,683,300 B2 | 1/2004 | Doroshenko | |
| 7,257,562 B2 | 8/2007 | Farnet et al. | |
| 2003/0109518 A1 | 6/2003 | Lu et al. | |
| 2003/0219718 A1 | 11/2003 | Weber et al. | |
| 2004/0220179 A1 | 11/2004 | Lu et al. | |

FOREIGN PATENT DOCUMENTS

CA          2248820          9/1997

OTHER PUBLICATIONS

Goodfellow, "*Superageneric Classification of Actinomycetes*," Bergey's Manual of Systematic Bacteriology (1989), vol. 4, pp. 2333-2339.
Embley and Stackebrandt, "*The Molecular Phylogeny and Systematics of the Actinomycetes*," Annu. Rev. Microbiol., (1994), vol. 48, pp. 257-289.
Zazopoulos et al., "*A Genomics-Guided Approach for Discovering and Expressing Cryptic Metabolic Pathways*," Nature Biotechnology (2003), vol. 21, pp. 187-190.
Stryer, Biochemistry 3rd Edition, 1998, W. H. Freeman and Co., New York, pp. 752-754.
Altschul et al., "*Basic Local Alignment Search Tool*," Journal of Molecular Biology (1990), vol. 215(3), pp. 403-410.
British Journal of Cancer, 1998, vol. 77(1), pp. 1-11, United Kingdom Coordinating Committee on Cancer Research (UKCCCR) Guidelines for the Welfare of Animals in Experimental Neoplasia (Second Edition).
Yasuhiro Igarashi et al., Revision of the Structure Assigned to the Antibiotic BU-4664L from Micromonopora, J. Antibiot., 2005, vol. 58(5), pp. 350-352.
Correction to Article by Yasuhiro Igarashi et al., Revision of the Structure Assigned to the Antibiotic BU-4664L from Micromonopora, J. Antibiot., 2005, vol. 58(7).
Demain et al., "*Manual of Industrial Microbiology and Biotechnology*," American Society for Microbiology, Washington DC, 1986.
Hesketh et al., "*A Novel Method for Improving Streptomyces coelicolor A3(2) for Production of rpsL (Encoding Ribosomal Protein S12) Mutations conferring Resistance of Streptomycin*," J. Antibiotics, 1997, vol. 50(6), pp. 532-535.
Hosoya et al., "*Acquisition of Certain Streptomycin-resistant (str) Mutations Enhances Antibiotic Production in Bacteria*," Antimicrobial Agents and Chrmotherapy, 1998, vol. 42(8), pp. 2041-2047.

(Continued)

*Primary Examiner*—Bruck Kifle

(57) ABSTRACT

The invention relates to biologically active dibenzodiazepinone analogs represented by Formula I, to methods of producing them, to pharmaceutical compositions comprising them and to methods of treating neoplastic conditions.

12 Claims, 7 Drawing Sheets

OTHER PUBLICATIONS

Plater et al., "*Synthesis of 1,3,5-tris[4-(dairylamino)phenyl] benzene and 1,3,5-tris(diarylamino)benzene derivative*," J. Chem. Society, Perkin Trans. 1, 2000, pp. 2695-2701.

Hwang et al., "*Efficient Synthesis of Phosphorylated Prodrugs with Bis(P0M)-phosphoryl Chloride*," Org. Lett, 2004, vol. 6(10), pp. 1555-1556.

Freireich et al., "*Quantitative Comparison of Toxicity of Anticancer Agents in Mouse, Rat, Hamster, Dog, Monkey and Man*," Cancer Chemoth., 1966, vol. 50(4), pp. 219-244.

Workman et al., "*Guidelines for the welfare of animals in experimental neoplasia*," United Kingdom Coordinating Committee on Cancer Research (UKCCCR), British Journal of Cancer, 1977, $2^{nd}$ Edition, vol. 77, pp. 1-10.

Premont et al., "*[3H] Norepinephrine Binding by rat glial cells in culture. Lack of correlation between binding and adenylate cyclase activation*," Biochim Biophys. Acta., 1975, vol. 381, pp. 368-376.

March et al., Advanced Organic Chemistry, John Wiley and Sons, Inc. pp. 404, (1991).

Silverberg et al., "*A simple, rapid and efficient protocol for the selective phosphorylation of phenols with dibenzyl phosphate*," Tetrahedron Letters, 1996, vol. 37, pp. 771-774.

Charan et al., "*A new antimicrobial alkaloid from a micromonospora sp.*," Abstract and figures from Poster P:157, presentation of the $44^{th}$ Annual Meeting of the American Society of Pharmacognosy, Chapel Hill, NC, 2003, pp. 209.

Takagi et al., "*A gene cluster for the mevalonate pathway from Streptomyces sp. Strain CL190*," Journal of Bacteriology, 2000, vol. 182(15), pp. 4153-4157.

Carrillo et al., "*The multiple sequence alignment problem in biology*," Applied Math, 1998, vol. 48(5), pp. 1073-1082.

Murakami et al., "*Thiostrepton-induced gene expression in Streptomyces Lividans*," Journal of Bacteriology, 1989, vol. 171(3), pp. 1459-1466.

Thompson et al., "*Cloning of antibiotic resistance and nutritional genes in Streptomycetes*," Journal of Bacteriology, 1982, vol. 151(2), pp. 668-677.

Hopwood et al., "*Plasmid and phage vectors for gene cloning and analysis in Streptomycetes*," Methods in Enzymology, 1987, vol. 153, pp. 116-166.

Nielson et al., "*Taq extender PCR additive for improved length, yield, and reliability of PCR products*," Strategies, 1994, vol. 7, pp. 27.

Matteucci et al., "*Synthesis of deoxyoligonucleotides on a polymer support*," American Chemical Society, 1981, vol. 130(11), pp. 3185-3191.

Gluzman et al., "*SV40-transformed simian cells support the replication of early SV40 mutants*," Cell, 1981, vol. 23(1), pp. 175-182.

Vaara, "*Agents that increase the permeability of the outer membrane*," Microbiological Reviews, 1992, vol. 56(3), pp. 395-411.

Tsubery et al., "*Structure-function studies of polymyxin B nonapeptide: Implications to sensitization of gram-negative bacteria*," Journal of Medical Chemistry, 2000, vol. 43(16), pp. 3085-3092.

Carter et al., "*5-Lipoxygenase inhibitory activity of zileuton*," Journal of Pharmacology and Experimental Therapeutics, 1991, vol. 256(3), pp. 929-937.

Safayhi et al., "*Concentration-dependent potentiating and inhibitory effects of boswellia extracts on 5-Lipoxygenase product formation in stimulated PMNL*," Planta Medica, 2000, vol. 66(2), pp. 110-113.

Dimitradou et al., "*Identification and characterization of a new cytotoxic agent from actinomycetes*," Poster Presentation Presented at the AACR Annual Meeting, Orlando, FL, Mar. 27 to 31, 2004.

Charan et al., "*Diazepinomicin, a new antimicrobial alkaloid from a marine Micromonospora sp.*," J. Nat. Prod., 2004, vol. 67(8), pp. 1431-1433.

Berge et al., "*Pharmaceuticals salts*," Journal of Pharmaccutical Scicnccs, 1977, vol. 66(1), pp. 1-19.

Rooseboom et al., "*Enzymed-catalyzed activation of Anticancer prodrugs*," Pharmacol. Rev., 2004, vol. 56, pp. 53-102.

Saline

Compound 1
(20 mg/kg)

DIBENZODIAZEPINONE ANALOGUES, PROCESSES FOR THEIR PRODUCTION AND THEIR USE AS PHARMACEUTICALS

RELATED APPLICATIONS

This application is a continuation-in-part of U.S. application Ser. No. 11/253,658, filed Oct. 20, 2005, which is a continuation-in-part of U.S. application Ser. No. 11/235,398, filed Sep. 27, 2005, now U.S. Pat. No. 7,304,054, which is a continuation-in-part of U.S. application Ser. No. 10/762,107, filed Jan. 21, 2004, now U.S. Pat. No. 7,101,872. U.S. Ser. No. 10/762,107 claims priority to U.S. Provisional Application 60/441,126, filed Jan. 21, 2003; U.S. Provisional Application 60/492,997, filed Aug. 7, 2003; and U.S. Provisional Application 60/518,286, filed Nov. 10, 2003. U.S. application Ser. No. 11/235,398 claims priority as a continuation-in-part of U.S. application Ser. No. 10/951,436, filed Sep. 27, 2004, now U.S. Pat. No. 7,186,713; U.S. Provisional Application 60/625,653, filed Nov. 8, 2004; U.S. Provisional Application 60/647,381, filed Jan. 28, 2005; U.S. Provisional Application 60/701,472, filed Jul. 22, 2005; and Canadian Patent Application 2,497,031, filed Feb. 11, 2005. The entire teachings of the above applications are incorporated herein by reference.

FIELD OF THE INVENTION

This invention relates to dibenzodiazepinone analogues, represented as derivatives of the naturally produced farnesylated dibenzodiazepinone referred to as Compound 1, and their pharmaceutically acceptable salts, solvates and prodrugs, and to methods for obtaining the compounds. One method of obtaining the derivatives involves post-biosynthesis chemical modification of Compound 1. The present invention further relates to the use of dibenzodiazepinone analogues, and their pharmaceutically acceptable salts, solvates and prodrugs as pharmaceuticals, in particular to their use as inhibitors of cancer cell growth, mammalian lipoxygenase, and for treating acute and chronic inflammation, and to pharmaceutical compositions comprising a dibenzodiazepinone analogue, or a pharmaceutically acceptable salt, solvate or prodrug thereof.

BACKGROUND OF THE INVENTION

The euactinomycetes are a subset of a large and complex group of Gram-positive bacteria known as actinomycetes. Over the past few decades these organisms, which are abundant in soil, have generated significant commercial and scientific interest as a result of the large number of therapeutically useful compounds, particularly antibiotics, produced as secondary metabolites. The intensive search for strains able to produce new antibiotics has led to the identification of hundreds of new species.

Many of the euactinomycetes, particularly *Streptomyces* and the closely related *Saccharopolyspora* genera, have been extensively studied. Both of these genera produce a notable diversity of biologically active metabolites. Because of the commercial significance of these compounds, much is known about the genetics and physiology of these organisms. Another representative genus of euactinomycetes, *Micromonospora*, has also generated commercial interest. For example, U.S. Pat. No. 5,541,181 (Ohkuma et al.) discloses a dibenzodiazepinone compound, specifically 5-farnesyl-4,7,9-trihydroxy-dibenzodiazepin-11-one (named "BU-4664L"), produced by a known euactinomycetes strain, *Micromonospora* sp. M990-6 (ATCC 55378). ECO-4601 (Compound 1) and *Micromonospora* sp. strains 046-ECO11 and [S01]046 are disclosed in U.S. Ser. No. 10/762,107, incorporated by reference in its entirety. ECO-4601 was also disclosed in Charan et al. (2004), *J. Nat. Prod.*, vol 67, 1431-1433, and Igarashi et al. (2005), *J. Antibiot.*, vol 58, no 5, 350-352. Its use for the treatment of cancer is disclosed in U.S. Ser. No. 10/951,436 and 11/130,295, both incorporated herein by reference in their entirety.

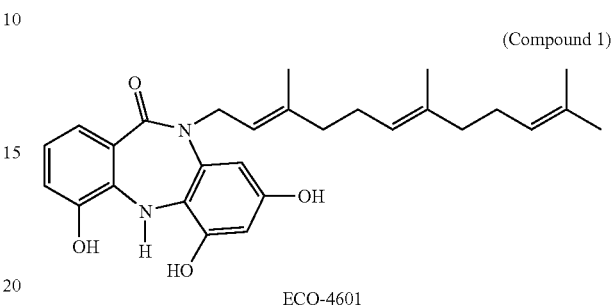

(Compound 1)
ECO-4601

Synthetic dibenzodiazepinone analogs were disclosed in the published Canadian patent application 2,248,820 as having anti-histamine properties.

Although many biologically active compounds have been identified from bacteria, there remains the need to obtain novel compounds with enhanced properties. Thus, there exists a considerable need to obtain pharmaceutically active compounds in a cost-effective manner and with high yield. The present invention solves these problems by providing new therapeutic compounds and methods to generate these novel compounds by post-biosynthetic chemical modifications.

SUMMARY OF THE INVENTION

In one aspect, the invention relates to dibenzodiazepinone analogues as defined below and represented by derivatives of Compound 1, and to pharmaceutical compositions comprising a dibenzodiazepinone analogue or a pharmaceutically acceptable salt, solvate or prodrug thereof, together with a pharmaceutically acceptable carrier. In one embodiment, the dibenzodiazepinone analogue is represented by a compound of Formula I as defined below, or an ether, ester, N-alkylated and N-acylated derivative, or a pharmaceutically acceptable salt, solvate or prodrug of a compound of Formula I. In a further embodiment, the dibenzodiazepinone analogue is represented by any one of Compounds 2 to 7, 9 to 11, 13 to 130, and 131 to 154 as defined below, or an ether, an ester, an N-alkylated or N-acylated derivative, or a pharmaceutically acceptable salt, solvate of prodrug of any one of Compounds 2 to 7, 9 to 11, 13 to 130, and 131 to 154. In a further embodiment, the dibenzodiazepinone analogue is represented by any one of Compounds 2 to 7, 9 to 11, 14, 17, 18, 46, 63, 64, 67, 77, 78, 80, 82 to 85, 87, 89, 92, 95 to 98, 100 to 103, and 105, as defined below, or an ether, an ester, an N-alkylated or N-acylated derivative, or a pharmaceutically acceptable salt, solvate of prodrug of any one of Compounds 1 to 7, 9 to 11, 14, 17, 18, 46, 63, 64, 67, 77, 78, 80, 82 to 85, 87, 89, 92, 95 to 98, 100 to 103, and 105.

In another aspect of the invention, the dibenzodiazepinone analogue is represented by a compound of Formula II as defined below, or a hydrogenated or hydroalkoxylated farnesyl derivative, or a pharmaceutically acceptable salt, solvate or prodrug of a compound of Formula II. In another embodiment, the dibenzodiazepinone analogue is represented by any one of Compounds 2, 14, 62, 63, 64, 67, 68, 69, 70, 72, 78, 79, 80, 81, 85, 86, 87, and 98 to 100 as defined below, or a pharmaceutically acceptable salt, solvate or prodrug, or salt of a prodrug of any one of Compounds 2, 14, 62, 63, 64, 67, 68, 69, 70, 72, 78, 79, 80, 81, 85, 86, 87, and 98 to 104. In a further embodiment, the dibenzodiazepinone analogue is represented by any one of Compounds 2, 14, 63, 64, 67, 78, 80, 85, 87, 98, and 100 as defined below, or a pharmaceutically acceptable solvate or prodrug of any one of Compounds 2, 14, 63, 64, 67, 78, 80, 85, 87, 98, and 100.

In yet another aspect of the invention, the dibenzodiazepinone analogue is represented by any one of Compounds 40-46, and 97 as defined below, or a pharmaceutically acceptable solvate or prodrug of any one of Compounds 40-46, 97, and 155 to 161.

The invention further encompasses a dibenzodiazepinone analogue obtained by a method comprising one or more step of chemically modifying Compound 1. In one embodiment the dibenzodiazepinone analogue is a compound of Formula I. In another embodiment, the dibenzodiazepinone analogue is a compound of Formula II, or a hydrogenated or hydroalkoxylated farnesyl derivative. In a further embodiment, the dibenzodiazepinone analogue is selected from Compounds 2 to 7, 9 to 11, and 13 to 130. In another embodiment the dibenzodiazepinone analogue is selected from Compounds 2 to 7, 9 to 11, 14, 17, 18, 46, 63, 64, 67, 77, 78, 80, 82 to 85, 87, 89, 92, 95 to 98, 100 to 103, 105, 107 and 108. In another embodiment the dibenzodiazepinone analogue is selected from Compounds 2, 14, 62, 63, 64, 67, 68, 69, 70, 72, 78, 79, 80, 81, 85, 86, 87, 98 to 100. In another embodiment the dibenzodiazepinone analogue is selected from Compounds 2, 14, 63, 64, 67, 78, 80, 85, 87, 98, and 100. In another embodiment the dibenzodiazepinone analogue is selected from Compounds 46, and 97.

The invention further encompasses a process for making a dibenzodiazepinone compound, comprising chemically modifying the farnesyl dibenzodiazepinone Compound 1, and optionally isolating and purifying the dibenzodiazepinone compound produced. In one embodiment, the chemical modification step comprises at least one step selected from N-alkylations, N-acylations, O-alkylations, O-acylations, and modifications of the double bonds of the farnesyl side chain including, hydrogenation, electrophilic additions (e.g., epoxidation, dihydroxylation, hydration, hydroalkoxylation, hydroamidation, and the like), and double bond cleavage, like ozonolysis, and reduction of the ozonolysis product. In a subclass of this embodiment, the farnesyl side chain modification reaction is partial (one or two double bonds modified) or complete (all three double bonds are modified).

The invention further encompasses a method of inhibiting the growth of a neoplastic cell, the method comprising contacting the cancer cell with a compound of Formula I, such that growth of the neoplastic cell is inhibited. In one embodiment, the compound is a compound selected from Compounds 2 to 7, 9 to 11, and 13 to 130. In another embodiment, the compound is selected from Compounds 2 to 7, 9 to 11, 14, 17, 18, 46, 63, 64, 67, 77, 78, 80, 82 to 85, 87, 89, 92, 95 to 98, 100 to 103, 105 and 107-108. In another embodiment, the compound is a compound of Formula II, or a hydrogenated or hydroalkoxylated farnesyl derivative. In another embodiment, the compound is selected from Compounds 2, 14, 62, 63, 64, 67, 68, 69, 70, 72, 78, 79, 80, 81, 85, 86, 87, and 98 to 100. In another embodiment, the compound is selected from Compounds 2, 14, 63, 64, 67, 78, 80, 85, 87, 98, and 100. In another embodiment the compound is selected from Compounds 40-46, and 97.

The invention further encompasses a method of inhibiting the growth of a neoplastic cell in a mammal, the method comprising administering a compound of Formula I to a mammal comprising a neoplastic cell, such that growth of the neoplastic cell is inhibited in the mammal. In one embodiment, the compound is a compound selected from Compounds 2 to 7, 9 to 11, and 13 to 130. In another embodiment, the compound is selected from Compounds 2 to 7, 9 to 11, 14, 17, 18, 46, 63, 64, 67, 77, 78, 80, 82 to 85, 87, 89, 92, 95 to 98, 100 to 103, 105 and 107-108. In another embodiment, the compound is a compound of Formula II, or a hydrogenated or hydroalkoxylated farnesyl derivative. In another embodiment, the compound is selected from Compounds 2, 14, 62, 63, 64, 67, 68, 69, 70, 72, 78, 79, 80, 81, 85, 86, 87, and 98 to 100. In another embodiment, the compound is selected from Compounds 2, 14, 63, 64, 67, 78, 80, 85, 87, 98, and 100. In another embodiment the compound is selected from Compounds 40-46, and 97.

The invention further encompasses a method of treating a neoplastic, pre-cancerous or cancerous condition in a mammal, comprising the step of administering to the mammal a therapeutically effective amount of a compound of Formula I, such that a neoplastic, pre-cancerous or cancerous condition is treated. In one embodiment, the compound is a compound selected from Compounds 2 to 7, 9 to 11, and 13 to 130. In another embodiment, the compound is selected from Compounds 2 to 7, 9 to 12, 14, 17, 18, 46, 63, 64, 67, 77, 78, 80, 82 to 85, 87, 89, 92, 95 to 98, 100 to 103, 105 and 107-108. In another embodiment, the compound is a compound of Formula II, or a hydrogenated or hydroalkoxylated farnesyl derivative. In another embodiment, the compound is selected from Compounds 2, 14, 62, 63, 64, 67, 68, 69, 70, 72, 78, 79, 80, 81, 85, 86, 87, and 98 to 100. In another embodiment, the compound is selected from Compounds 2, 14, 63, 64, 67, 78, 80, 85, 87, 98, and 100. In another embodiment the compound is selected from Compounds 40-46, and 97.

In one embodiment, the cancer cell, neoplastic, pre-cancerous or cancerous condition, in the above-mentioned methods, is selected from leukemia, melanoma, breast cancer, lung cancer, pancreatic cancer, ovarian cancer, renal cancer, colon or colorectal cancer, prostate cancer, and CNS cancer. In another embodiment, the cancer cell, and pre-cancerous or cancerous condition, in the above-mentioned methods and uses, is selected from leukemia, breast cancer, prostate cancer, and CNS cancer.

DETAILED DESCRIPTION OF THE INVENTION

Figure 1:
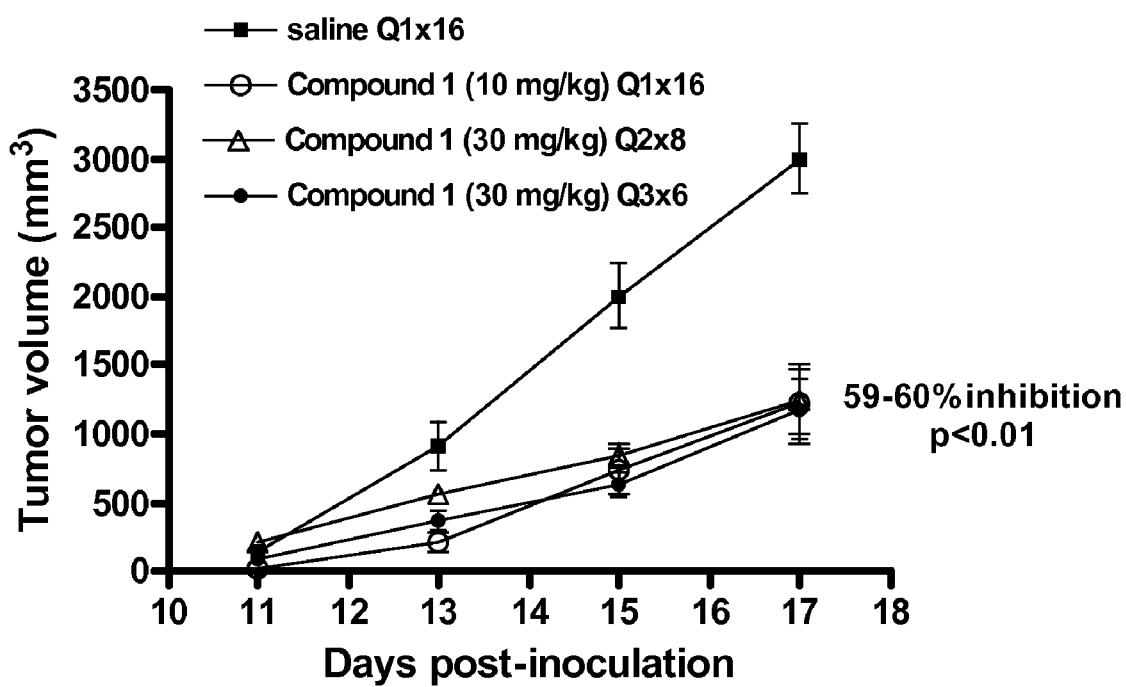
FIG. 1: shows inhibition of tumor growth resulting from bolus administration of 10 to 30 mg/kg of Compound 1 to C6 glioblastoma-bearing mice one day after tumor cell inoculation.

The present invention relates to novel dibenzodiazepinone analogues herein referred as the compounds of Formula I, which include derivatives of Compound 1. Compound 1 is isolated from strains of actinomycetes, *Micromonospora* sp. 046-ECO11 (namely 046(ECO11)) or [S01]046, as described in U.S. Ser. No. 10/762,107.

The invention also relates to a method for producing novel dibenzodiazepinone analogs of Formula I, by chemical modification of the farnesyl dibenzodiazepinone Compound 1. In a subclass of this embodiment, the compound produced is a compound of Formula II or a hydrogenated or hydroalkoxylated farnesyl derivative thereof, or a compound selected from Compounds 40-46, and 97.

The present invention also relates to pharmaceutical compositions comprising a compound of Formula I or II and its pharmaceutically acceptable salts, solvates and derivatives. Compounds of Formula I or II are useful as pharmaceuticals, in particular for use as an inhibitor of cancer cell growth, and mammalian lipoxygenase.

The following detailed description discloses how to make and use the compounds of Formula I or II and compositions containing these compounds to inhibit tumor growth and/or specific disease pathways.

Accordingly, certain aspects of the present invention relate to pharmaceutical compositions comprising the dibenzodiazepinone compounds of the present invention together with a pharmaceutically acceptable carrier, and methods of using the pharmaceutical compositions to treat diseases, including cancer, and chronic and acute inflammation, autoimmune diseases, and neurodegenerative diseases.

I. DEFINITIONS

All technical and scientific terms used herein have the same meaning as commonly understood by one of ordinary skill in the art to which this invention belongs. For convenience, the meaning of certain terms and phrases used in the specification, examples, and appended claims, are provided below.

As used herein, the term "farnesyl dibenzodiazepinone" refers to Compound 1, namely 10-farnesyl-4,6,8-trihydroxy-5,10-dihydrodibenzo[b,e][1,4]diazepin-11-one, also referred to as ECO-4601.

As used herein, the terms "compound(s) of the invention", "dibenzodiazepinone analogue(s)", "dibenzodiazepinone compound(s)", and equivalent expressions refer to a class of dibenzodiazepinone compounds containing a farnesyl moiety or being derived from a farnesyl moiety, and pharmaceutically acceptable salts, solvates and prodrugs thereof. The term includes a compound of Formula I or II, a compound selected from Compounds 2 to 7, 9 to 11, and 13 to 161, or the exemplified compounds of the present invention, Compounds 2 to 7, 9 to 11, 14, 17, 18, 46, 63, 64, 67, 77, 78, 80, 82 to 85, 87, 89, 92, 95 to 98, 100 to 103, 105 and 107-108, or a pharmaceutically acceptable salt, solvate or prodrug of any of the above compounds. As used herein, the term "dibenzodiazepinone analogues" includes compounds of this class that can be used as intermediates in chemical syntheses, and variants containing isotopes different than the most abundant isotope of an atom (e.g, D replacing H, $^{13}C$ replacing $^{12}C$, etc). The compounds of the invention are also sometimes referred as "active ingredients".

As used herein, the term "chemical modification" refers to one or more steps of modifying a dibenzodiazepinone compound, referred to as "starting material", by chemical synthesis. Preferred compounds for use as starting materials in a chemical modification process are Compounds 1 to 161, more preferably Compound 1. Examples of chemical modification steps include N-alkylations, N-acylations, O-alkylations, O-acylations, aromatic halogenation, and modifications of the double bonds of the farnesyl side chain including, hydrogenation, electrophilic additions (e.g., epoxidation, dihydroxylation, hydration, hydroalkoxylation, hydroamidation, and the like), and double bond cleavage like ozonolysis, and reduction of ozonolysis product. Farnesyl side chain modification reaction can be partial (one or two double bonds modified) or complete (three double bonds modified). Chemical modification steps are also defined in the Schemes of Section IIIB, and exemplified in Examples 4 to 9 and Example 13.

The term "ether" refers to a dibenzodiazepinone analogue obtained by the replacement of a hydrogen atom from an alcohol by an R' replacement group by an O-alkylation reaction as defined in Scheme 1 (a) below. More particularly, the term ether encompasses ethers of the alcohols in positions 4, 6, and 8 (see Examples 3-9 for atom numbering).

The term "ester" refers to a dibenzodiazepinone analogue obtained by the replacement of a hydrogen atom from an alcohol by a C(O)R" replacement group by an O-acylation reaction as defined in Scheme 1 (b) below. The term ester also encompasses ester equivalents including, without limitation, carbonate, carbamate, and the like. More particularly, the term "ester" encompasses esters of the alcohols in positions 4, 6, and 8 (see Examples 3-9 for atom numbering).

The term "N-alkylated derivative" refers to a dibenzodiazepinone analogue obtained by the replacement of a hydrogen atom of a nitrogen atom by an R replacement group by an N-alkylation reaction as defined in Scheme 2(a) below. More particularly, the term "N-alkylated derivative" encompasses derivatives substituted at the nitrogen in position 5 (see Examples 3-9 for atom numbering).

The term "N-acylated derivative" refers to a dibenzodiazepinone analogue obtained by the replacement of a hydrogen atom of a nitrogen atom by a C(O)R replacement group by an N-acylation reaction as defined in Scheme 2(b) below. The term N-acylated derivative further encompasses amide equivalents such as, without limitation, urea, guanidine, and the like. More particularly, the term "N-acylated derivative" encompasses derivatives substituted at the nitrogen in position 5 (see Examples 3-9 for atom numbering).

As used herein, the term "hydrogenated or hydroalkoxylated farnesyl derivative" refers to a compound having a modified farnesyl side chain at one to three positions by either saturation (addition of two hydrogen atoms) or by addition of a molecule of alcohol (H and $OC_{1-6}$alkyl) produced respectively by the procedures generally defined in Schemes 3(d) and (e) of Section IIIB, and more specifically in Examples 4, 8 and 13.

As used herein, abbreviations have their common meaning. Unless otherwise noted, the abbreviations "Ac", "Me", "Et", "Pr", "i-Pr", "Bu", "Bz", "Bn" and "Ph", respectively refer to acetyl, methyl, ethyl, propyl (n- or iso-propyl), iso-propyl, butyl (n-, iso-, sec- or tert-butyl), benzoyl, benzyl and phenyl.

Abbreviations in the specification correspond to units of measure, techniques, properties or compounds as follows: "RT" or "Rt" means retention time, "min" means minutes, "h" means hour(s), "μL" means microliter(s), "mL" means milliliter(s), "mM" means millimolar, "M" means molar, "mmole" means millimole(s), "eq" means molar equivalent(s). "High Pressure Liquid Chromatography" or "High Performance Liquid Chromatography" are abbreviated HPLC.

The term "alkyl" refers to linear, branched or cyclic, saturated hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexylmethyl, and the like. Alkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, oxo, guanidino and formyl.

The term "$C_{1-n}$alkyl", wherein n is an integer from 2 to 12, refers to an alkyl group having from 1 to the indicated "n" number of carbons. The $C_{1-n}$alkyl can be cyclic or a straight or branched chain.

The term "linear $C_{1-n}$alkyl", wherein n is an integer from 2 to 10, refers to an alkyl group having from 1 to the indicated "n" number of carbons and being linear, i.e. not cyclic or branched in the vicinity of the attached atom (herein the nitrogen). The $C_{1-n}$alkyl can optionally be substituted with small groups such as acyl, amino, acylamino, acyloxy, carboalkoxy, carboxy, carboxyamido, cyano, halo, hydroxyl, nitro, thio, alkoxy, sulfinyl, sulfonyl, oxo, guanidino and formyl.

The term "alkenyl" refers to linear, branched or cyclic unsaturated hydrocarbon groups containing, from one to six carbon-carbon double bonds. Examples of alkenyl groups include, without limitation, vinyl, 1-propene-2-yl, 1-butene-4-yl, 2-butene-4-yl, 1-pentene-5-yl and the like. Alkenyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The term "$C_{2-n}$alkenyl", wherein n is an integer from 3 to 12, refers to an alkenyl group having from 2 to the indicated "n" number of carbons. The $C_{2-n}$alkenyl can be cyclic or a straight or branched chain.

The term "alkynyl" refers to linear, branched or cyclic unsaturated hydrocarbon groups containing at least one carbon-carbon triple bond. Examples of alkynyl groups include, without limitation, ethynyl, 1-propyne-3-yl, 1-butyne-4-yl, 2-butyne-4-yl, 1-pentyne-5-yl and the like. Alkynyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl, formyl, oxo and guanidine.

The term "$C_{2-n}$alkynyl", wherein n is an integer from 3 to 12, refers to an alkynyl group having from 2 to the indicated "n" number of carbons. The $C_{2-n}$alkynyl can be cyclic or a straight or branched chain.

The term "cycloalkyl" or "cycloalkyl ring" refers to an alkyl group, as defined above, further comprising a saturated or partially unsaturated carbocyclic ring in a single or fused carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. Cycloalkyl groups may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$cycloalkyl", wherein n is an integer from 4 to 15, refers to a cycloalkyl ring or ring system or having from 3 to the indicated "n" number of carbons.

The term "heterocycloalkyl", "heterocyclic" or "heterocycloalkyl ring" refers to a cycloalkyl group, as defined above, further comprising one to four hetero atoms (e.g. N, O, S, P) or hetero groups (e.g. NH, $NR^x$, $PO_2$, SO, $SO_2$) in a single or fused heterocyclic ring system having from three to fifteen ring members (e.g. tetrahydrofuranyl has five ring members, including one oxygen atom). Examples of a heterocycloalkyl, heterocyclic or heterocycloalkyl ring include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and glucuronide. The foregoing heterocycloalkyl groups, as derived from the compounds listed above, may be C-attached or N-attached where such is possible. Heterocycloalkyl, heterocyclic or heterocycloalkyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocycloalkyl, aryl, heteroaryl, alkoxy, aryloxy, sulfinyl, sulfonyl and formyl.

The term "$C_{3-n}$heterocycloalkyl", wherein n is an integer from 4 to 15, refers to an heterocycloalkyl group having from 3 to the indicated "n" number of atoms in the cycle and at least one hetero group as defined above.

The terms "halo" or "halogen" refers to bromine, chlorine, fluorine or iodine substituents.

The term "aryl" or "aryl ring" refers to common aromatic groups having "4n+2" π (pi) electrons, wherein n is an integer from 1 to 3, in a conjugated monocyclic or polycyclic system and having from five to fourteen ring atoms. Aryl may be directly attached, or connected via a $C_{1-3}$alkyl group (also referred to as aralkyl). Examples of aryl include, without limitation, phenyl, benzyl, phenethyl, 1-phenylethyl, tolyl, naphthyl, biphenyl, terphenyl, and the like. Aryl groups may optionally be substituted with one or more substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "$C_{5-n}$aryl", wherein n is an integer from 5 to 14, refers to an aryl group having from 5 to the indicated "n" number of atoms, including carbon, nitrogen, oxygen and sulfur. The $C_{5-n}$aryl can be mono or polycyclic.

The term "heteroaryl" or "heteroaryl ring" refers to an aryl ring, as defined above, further containing one to four heteroatoms selected from oxygen, nitrogen, sulphur or phosphorus. Examples of heteroaryl include, without limitation, pyridyl, imidazolyl, pyrimidinyl, pyrazolyl, triazolyl, tetrazolyl, furyl, thienyl, isooxazolyl, thiazolyl, oxazolyl, isothiazolyl, pyrrollyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl groups. Heteroaryl may optionally be substituted with one or more substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Heteroaryl may be directly attached, or connected via a $C_{1-3}$alkyl group (also referred to as heteroaralkyl). The foregoing heteroaryl groups, as derived from the compounds listed above, may be C-attached or N-attached where such is possible.

The term "$C_{5-n}$heteroaryl", wherein n is an integer from 5 to 14, refers to an heteroaryl group having from 5 to the indicated "n" number of atoms, including carbon, nitrogen, oxygen and sulphur atoms. The $C_{5-n}$heteroaryl can be mono or polycyclic.

The term "amino acid" refers to an organic acid containing an amino group. The term includes both naturally occurring and synthetic amino acids; therefore, the amino group can be but is not required to be, attached to the carbon next to the acid. A C-coupled amino acid substituent is attached to the heteroatom (nitrogen or oxygen) of the parent molecule via its carboxylic acid function. C-coupled amino acid forms an ester with the parent molecule when the heteroatom is oxygen, and an amide when the heteroatom is nitrogen. Examples of amino acids include, without limitation, alanine, valine, leucine, isoleucine, proline, phenylalanine, tryptophan, methionine, glycine, serine, threonine, cysteine, asparagine, glutamine, tyrosine, histidine, lysine, arginine, aspartic acid, glutamic acid, desmosine, ornithine, 2-aminobutyric acid, cyclohexylalanine, dimethylglycine, phenylglycine, norvaline, norleucine, hydroxylysine, allo-hydroxylysine, hydroxyproline, isodesmosine, allo-isoleucine, ethylglycine, beta-alanine, aminoadipic acid, aminobutyric acid, ethyl asparagine, and N-methyl amino acids. Amino acids can be pure L or D isomers or mixtures of L and D isomers.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, including chiral chromatography (e.g. HPLC), immunoassay techniques, or the use of covalently (e.g. Mosher's esters) or non-covalently (e.g. chiral salts) bound chiral reagents to respectively form a diastereomeric ester or salt, which can be further separated by conventional methods, such as chromatography, distillation, crystallization or sublimation. The chiral ester or salt is then cleaved or exchanged by conventional means, to recover the desired isomer(s).

The invention encompasses isolated or purified compounds. An "isolated" or "purified" compound refers to a compound which represents at least 10%, 20%, 50%, 80% or 90% of the mixture by weight, provided that the mixture comprising the compound of the invention has demonstrable (i.e. statistically significant) biological activity including cytostatic, cytotoxic, enzyme inhibitory or receptor binding action when tested in conventional biological assays known to a person skilled in the art.

The term "pharmaceutically acceptable salt" refers to nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, methanol, ethanol, isopropanol, or acetonitrile are preferred. Another method for the preparation of salts is by the use of ion exchange resins. The term "pharmaceutically acceptable salt" includes both acid addition salts and base addition salts, either of the parent compound or of a prodrug or solvate thereof. The nature of the salt is not critical, provided that it is pharmaceutically acceptable. Exemplary acids used in acid addition salts include, without limitation, hydrochloric, hydrobromic, hydroiodic, nitric, carbonic, sulfuric, sulfonic, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts, such as those made from N,N'-dibenzylethylenediamine, chloroprocaine, choline, diethanolamine, ethylenediamine, N-methylglucamine, lysine, procaine and the like. Additional examples of pharmaceutically acceptable salts are listed in Berge et al (1977), *Journal of Pharmaceutical Sciences*, vol 66, no 1, pp 1-19, the content of which is incorporated herein by reference in its entirety.

The term "solvate" refers to a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like.

The term "pharmaceutically acceptable prodrug" means any pharmaceutically acceptable ester, salt of an ester or any other derivative of a compound of this invention, which upon administration to a recipient, is capable of providing, either directly or indirectly, a compound of this invention or a biologically active metabolite or residue thereof. Particularly favored salts or prodrugs are those with improved properties, such as solubility, efficacy, or bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. As used herein, a prodrug is a drug having one or more functional groups covalently bound to a carrier wherein metabolic or chemical release of the drug occurs in vivo when the drug is administered to a mammalian subject. Pharmaceutically acceptable prodrugs of the compounds of this invention include derivatives of hydroxyl groups such as, without limitation, acyloxymethyl, acyloxyethyl and acylthioethyl ethers, esters, amino acid esters, phosphate esters, sulfonate and sulfate esters, and metal salts, and the like.

II. COMPOUNDS OF THE INVENTION

In one aspect, the invention relates to novel dibenzodiazepinone analogues, referred to herein as the compounds of the invention, and to pharmaceutically acceptable salts, solvates and prodrugs thereof.

The compounds of the invention may be characterized as Compound 1 and derivatives of Compound 1, by chemical modifications as defined herein. Compounds 2 to 12, 14, 17, 18, 46, 63, 64, 67, 77, 78, 80, 82 to 85, 87, 89, 92, 95 to 98, 100 to 103, 105 and 107-108 may be characterized by any one of their physicochemical and spectral properties, such as mass and NMR, detailed in Example 4 through Example 9.

In another aspect, the invention relates to dibenzodiazepinone analogues, represented by Formula I:

Formula I

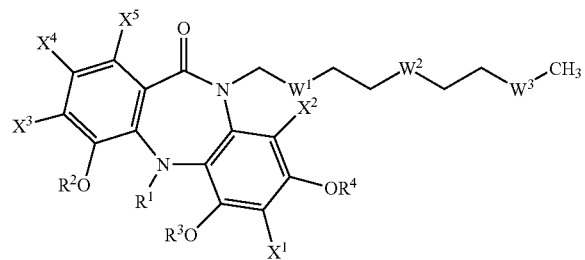

wherein, $W^1$, $W^2$ and $W^3$ are each independently selected from

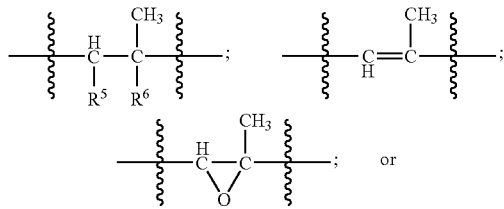

the chain from the tricycle terminates at $W^3$, $W^2$ or $W^1$ with $W^3$, $W^2$ or $W^1$ respectively being either —CH=O, —CH(OC$_{1-6}$alkyl)$_2$, —CH$_2$OH, —CH$_2$OC$_{1-6}$alkyl or C(O)OR$^7$;

$R^1$ is selected from H, C$_{1-10}$alkyl, C$_{2-10}$alkenyl, C$_{2-10}$alkynyl, C$_{6-10}$aryl, C$_{5-10}$heteroaryl, C$_{3-10}$cycloalkyl, C$_{3-10}$heterocycloalkyl, C(O)H, C(O)C$_{1-10}$alkyl, C(O)C$_{2-10}$alkenyl, C(O)C$_{2-10}$alkynyl, C(O)C$_{6-10}$aryl, C(O)C$_{5-10}$heteroaryl, C(O)C$_{3-10}$cycloalkyl; C(O)C$_{3-10}$heterocycloalkyl or a C-coupled amino acid;

$R^2$, $R^3$, and $R^4$ are each independently selected from H, C$_{1-10}$alkyl, C$_{2-10}$alkenyl, C$_{2-10}$alkynyl, C$_{6-10}$aryl, C$_{5-10}$heteroaryl, C$_{3-10}$cycloalkyl, C$_{3-10}$heterocycloalkyl, C(O)H, C(O)C$_{1-10}$alkyl, C(O)C$_{2-10}$alkenyl, C(O)C$_{2-10}$alkynyl, C(O)C$_{6-10}$aryl, C(O)C$_{5-10}$heteroaryl, C(O)C$_{3-10}$cycloalkyl; C(O)C$_{3-10}$heterocycloalkyl or a C-coupled amino acid;

$R^5$ and $R^6$ are each independently selected from H, OH, OC$_{1-6}$alkyl, OC(O)C$_{1-6}$alkyl, NH$_2$, NHC$_{1-6}$alkyl, N(C$_{1-6}$alkyl)$_2$, NHC(O)C$_{1-6}$alkyl;

$R^7$ is selected from H, C$_{1-10}$alkyl, C$_{2-10}$alkenyl, C$_{2-10}$alkynyl, C$_{6-10}$aryl, C$_{5-10}$heteroaryl, C$_{3-10}$cycloalkyl and C$_{3-10}$heterocycloalkyl;

$X^1$, $X^2$, $X^3$, $X^4$ and $X^5$ are each H; or one of $X^1$, $X^2$, $X^3$, $X^4$ or $X^5$ is halogen and the remaining ones are H; and wherein, when any of $R^1$, $R^2$, $R^3$, $R^4$, $R^5$, $R^6$ and $R^7$ comprises an alkyl, alkenyl, alkynyl, aryl, heteroaryl, cycloalkyl, or heterocycloalkyl group, then the alkyl, alkenyl, alkynyl, aryl, heteroaryl, cycloalkyl, or heterocycloalkyl group is optionally substituted with substituents selected from acyl, amino, acylamino, acyloxy, carboalkoxy, carboxy, carboxyamido, cyano, halo, hydroxyl, nitro, thio, C$_{1-6}$alkyl, C$_{2-7}$alkenyl, C$_{2-7}$alkynyl, C$_{3-10}$cycloalkyl, C$_{3-10}$heterocycloalkyl, C$_{6-10}$aryl, C$_{5-10}$heteroaryl, alkoxy, aryloxy, sulfinyl, sulfonyl, oxo, guanidino and formyl;

with the proviso that when $W^1$, $W^2$ and $W^3$ are all —CH=C(CH$_3$)—, $X^1$, $X^2$, $X^3$, $X^4$ and $X^5$ are all H, and $R^2$, $R^3$ and $R^4$ are all H, then $R^1$ is not H;

with the proviso that when $W^1$, $W^2$ and $W^3$ are all —CH=C(CH$_3$)—, $X^1$, $X^2$, $X^3$, $X^4$ and $X^5$ are all H, and $R^1$ is H, then $R^2$, $R^3$ and $R^4$ are not all CH$_3$ or all C(O)CH$_3$;

with the proviso that when the chain from the tricycle terminates at $W^1$ or $W^2$ with $W^2$ or $W^1$ respectively being either —CH=O, —CH(OC$_{1-6}$alkyl)$_2$, —CH$_2$OH, —CH$_2$OC$_{1-6}$alkyl or C(O)OR$^7$, then $R^1$ is H;

and an ester, ether, N-alkylated or N-acylated derivative, or a pharmaceutically acceptable salt, solvate or prodrug thereof.

In further aspect, the invention relates to dibenzodiazepinone analogues, represented by Formula II:

Formula II

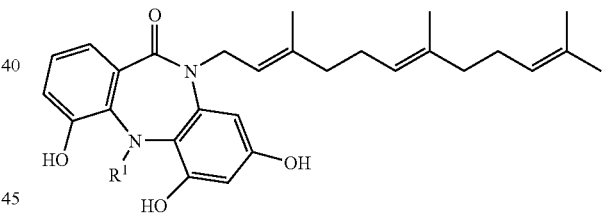

wherein, $R^1$ is a linear C$_{1-10}$alkyl;

or a farnesyl derivative thereof, wherein said farnesyl derivative has one, two or three hydrogenated or hydroalkoxylated double bonds;

or a pharmaceutically acceptable salt or prodrug thereof.

In one embodiment, $R^1$ is H, and all other groups are as previously disclosed. In another embodiment, $R^1$ is —CH$_3$, and all other groups are as previously disclosed. In another embodiment, $R^1$ is C$_{1-10}$alkyl, and all other groups are as previously disclosed. In a subclass of this embodiment, the alkyl group is optionally substituted with a substituent selected from halo, fluoro, C$_{6-10}$aryl, and C$_{5-10}$heteroaryl.

In another embodiment, $R^1$ is —C(O)C$_{1-10}$alkyl, and all other groups are as previously disclosed. In another embodiment, $R^2$ is H, and all other groups are as previously disclosed. In another embodiment, $R^3$ is H, and all other groups are as previously disclosed. In another embodiment, $R^4$ is H, and all other groups are as previously disclosed. In another embodiment, $R^2$, $R^3$ and $R^4$ are each H, and all other groups are as previously disclosed. In another embodiment, one of $R^2$, $R^3$ and $R^4$ is $CH_3$, the others being each H, and all other groups are as previously disclosed. In another embodiment, two of $R^2$, $R^3$ and $R^4$ are $CH_3$, the other being H, and all other groups are as previously disclosed. In another embodiment, $R^2$, $R^3$ and $R^4$ are each $CH_3$, and all other groups are as previously disclosed. In another embodiment, $R^2$, $R^3$ and $R^4$ are each H, and $W^1$ is —CH=C($CH_3$)—, and all other groups are as previously disclosed. In another embodiment, $R^2$, $R^3$ and $R^4$ are each H, and $W^2$ is —CH=C($CH_3$)—, and all other groups are as previously disclosed. In another embodiment, $R^2$, $R^3$ and $R^4$ are each H, and $W^3$ is —CH=C($CH_3$)—, and all other groups are as previously disclosed. In another embodiment, $R^1$ is H and $R^2$, $R^3$ and $R^4$ are each H, and all other groups are as previously disclosed. In another embodiment, $R^1$ is H, each of $W^1$, $W^2$, and $W^3$ is —CH=C($CH_3$)—, and all other groups are as previously disclosed. In another embodiment, $R^1$ is H, each of $W^1$, $W^2$, and $W^3$ is —$CH_2$CH($CH_3$)—, and all other groups are as previously disclosed. In another embodiment, $X^1$ is Br, and each of $X^2$, $X^3$, $X^4$ and $X^5$ are H, and all other groups are as previously disclosed. In another embodiment, if each of $W^1$, $W^2$ and $W^3$ are —CH=C($CH_3$)—, and each of $R^2$, $R^3$, and $R^4$ are H, then $R^1$ is not H. In further embodiment, if each of $W^1$, $W^2$ and $W^3$ are —CH=C($CH_3$)—, and each of $R^2$, $R^3$, and $R^4$ are H, then $R^1$ is not $CH_3$. In further embodiment, if each of $W^1$, $W^2$ and $W^3$ are —CH=C($CH_3$)—, and each of $R^2$, $R^3$, and $R^4$ are H, then $R^1$ is neither H nor $CH_3$. The invention encompasses all esters, ethers, N-alkylated or N-acylated derivatives, and pharmaceutically acceptable salts, solvates and prodrugs of the foregoing compounds.

The following are exemplary compounds of the invention, such named compounds are not intended to limit the scope of the invention in any way:

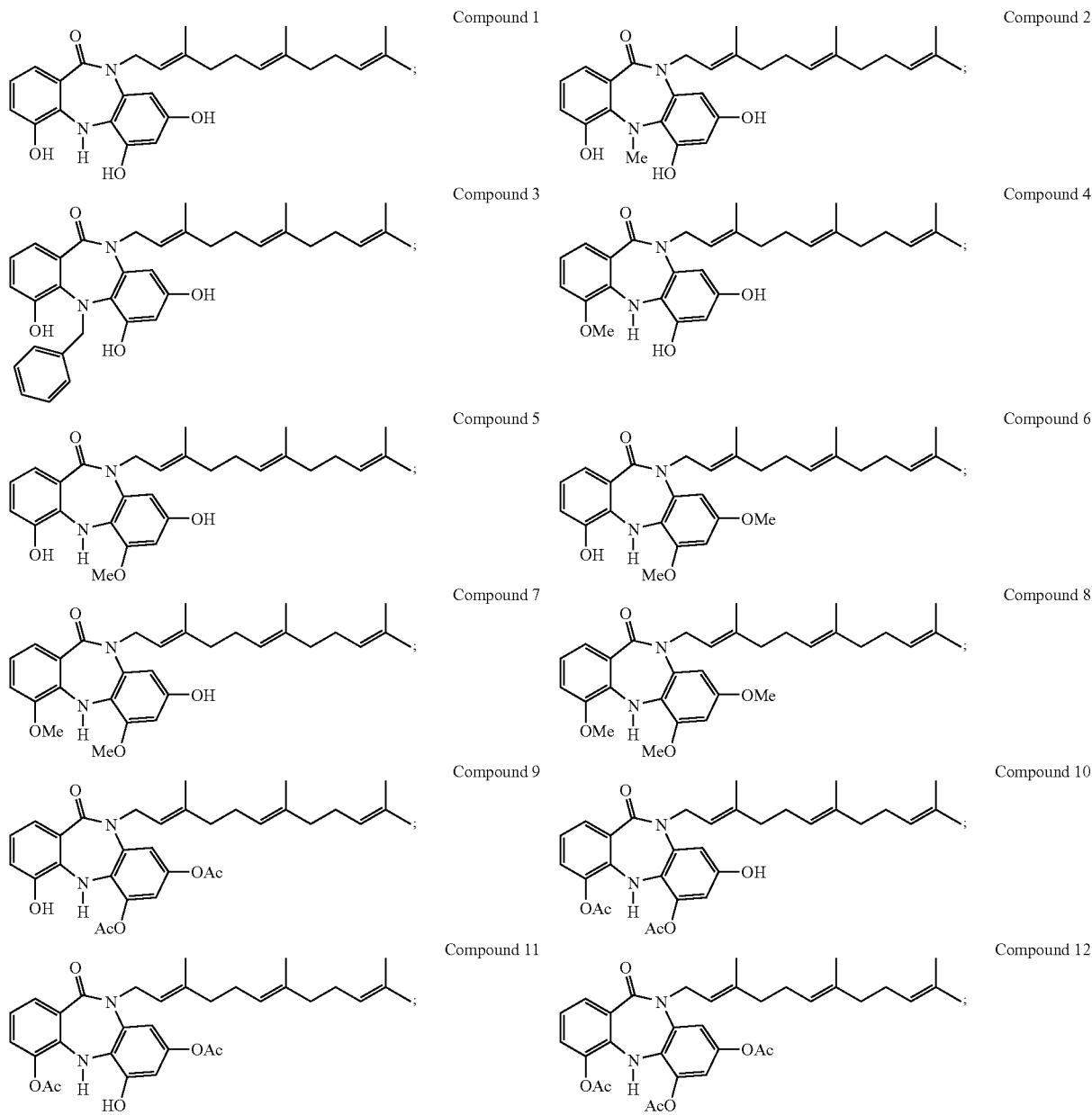

-continued
Compound 13
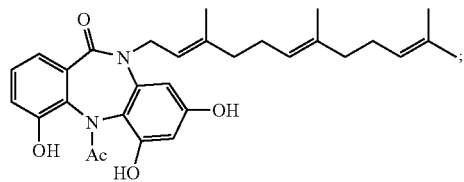
Compound 14
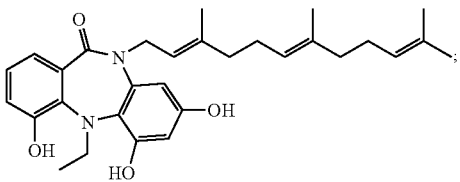
Compound 15
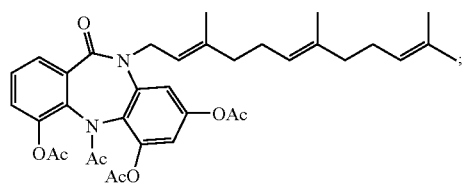
Compound 16
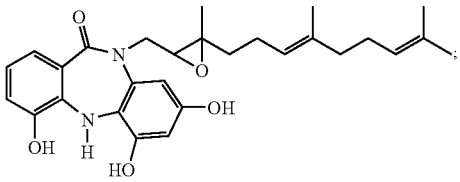
Compound 17
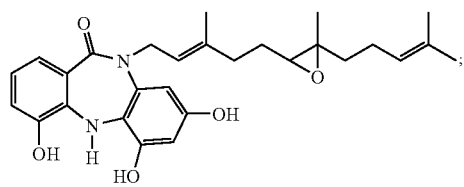
Compound 18
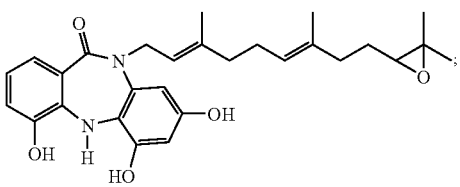
Compound 19
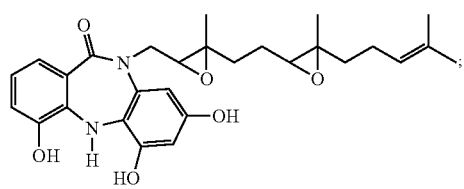
Compound 20
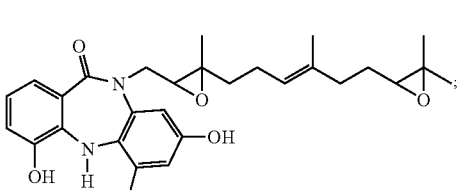
Compound 21
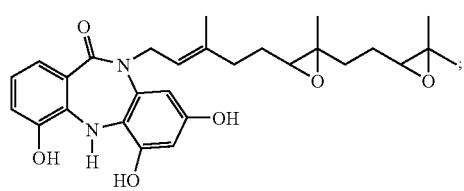
Compound 22
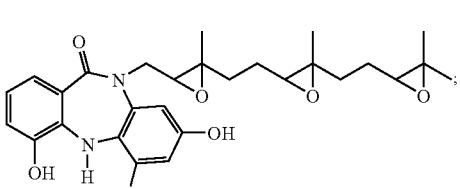
Compound 23
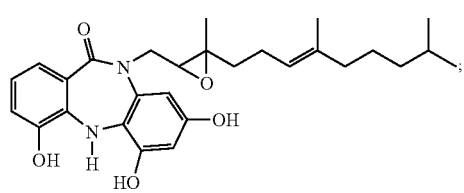
Compound 24
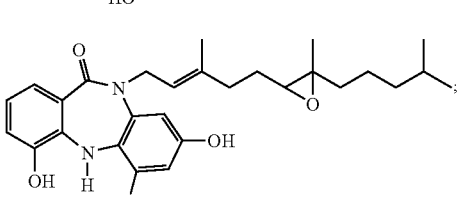
Compound 25
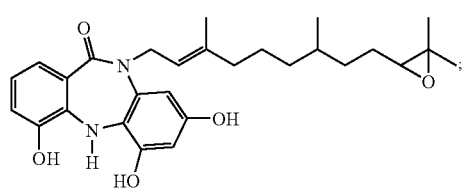
Compound 26
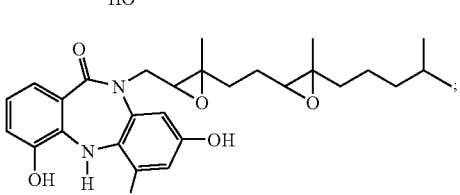
Compound 27
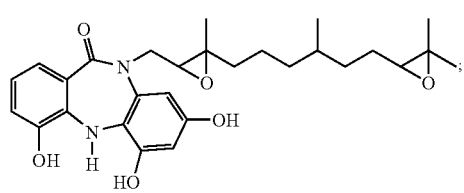
Compound 28
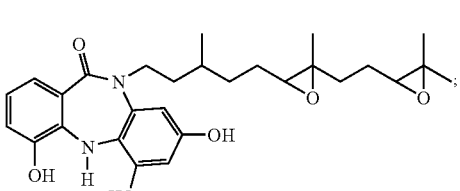

-continued
Compound 29
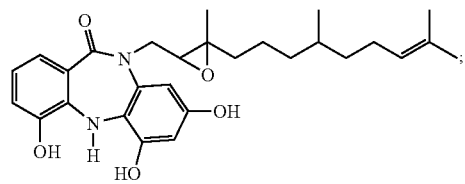
Compound 30
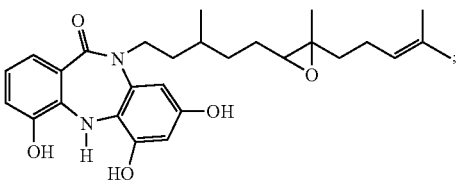
Compound 31
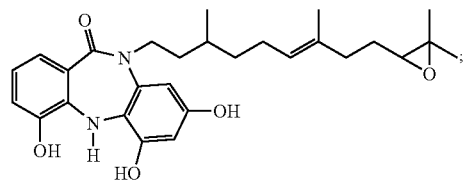
Compound 32
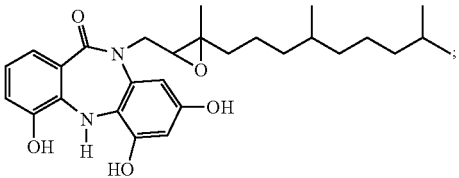
Compound 33
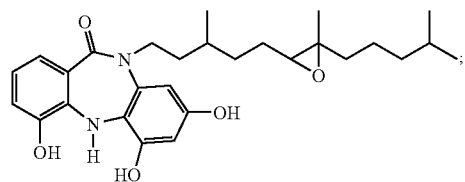
Compound 34
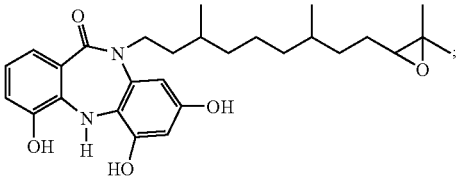
Compound 35
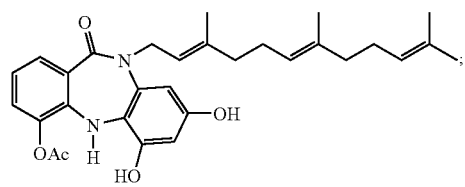
Compound 36
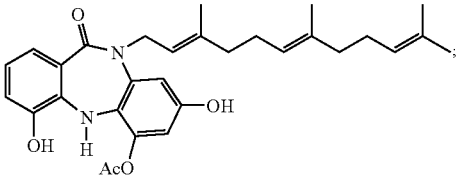
Compound 37
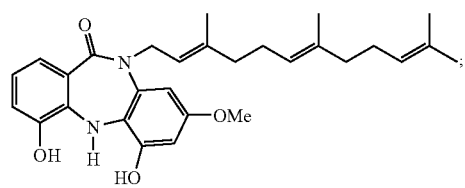
Compound 38
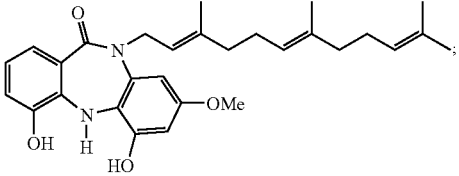
Compound 39
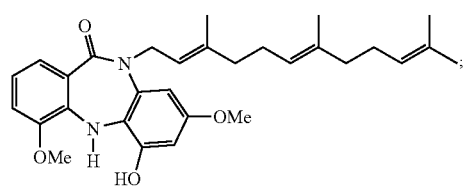
Compound 40
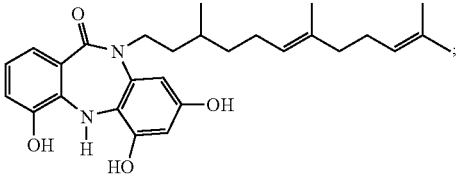
Compound 41
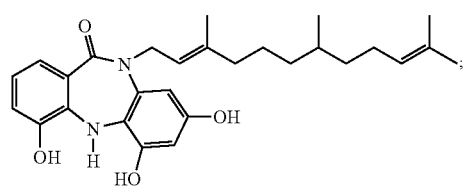
Compound 42
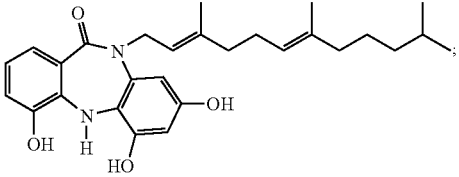
Compound 43
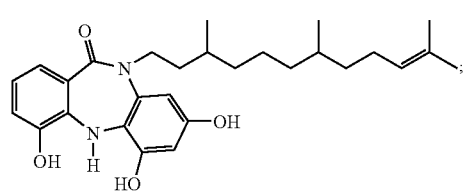
Compound 44
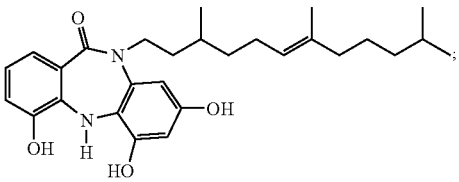

-continued
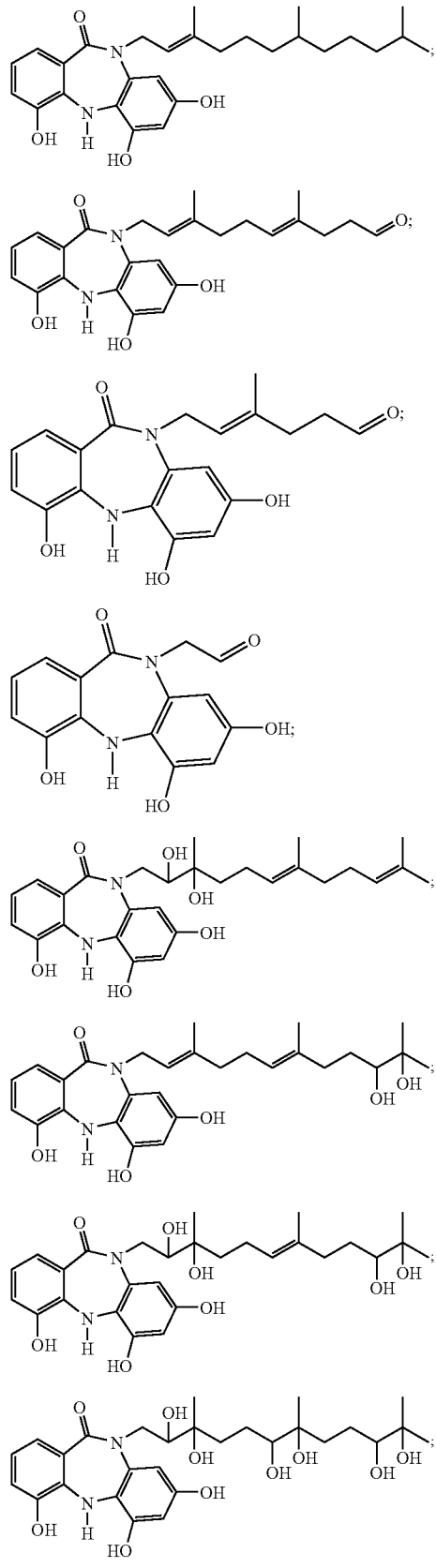
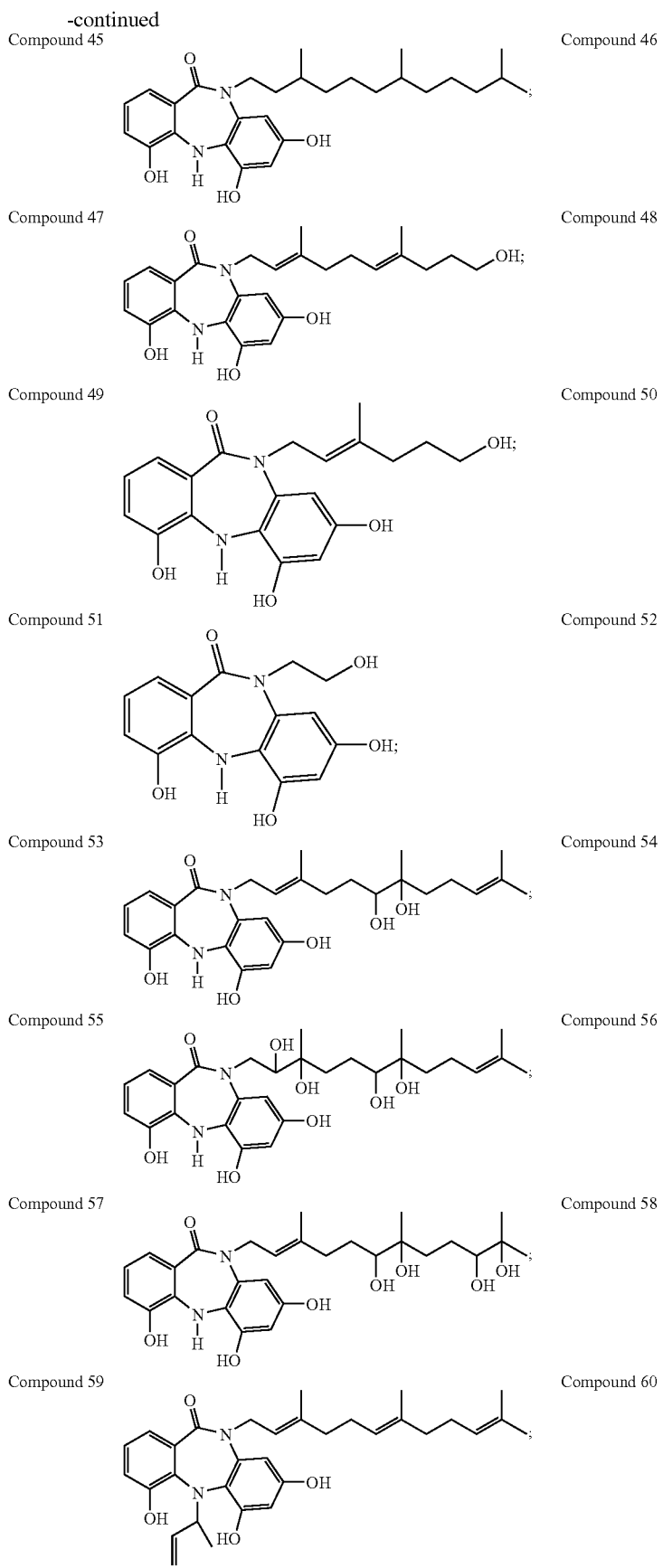

-continued
Compound 61
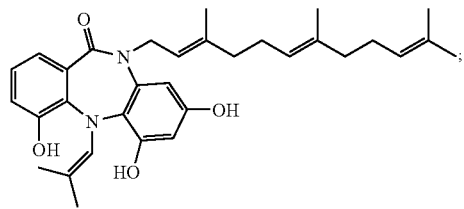
Compound 62
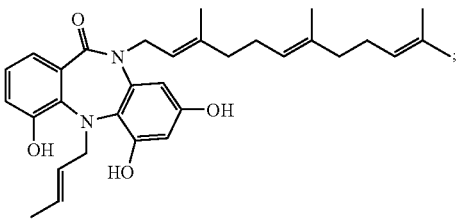
Compound 63
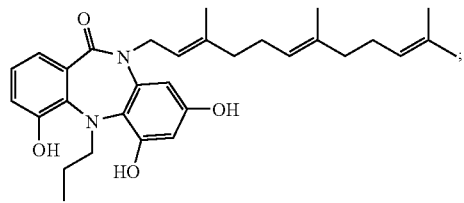
Compound 64
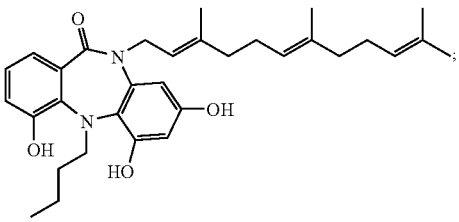
Compound 65
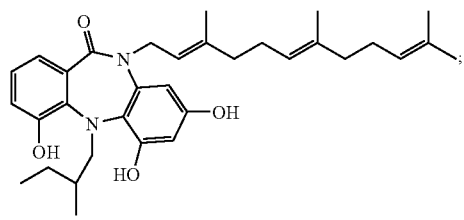
Compound 66
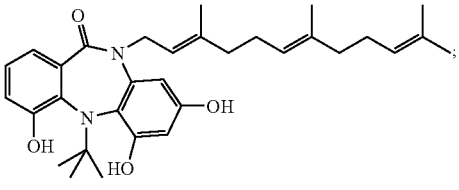
Compound 67
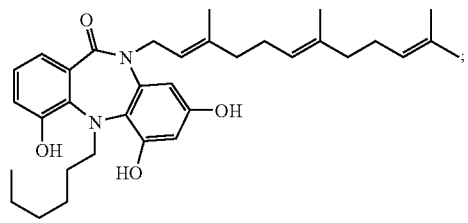
Compound 68
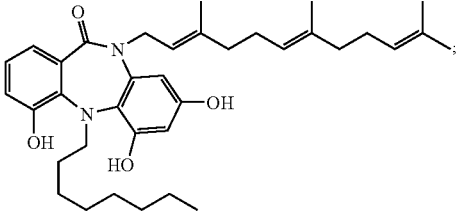
Compound 69
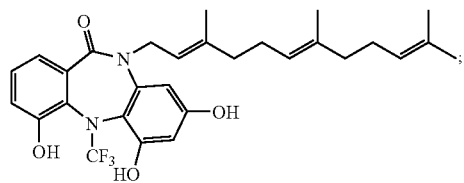
Compound 70
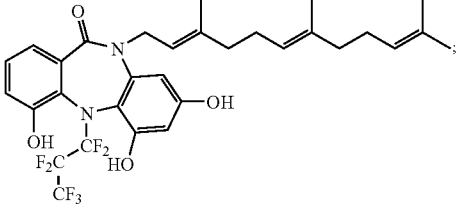
Compound 71
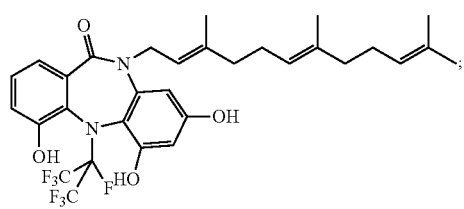
Compound 72
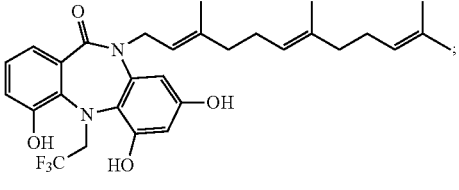
Compound 73
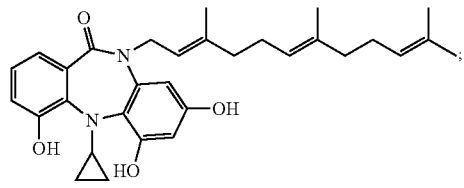
Compound 74
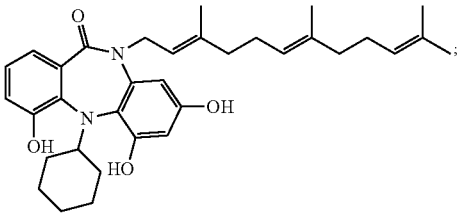

-continued
Compound 75
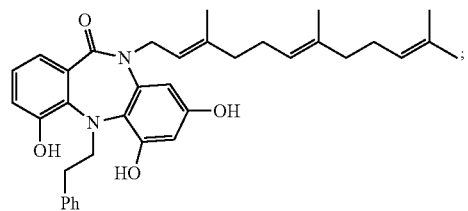
Compound 76
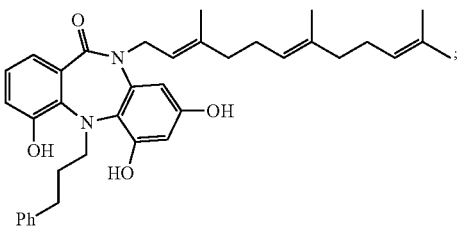
Compound 77
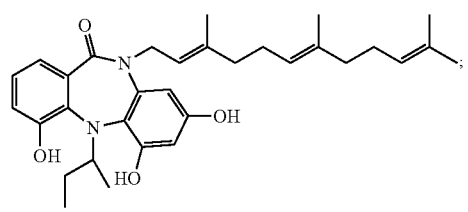
Compound 78
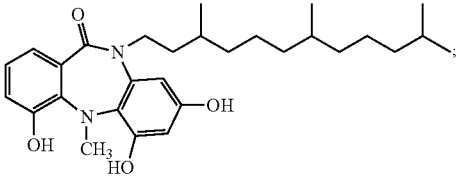
Compound 79
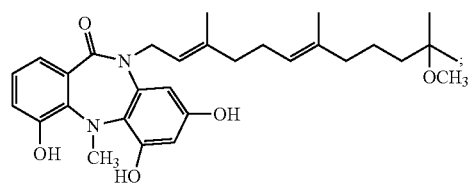
Compound 80
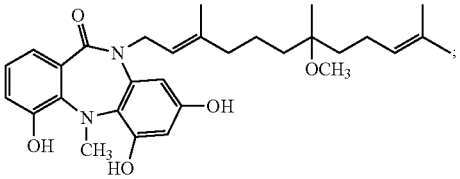
Compound 81
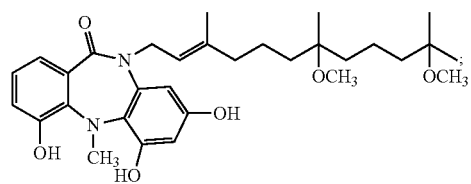
Compound 82
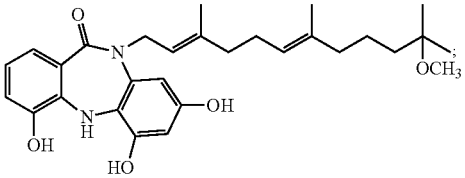
Compound 83
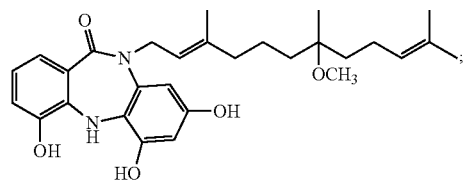
Compound 84
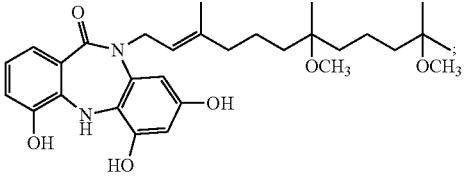
Compound 85
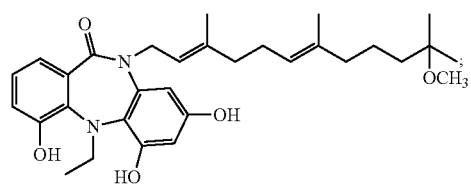
Compound 86
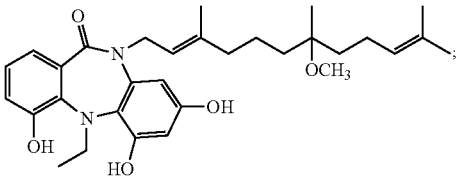
Compound 87
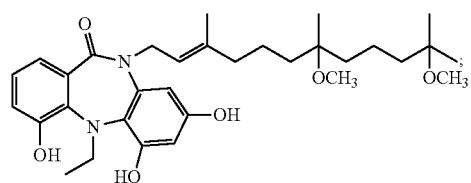
Compound 88
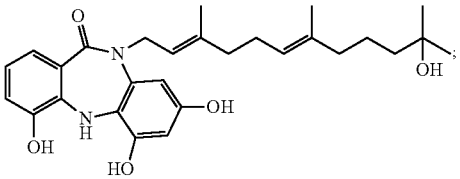
Compound 89
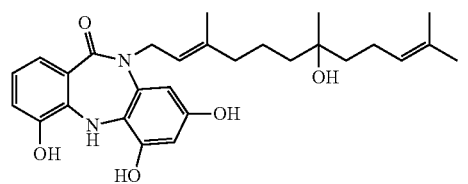
Compound 90
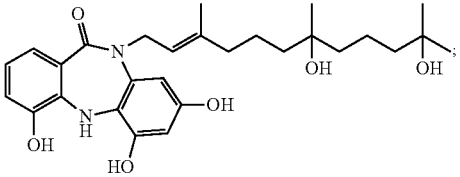

-continued
Compound 91
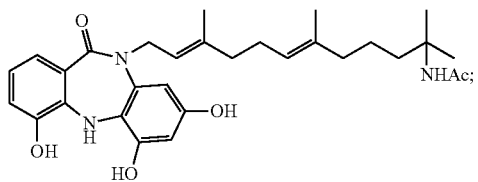
Compound 92
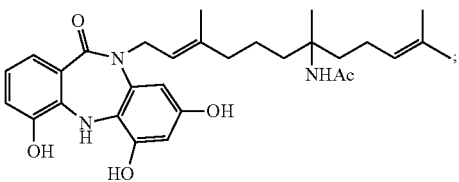
Compound 93
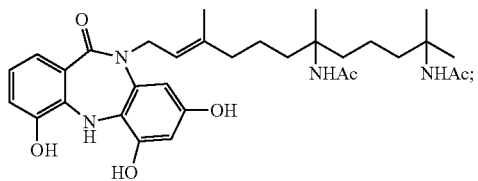
Compound 94
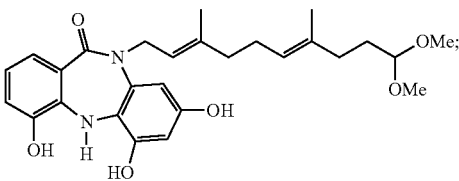
Compound 95
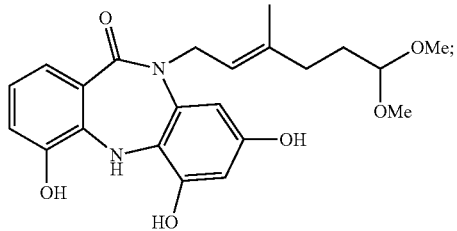
Compound 96
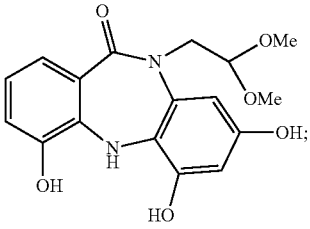
Compound 97
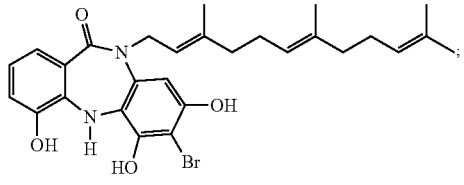
Compound 98
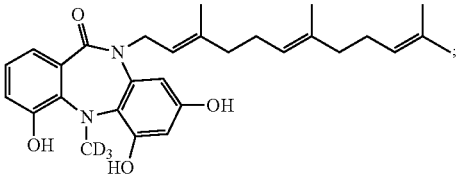
Compound 99
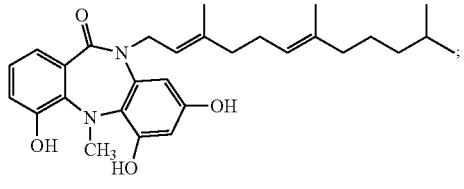
Compound 100
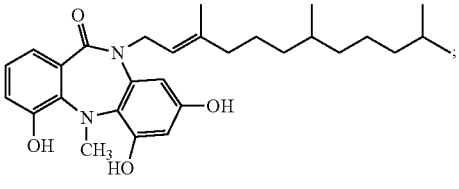
Compound 101
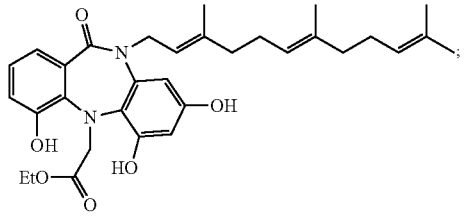
Compound 102
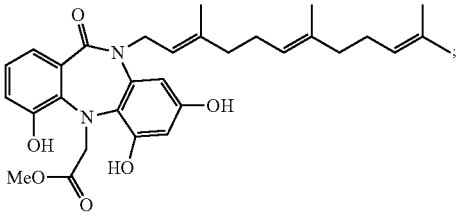
Compound 103
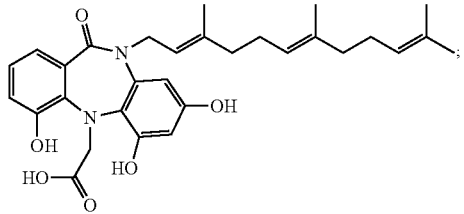
Compound 104
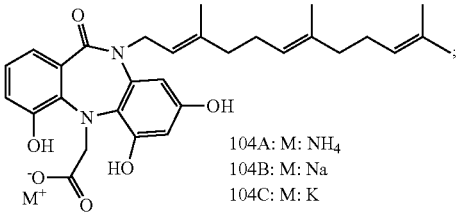
104A: M: NH$_4$
104B: M: Na
104C: M: K Compound 105
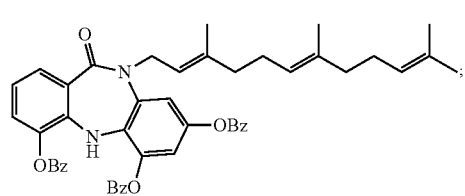
Compound 106
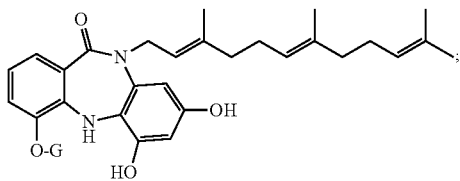
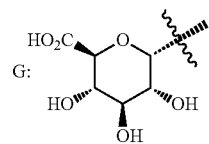
Compound 107
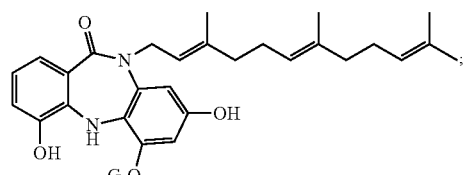
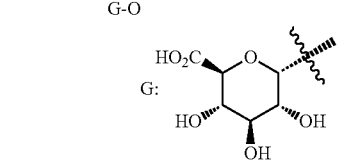
Compound 108
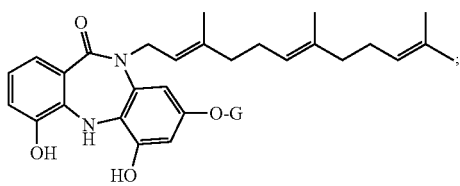
Compound 109
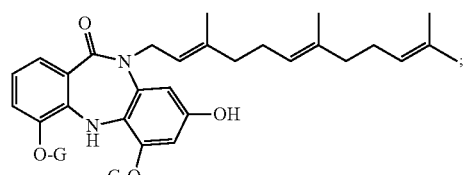
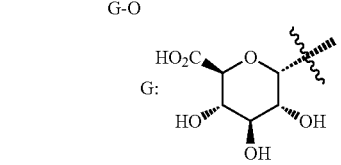
Compound 110
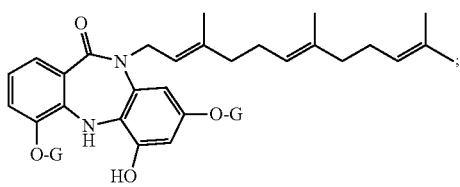
Compound 111
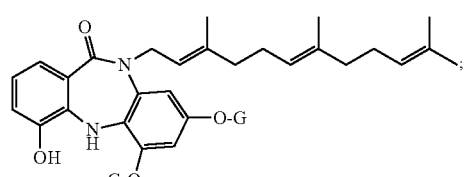
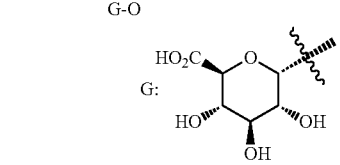
Compound 112
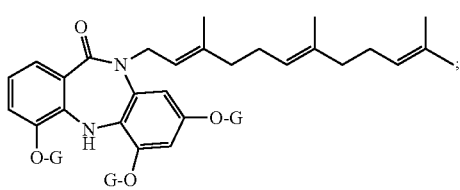

Compound 113
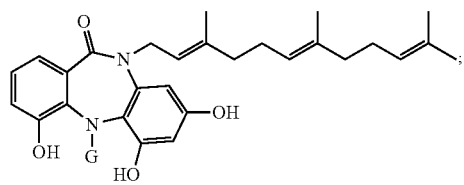
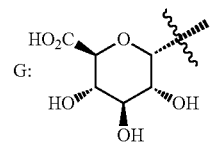
Compound 115
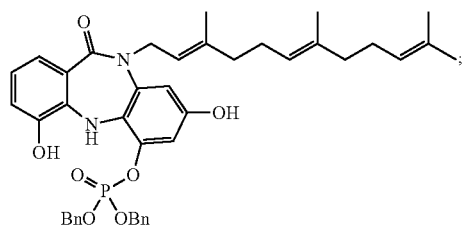
Compound 117
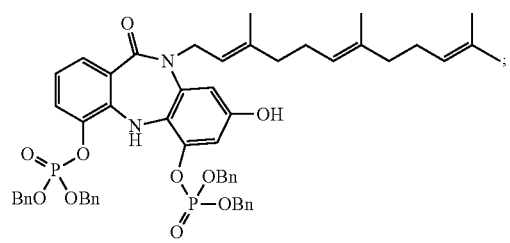
Compound 119
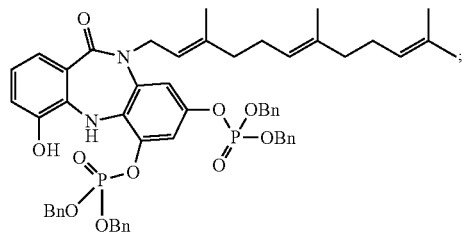
Compound 121
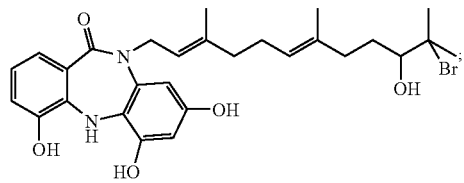
Compound 123
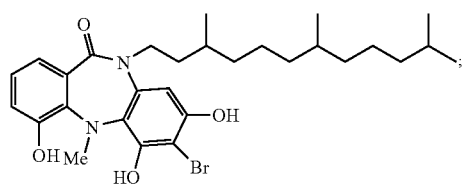
Compound 114
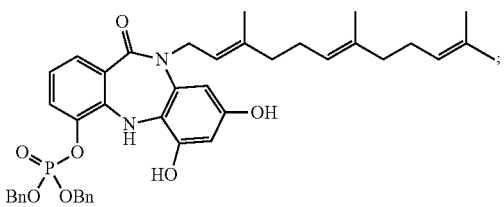
Compound 116
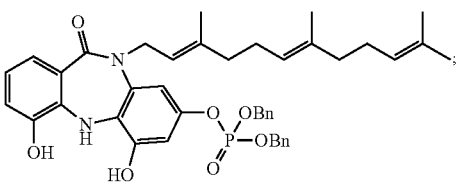
Compound 118
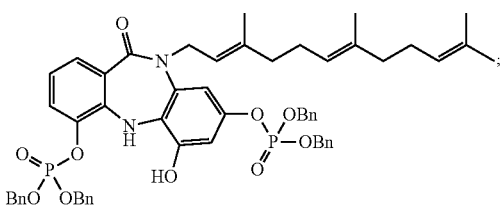
Compound 120
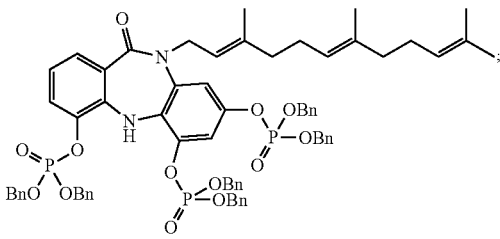
Compound 122
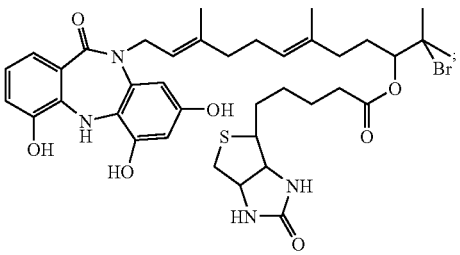
Compound 124
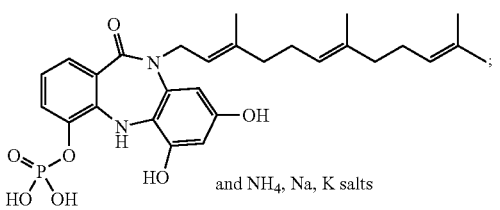
and NH₄, Na, K salts -continued
Compound 125
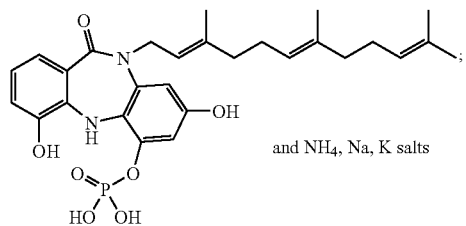
and NH4, Na, K salts
Compound 126
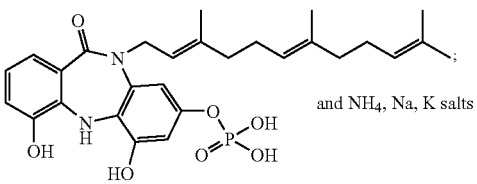
and NH4, Na, K salts
Compound 127
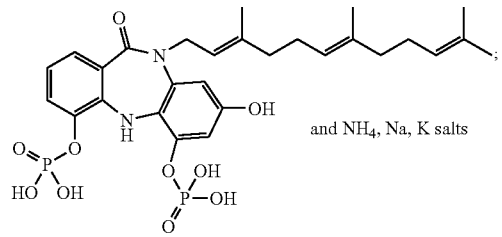
and NH4, Na, K salts
Compound 128
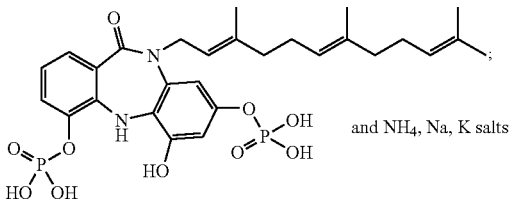
and NH4, Na, K salts
Compound 129
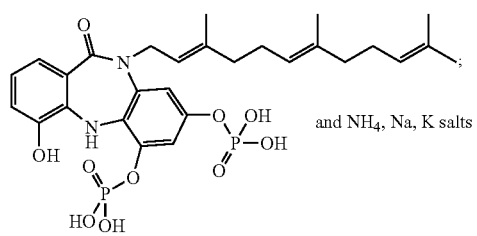
and NH4, Na, K salts
Compound 130
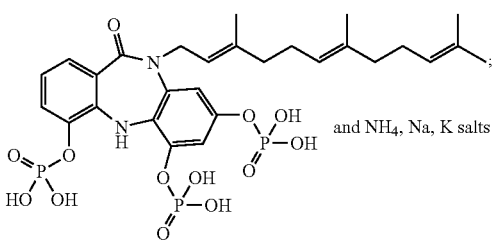
and NH4, Na, K salts
Compound 131
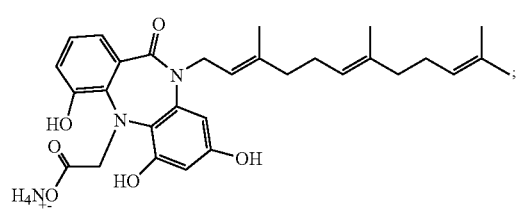
Compound 132
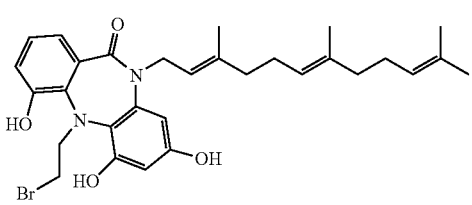
Compound 133
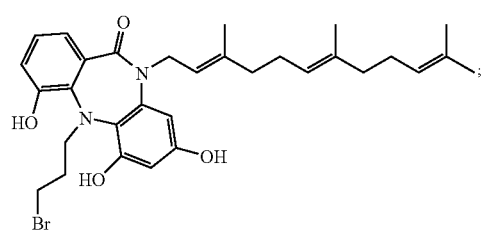
Compound 134
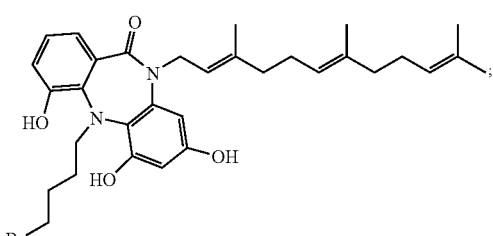
Compoound 135
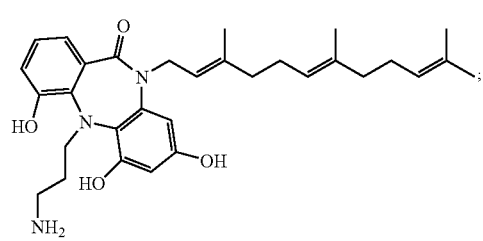
Compound 136
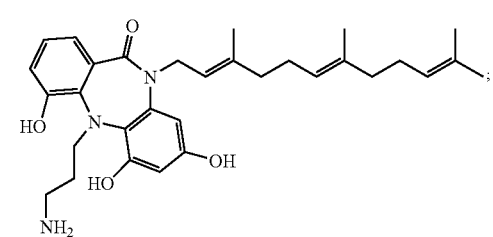

-continued
Compound 137
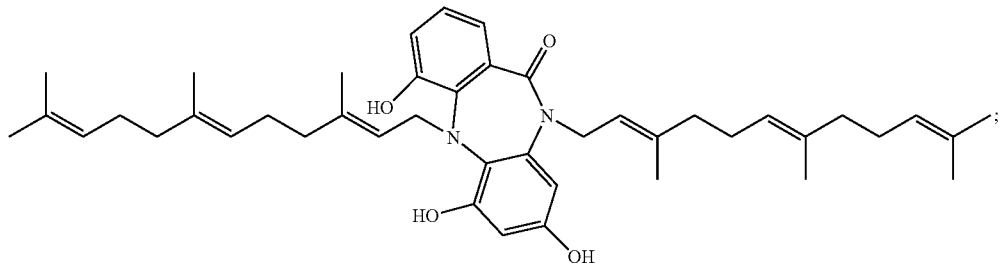
Compound 138
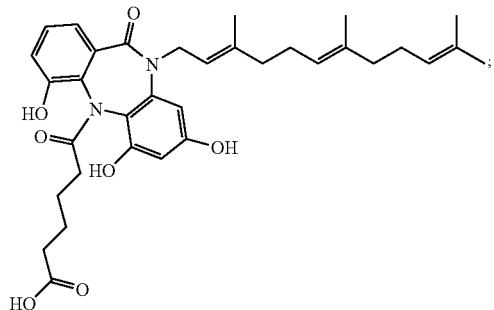
Compound 139
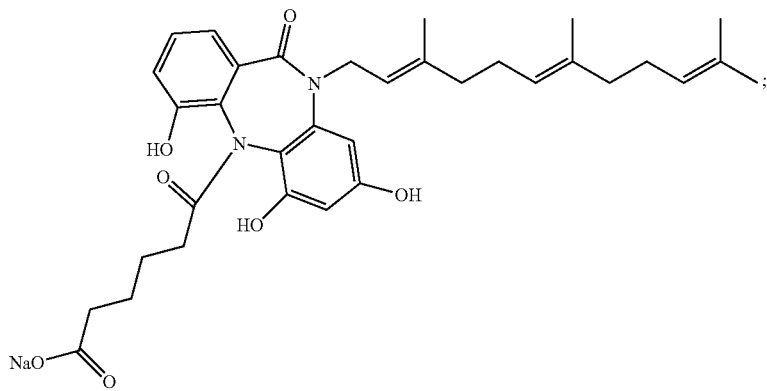
Compound 140
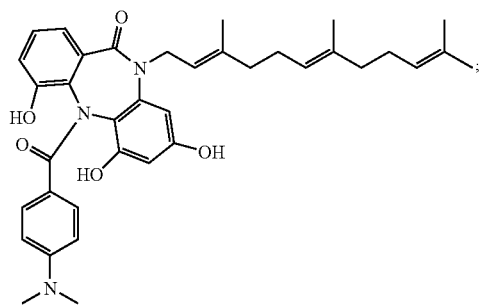
Compound 141
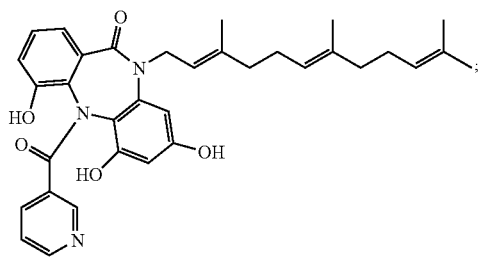
Compound 142
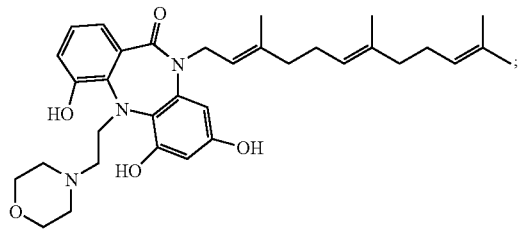

-continued
Compound 143
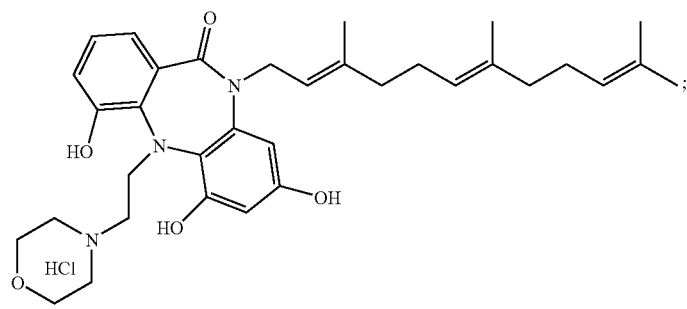
Compound 144
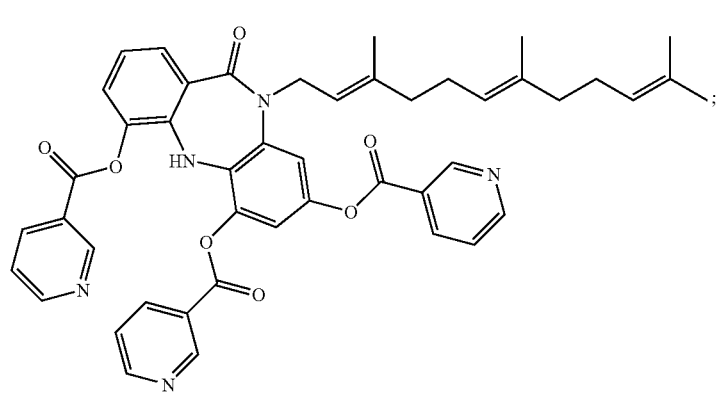
Compoound 145
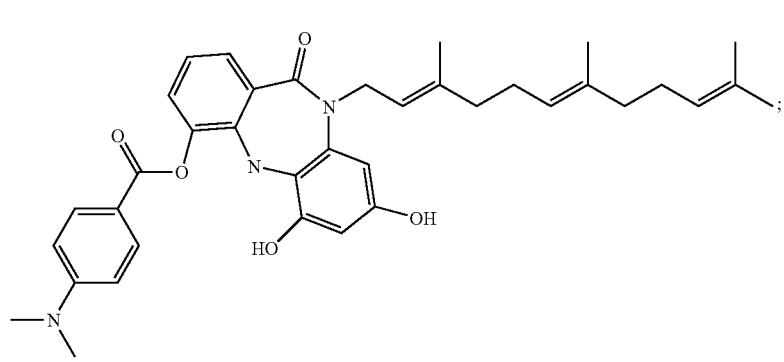
Compound 146
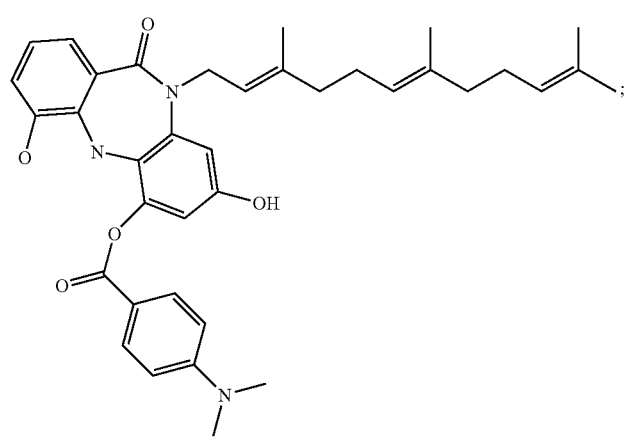

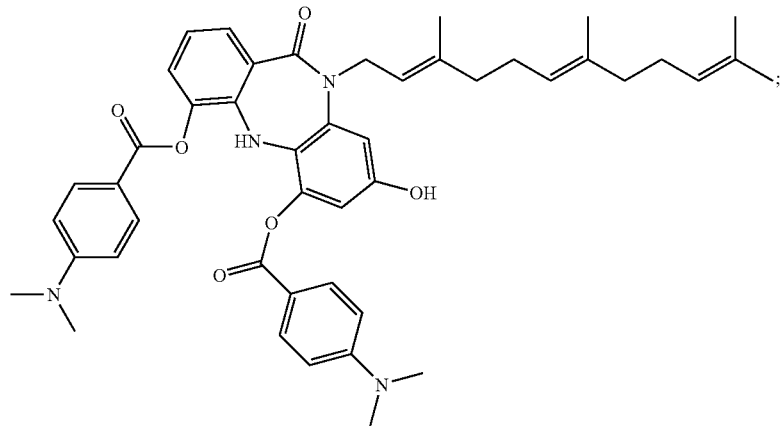
Compound 147
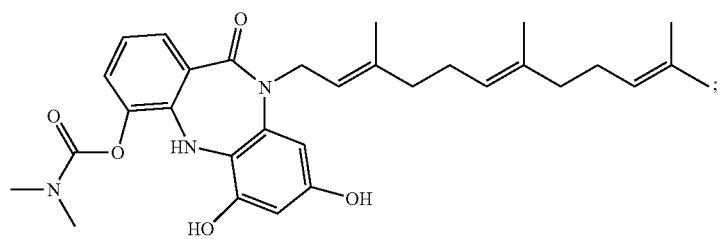
Compound 148
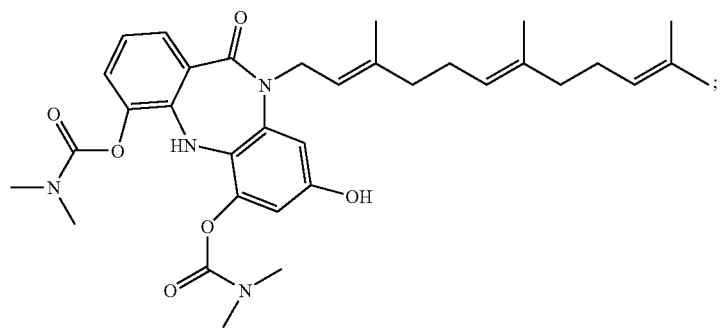
Compound 149
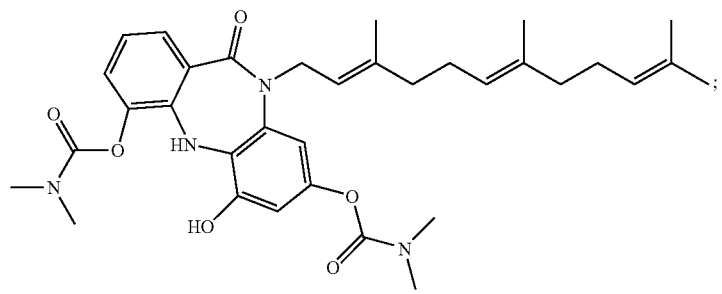
Compound 150
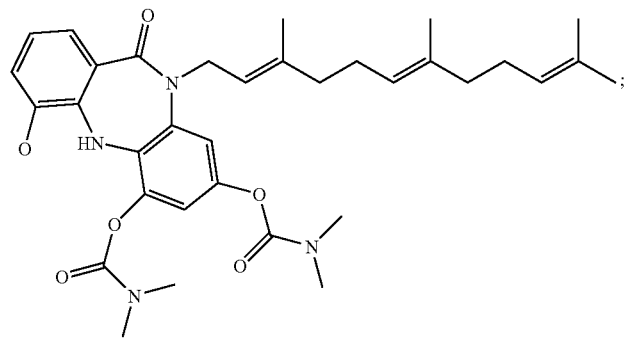
Compound 151

-continued
Compound 152
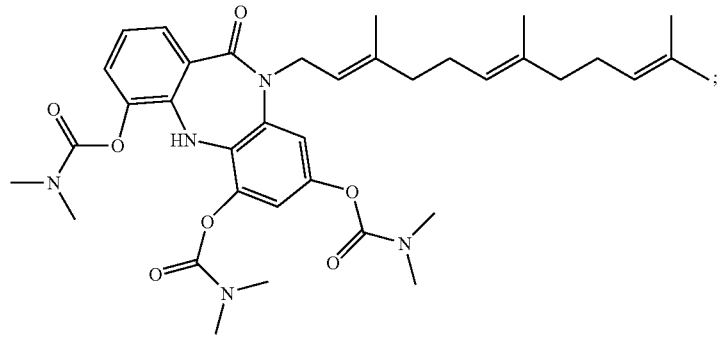
Compound 153
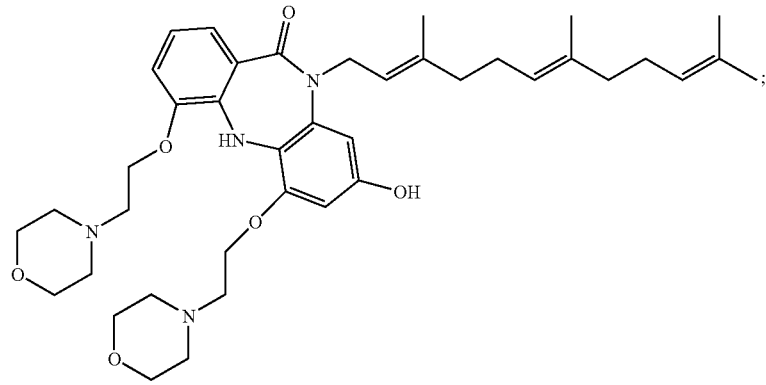
Compound 154
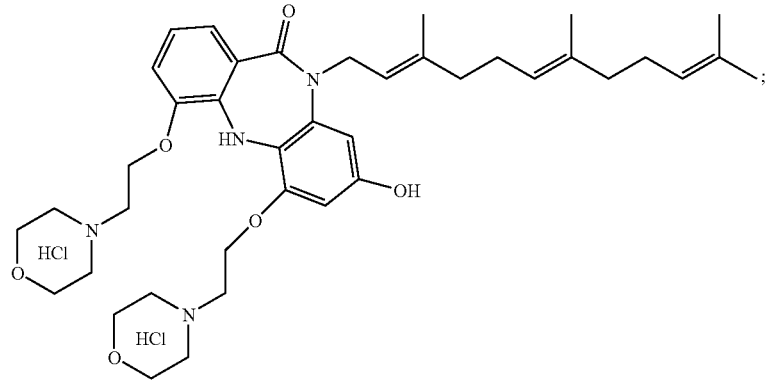
Compound 155
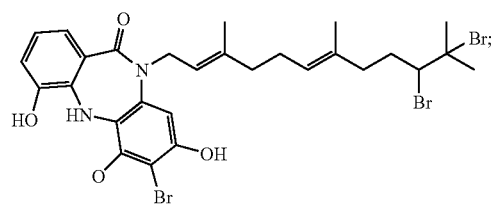
Compound 156
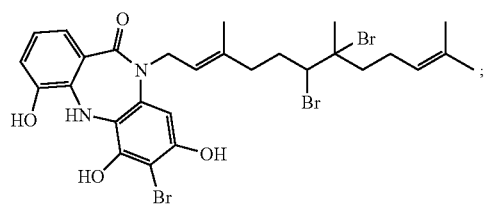
Compound 157
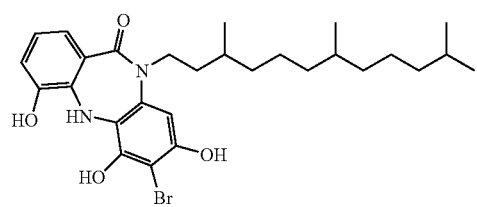
Compound 158
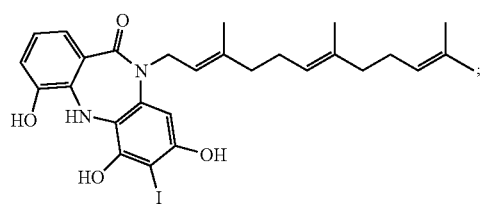

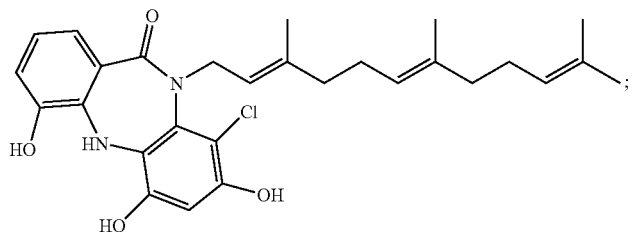

Compound 159

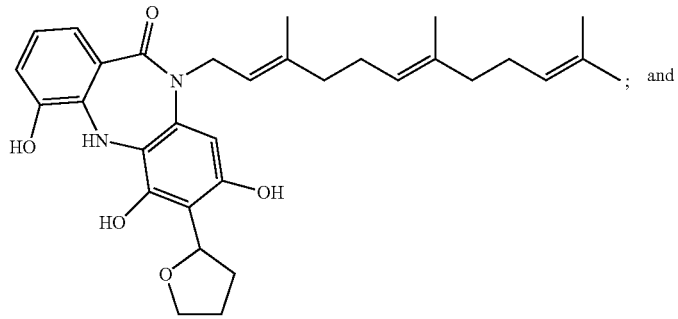

Compound 160

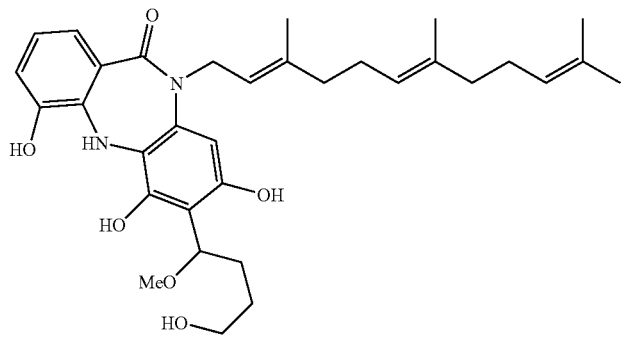

Compound 161 and an ester, ether, N-alkylated or N-acylated derivative, or a pharmaceutically acceptable salt, solvate of prodrug of any one of Compounds 1 to 161.

The invention further provides ethers, esters, N-acylated and N-alkylated derivatives of any of the foregoing compounds.

Certain embodiments expressly exclude one or more of the compounds of Formula I. In one embodiment, Compound 1 is excluded. In another embodiment, Compound 2 is excluded. In a further embodiment, both Compound 1 and Compound 2 are excluded. In a further embodiment, Compound 8 and Compound 12 are excluded.

Prodrugs of the compounds of Formula I or II include compounds wherein one or more of the 4, 6 and 8-hydroxy groups, or any other hydroxyl group on the molecule is bounded to any group that, when administered to a mammalian subject, is cleaved to form the free hydroxyl group. Examples of prodrugs include, but are not limited to, acetate, formate, hemisuccinate, benzoate, dimethylaminoacetate and phosphoryloxycarbonyl derivatives of hydroxy functional groups; dimethylglycine esters, aminoalkylbenzyl esters, aminoalkyl esters or carboxyalkyl esters of hydroxy functional groups. Carbamate and carbonate derivatives of the hydroxy groups are also included. Derivatizations of hydroxyl groups also encompassed, are (acyloxy)methyl and (acyloxy)ethyl ethers, wherein the acyl group contains an alkyl group optionally substituted with groups including, but not limited to, ether, amino and carboxylic acid functionalities, or where the acyl group is an amino acid ester. Also included are phosphate and phosphonate esters, sulfate esters, sulfonate esters, which are in alkylated (such as bis-pivaloyloxymethyl (POM) phosphate triester) or in the salt form (such as sodium phosphate ester ($-P(O)O^-_2Na^+_2$)). For further examples of prodrugs used in anticancer therapy and their metabolism, see Rooseboom et al (2004), *Phamacol. Rev.*, vol 56, 53-102, incorporated herein by reference. When the prodrug contains an acidic or basic moiety, the prodrug may also be prepared as its pharmaceutically acceptable salt.

The compounds of this invention may be formulated into pharmaceutical compositions comprised of a compound of Formula I or II, in combination with a pharmaceutically acceptable carrier, as discussed in Section IV below.

III. METHODS OF PRODUCING DIBENZODIAZEPINONE ANALOGUES

A. Fermentation

The terms "farnesyl dibenzodiazepinone-producing microorganism" and "producer of farnesyl dibenzodiazepinone," as used herein, refer to a microorganism that carries genetic information necessary to produce a farnesyl dibenzodiazepinone compound, whether or not the organism naturally produces the compound. The terms apply equally to organisms in which the genetic information to produce the farnesyl dibenzodiazepinone compound is found in the organism as it exists in its natural environment, and to organisms in which the genetic information is introduced by recombinant techniques.

Compound is produced by isolation of the fermentation broth of *Micromonospora* strains 046-ECO11 and [S01]046 as described in U.S. Ser. No. 10/762,107, incorporated herein by reference in its entirety. It is to be understood that the production of Compound 1 is not limited to the use of the particular strains 046-ECO11 and [S01]046. Rather, other ECO-4601 producing organisms may be used, such as mutants or variants of 046-ECO11 and [S01]046 that can be derived from this organism by known means such as X-ray irradiation, ultraviolet irradiation, treatment with nitrogen mustard, phage exposure, antibiotic resistance selection and the like; or through the use of recombinant genetic engineering techniques. For examples, see *Manual of Industrial Microbiology and biotechnology*, Demain and Solomon, American Society for Microbiology, Washington D.C., 1986; Hesketh et al. (1997), *J. Antibiotics*, vol 50, no 6, 532-535; and Hosoya et al. (1998), *Antimicrobial Agents and Chemotherapy*, vol 42, no 8, 2041-2047), the content of which are incorporated herein by reference in their entirety.

The farnesyl dibenzodiazepinone compound may be biosynthesized by various microorganisms. Microorganisms that may synthesize the farnesyl dibenzodiazepinone compound include but are not limited to bacteria of the order Actinomycetales, also referred to as actinomycetes. Non-limiting examples of members belonging to the genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, for genera that may synthesize the compounds of the invention. The content of which references is incorporated by reference in their entirety.

Farnesyl dibenzodiazepinone-producing microorganisms are cultivated in culture medium containing known nutritional sources for actinomycetes. Such media having assimilable sources of carbon, nitrogen, plus optional inorganic salts and other known growth factors, at a pH of about 6 to about 9. Suitable media include, without limitation, the growth media provided in Table 1. Microorganisms are cultivated at incubation temperatures of about 18° C. to about 40° C. for about 3 to about 40 days.

TABLE 1

Examples of Fermentation Media for Compound 1 Production

| Component | QB | MA | KH | RM | JA | FA | XX | CL |
|---|---|---|---|---|---|---|---|---|
| pH*[1] | 7.2 | 7.5 | 7 | 6.85 | 7.3 | 7.0 | 7.0 | 7.0 |
| Glucose | 12 | | 10 | 10 | | 10 | | |
| Sucrose | | | | 100 | | | | |
| Cane molasses | | | | | | 15 | | |
| Corn starch | | | | | 30 | | | |
| Soluble starch | 10 | 25 | | | | | | |
| Potato dextrin | | | 20 | | | 40 | 20 | 20 |
| Corn steep solid | 5 | | | | | | | |
| Corn steep liquor | 5 | | | | 15 | | | |
| Dried yeast | | 2 | | | | | | |
| Yeast extract | | | 5 | | | | 8.34 | |
| Malt extract | | | | | 35 | | | |
| Pharmamedia ™ | 10 | | | | 15 | | | |
| Glycerol | | | | | | | 30 | 20 |
| NZ-Amine A | | | 5 | | | 10 | | |
| Soybean powder | | 15 | | | | | | |
| Fish meal | | | | | | | | 10 |
| Bacto-peptone | | | | | | | 2.5 | 5 |
| MgSO$_4$•7H$_2$O | | | | | 1 | | | |
| CaCO$_3$ | | 4 | 1 | | 2 | 2 | 3 | 2 |
| NaCl | | 5 | | | | | | |
| (NH$_4$)$_2$SO$_4$ | | 2 | | | | | | 2 |
| K$_2$SO$_4$ | | | | 0.25 | | | | |
| MgCl$_2$•6H$_2$O | | | | 10 | | | | |
| Na$_2$HPO$_4$ | | | | | | 3 | | |
| Casamino acid | | | | 0.1 | | | | |
| Proflo oil ™ (mL/L) | 4 | | | | | | 0.05 | |
| Silicon defoamer oil (mL/L) | | | | | | | 0.3 | |
| MOPS | | | | | 21 | | | |
| Trace element solution*[2] ml/L | | | | | 2 | | | |

Unless otherwise indicated all the ingredients are in g/L.
*[1]The pH is to adjusted as marked prior to the addition of CaCO$_3$.
*[2]Trace elements solution contains: ZnCl$_2$ 40 mg; FeCl$_3$6H$_2$O (200 mg); CuCl$_2$2H$_2$O (10 mg); MnCl$_2$•4H$_2$O; Na$_2$B$_4$O$_7$•10H$_2$O (10 mg); (NH$_4$)$_6$MO$_7$O$_{24}$•4H$_2$O (10 mg) per litre.

The culture media inoculated with a farnesy dibenzodiazepinone-producing microorganism may be aerated by incubating the inoculated culture media with agitation, for example, shaking on a rotary shaker, a shaking water bath, or in a fermentor. Aeration may also be achieved by the injection of air, oxygen or an appropriate gaseous mixture to the inoculated culture media during incubation. Following cultivation, the farnesyl dibenzodiazepinone compound can be extracted and isolated from the cultivated culture media by techniques known to a person skilled in the art and/or disclosed herein, including for example centrifugation, chromatography, adsorption, filtration. For example, the cultivated culture media can be optionally acidified and mixed with a suitable organic solvent such as methanol, ethanol, n-butanol, ethyl acetate, n-butyl acetate or 4-methyl-2-pentanone. The organic layer can be separated from the mycelial cake for example, by centrifugation and decantation or filtration. The mycelial cake is further optionally extracted with an organic solvent, and the organic extracts combined. The organic layer is further optionally treated, for example by: aqueous washings, precipitation, filtration and the like, followed the removal of the solvent, for example, by evaporation to dryness under vacuum. The resulting residue can optionally be reconstituted with for example water, ethyl ether, ethanol, ethyl acetate, methanol or a mixture thereof, and re-extracted in a two-phase system with a suitable organic solvent such as hexane, carbon tetrachloride, methylene chloride or a mixture thereof. After removal of the solvent, the compound can be further purified by the use of standard techniques such as normal and reverse-phase liquid chromatography, crystallization, sublimation, adsorption, mass exclusion chromatography, and the like.

B. Chemical Modifications:

The farnesyl dibenzodiazepinone Compound 1 is biosynthesized by microorganisms and isolated as described herein, and in Canadian patent 2,466,340. Compound 1 is subjected to random and/or directed chemical modifications to form compounds that are derivatives or structural analogues. Such derivatives or structural analogues having similar functional activities are within the scope of the present invention. The farnesyl dibenzodiazepinone may be modified by one or more chemical modification steps, using methods known in the art and described herein. Examples of chemical modifications procedures are also provided in Examples 4 to 9 and Example 15.

Dibenzodiazepinone analogues that are derivatives of Compound 1, for example those identified herein as the compounds of Formula I and II and their derivatives, and Compounds 2 to 130, are generated by standard organic chemistry approaches. General principles of organic chemistry required for making and manipulating the compounds described herein, including functional moieties, reactivity and common protocols are described, for example, in "Advanced Organic Chemistry," 4$^{th}$ Edition by Jerry March (1992), *Wiley*-Interscience, USA, incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protective groups, their applicability to specific functional groups and their uses are described for example in T. H. Greene and P. G. M. Wuts, *Protective Groups in Organic Synthesis*, 3$^{rd}$ Edition, John Wiley & Sons, New York (1999), incorporated herein by reference in its entirety.

Alcohols and phenols are protected with, for example: silyl ethers (TMS: trimethylsilyl, TIPS: triisopropylsilyl), acetals (MOM: methyloxymethyl, BOM: benzyloxymethyl), esters (acetate, benzoyl) and ethers (Bn: benzyl). Alcohols are deprotected by conditions such as: TBAF (tetrabutylammonium fluoride) for silyl ethers, aqueous acid catalysis for acetals and esters, saponification for esters, and hydrogenolysis for Bn and BOM. Amine is protected using standard amino acid protecting groups, for example, carbamates (such as t-butyl (BOC) and benzyl (CBZ)), fluorene derivatives (such as FMOC: N-(9-fluorenylmethoxycarbonyl)-), etc. Amine is deprotected by conditions such as: acid hydrolysis for BOC, hydrogenolysis for CBZ, or base treatment for FMOC. All protection and deprotection conditions are demonstrated in the Greene et al reference above.

Those skilled in the art will readily appreciate that many synthetic chemical processes may be used to produce derivatives of Compound 1. The following schemes are exemplary of the routine chemical modifications that may be used to produce compounds of Formula I or II. Any chemical synthetic process known to a person skilled in the art providing the structures described herein may be used and are therefore comprised in the present invention.

Scheme 1: Alcohol(s) modifications (O-alkylations and O-acylations)

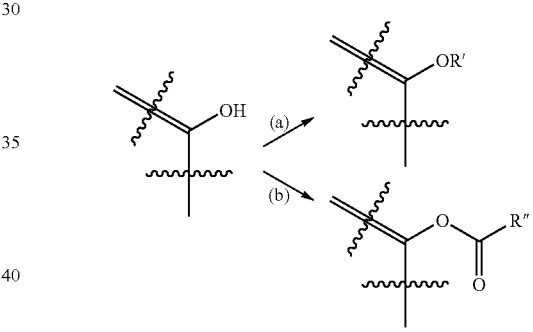

wherein, R' and R" are each selected from alkyl, alkenyl, alkynyl, cycloalkyl, heterocycloalkyl, aryl, or heteroaryl; or R"C(O)— is HC(O)— or a C-coupled amino acid.

In Scheme 1, Phenols in positions 4, 6 and 8 (for position numbers, see Example 3) are independently alkylated (to produce an ether) or acylated (to produced an ester). In Scheme 1(a), allylation is accomplished with an alkylating agent such as R'X is a diazoalkane, or with a R'X reagent, wherein X is a suitable leaving group such as Br, I and trifluoromethane sulfonate in the presence of a base, preferably, a diazoalkane is used. When R' is aryl or heteroaryl, the reaction may further need the use of a catalyst, such as copper salts (Ullman ether synthesis, Jerry March, supra). In Scheme 1(b), a phenolic alcohol is converted to ester when reacted with an activated carboxylic acid (R"C(O)X) such as an acid halide, anhydride, N-hydroxysuccinimide ester, or a carboxylic acid activated by a coupling agent (e.g.: EDC (1-(3-dimethylaminopropyl)-3-diisopropylethylcarbodiimide hydrochloride); or HATU (O-(7-azabenzotriazol-1-yl)-N,N,N',N'-tetramethyluronium hexafluorophosphate)) with a base (e.g., pyridine or N,N-diisopropylethylamine (DIPEA)) and optional acatalysts such HOBt (1-hydroxybenzotriazole hydrate) and/or DMAP (4-(dimethylamino)pyridine). The same reactions may be accomplished on alcohols formed by farnesyl modification reactions (Scheme 3).

Scheme 1 is used to obtain, for example, Compounds 4 to 12, 35 to 39 and 105 to 113 from Compound 1, and Compound 15 from Compound 13; and to produce any of the Compounds of Formula I or II comprising an O-alkyl or O-acyl group.

Scheme 2: Amine modifications (N-alkylations and N-acylations)

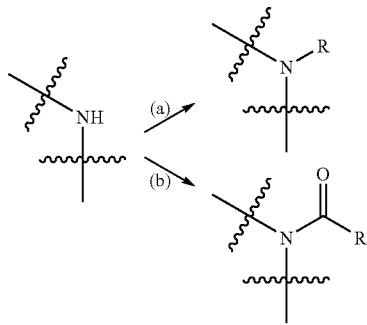

wherein, R is selected from alkyl, alkenyl, alkynyl, cycloalkyl, heterocycloalkyl, aryl, and heteroaryl; or RC(O)— is HC(O)— or a C-coupled amino acid.

In Scheme 2, amine group in position 5 (for position, see Example 3) is optionally alkylated or acylated. In Scheme 2(a), an amine is alkylated using an RX alkylating agent such as dialkyl sulfates and alkyl halides, preferably in the presence of a base (e.g., sodium bicarbonate, pyridine and the like). When R is an aryl or a heteroaryl group, the alkylation reaction with an aryl iodide may further need a catalyst, such as copper (for an example, see Plater et al. 2000, *J. Chem. Soc., Perkin Trans.* 1, 2695-2701, incorporated herein by reference in its entirety.) In Scheme 2(b), an amine is acylated when reacted with an activated carboxylic acid such as an acid halide, anhydride, N-hydroxysuccinimide ester, or a carboxylic acid activated by a coupling agent (see Scheme 1) in the presence of a base like DIPEA, and optional use of a catalyst, such as DMAP or HOBt.

Scheme 2 is used to prepare, for example, Compounds 2, 3, 13, 14, 60 to 77, 98, and 101 to 104 from Compound 1, Compound 78 from Compound 46, and Compounds 99 and 100 respectively from Compounds 42 and 45; and to produce any of the Compounds of Formula I or II comprising an N-alkyl or N-acyl group.

wherein $R^x$ and $R^y$ are each selected from H, OH and $OC_{1-6}$ alkyl, provided that at least one of $R^x$ or $R^y$ is OH; $R^z$ is selected from halogen, OH, $OC_{1-6}$alkyl, and $NHC(O)C_{1-6}$ alkyl.

In Scheme 3, double bond is modified by: (a) epoxidation; (b) epoxide ring opening (dihydroxylation, hydration, or hydroxyalkoxylation product) (c) direct dihydroxylation, hydration, or hydroxyalkoxylation; (d) hydrogenation; (e) electrophilic addition; (f) ozonolysis; (g) hydrolysis of the acetal produced in (f); and (h) reduction of the aldehyde produced in (g). In (a), epoxides are obtained from the reaction of double bonds with oxidizing agents such as peracids (e.g., mCPBA: 4-chloroperbenzoic acid). In (b), the epoxide obtained in (a) is opened by nucleophiles. In basic conditions epoxides will preferentially open to give the residual OH at the most hindered position ($R^y$). In acidic conditions, the compound having the residual OH at the $R^x$ position will be formed as the major product. In (b), the diol (dihydroxylation product: $R^x$ and $R^y$ are each OH) is obtained from hydrolysis of the epoxide in acidic or basic aqueous conditions, preferably acidic. In (b), also alcoholysis of the epoxide (hydroxyalkoxylation product) is accomplished in basic ($R^x$ is $OC_{1-6}$ alkyl and $R^y$ is OH, as major) or acidic ($R^x$ is OH and $R^y$ is $OC_{1-6}$alkyl, as major) conditions in a $C_{1-6}$alkyl alcohol as solvent, preferably acidic conditions. In (b), hydration product ($R^x$ is H and $R^y$ is OH, as the major component) is obtained from the opening of the epoxide by a hydride source (e.g. lithium aluminium hydride (LAH)). In (c), the diol ($R^x$ and $R^y$ are each OH) is obtained from the dihydroxylation of the double bond in oxidizing conditions (e.g.: osmium tetroxide, potassium permanganate, N-methylmorpholine-N-oxide, and the like). In (c), hydration product ($R^x$ is OH and $R^y$ is H, as major) is obtained from the oxidative cleavage (NaOH/hydrogen peroxide) of the intermediate formed by hydroboration of the double bond (e.g., using 9-BBN (9-borabicyclo[3,3,1]nonane), and the like). In (d), hydrogenation is carried out using a hydrogen source (e.g. hydrogen, formic acid) and a catalyst (such as rhodium, platinum, or palladium). In (e), electrophilic addition to the double bond is achieved by the formation of a carbocation from addition of a proton in acidic conditions (e.g., p-toluene sulfonic acid, alkyl sulfate/$NaHCO_3$/MeOH, and the like), and trapping of the carbocation with an alcohol ($C_{1-6}$alkyl alcohol, hydroalkoxylation), water (hydration) or another electron rich atom (e.g., an halogen or a nitrile, which is subsequently hydrolyzed to give an amide). In (f), an acetal is obtained by the reaction of the double bond with a controlled quantity of ozone and the use of a dialkyl sulfide (e.g., $Me_2S$) to decompose the ozonide at the Scheme 3: Double bond(s) modifications

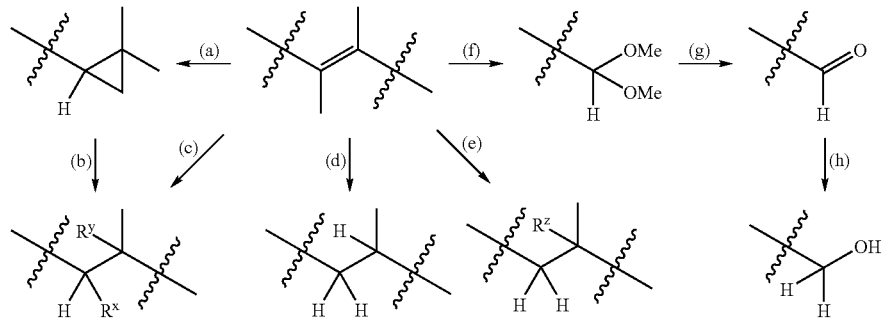

end. When the ozonolysis is done in an alcohol, e.g. methanol, the dialkyl acetal is obtained. In (g), an aldehyde is obtained by the hydrolysis of the acetal obtained in (f). In (h), the aldehyde obtained from (g) is reduced to alcohol by a reducing agent [H] such as sodium borohydride (NaBH$_4$), sodium cyanoborohydride (NaBH$_3$CN) or LAH.

Scheme 3 is used to obtain, for example: in (a) Compounds 16 from Compound 1, and Compounds 23, 24 and 26 from Compound 42, Compounds 25, 27 and 29 from Compound 41, Compounds 28, 30 and 31 from Compound 40, and Compounds 32, 33 and 34 respectively from Compounds 45, 44 and 43; in (b) Compounds 53 to 59 respectively from Compounds 16 to 22; in (c) Compounds 53 to 59 from Compound 1; in (d) Compounds 40 to 46 from Compound 1, and Compounds 78, 99 and 100 from Compound 2; in (e) Compounds 79 to 81 from Compound 2, Compounds 82 to 84 and 88 to 93 from Compound 1, Compounds 85 to 87 from Compound 14; in (f) Compounds 94 to 96 from Compound 1; in (g) Compounds 47, 49 and 51 from Compound 1; and in (h) Compounds 48, 50 and 52 respectively from Compounds 47, 49 and 51. Schemes 3 (a)-(g) are also used to produce any Compound of Formula I or II comprising a modified farnesyl group.

Scheme 4: Aromatic substitutions

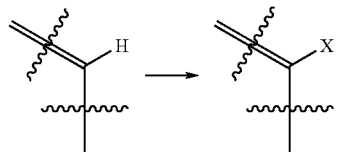

wherein, X is selected from F, Cl, Br and I.

In Scheme 4, the aryl group is modified (when one of $X^1$ to $X^5$ is halo in Formula I or II) by aromatic substitutions, such as halogenation, including bromination, chlorination, fluorination, and iodination. Halogenating agents include bromine, N-haloamides (e.g, N-bromosuccinimide (NBS), tetraalkylammonium polyhalides), chlorine, chlorinated cyclohexadienes, N-chloroamines, chlorodimethylsulfonium chloride, sulfur monochloride/aluminum chloride/thionyl chloride, iodine chloride, iodine/oxidizing agent (e.g, nitric acid, iodic acid, sulfur trioxide, etc), silver(II) fluoride, cesium fluoroxysulfate, and the like.

Scheme 4 is used to prepare, for example, Compound 97 from Compound 1 and Compound 123 from Compound 78; and to produce any of the Compounds of Formula I or II comprising a halogen group on the aromatic ring.

Prodrugs are prepared by routine chemical modifications such as described in Jerry March, supra, including esterification and alkylation reactions, i.e., use of activated acids or mixed anhydrides (acyl halides, use of coupling reagents, etc), and by the use of alkylating agents (R—X, wherein X is a leaving group, such as diazo, and R is the desired group). Phosphate prodrugs are prepared by phosphorylation, for example, by a procedure such as described in U.S. Pat. No. 5,561,122 (Pettit et al) and in Hwang and Cole (2004), *Org. Lett.*, vol 6, no 10, 1555-1556 ((POM)$_2$phosphate triester from (POM)$_2$phosphoryl chloride), the content of which is incorporated herein by reference in their entirety.

IV. PHARMACEUTICAL COMPOSITIONS COMPRISING THE COMPOUNDS OF THE INVENTION

The invention provides a pharmaceutical composition comprising a compound of Formula I, or a pharmaceutically acceptable salt, solvate or prodrug thereof, in combination with a pharmaceutically acceptable carrier. The pharmaceutical composition comprising a dibenzodiazepinone analogue is useful for treating diseases and disorders associated with uncontrolled cellular growth and proliferation, such as a neoplastic condition. The pharmaceutical composition is also useful in treating other diseases and disorders, including inflammation, autoimmune diseases, infections, neurodegenerative diseases and stress. The pharmaceutical composition comprising a dibenzodiazepinone analogue may be packaged into a convenient commercial package providing the necessary materials, such as the pharmaceutical composition and written instructions for its use in treating a neoplastic condition, in a suitable container.

The compounds of the present invention, or pharmaceutically acceptable salts, solvates or prodrugs thereof, can be formulated for oral, sublingual, intranasal, intraocular, rectal, transdermal, mucosal, topical or parenteral administration for the therapeutic or prophylactic treatment of neoplastic and proliferative diseases and disorders. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracerebral or intracranial, intraspinal, intracisternal, and intrathecal (spinal fluids). Any known device useful for parenteral injection or infusion of drug formulations can be used to effect such administration. For oral and/or parental administration, compounds of the present invention can be mixed with conventional pharmaceutical carriers and excipients and used in the form of solutions, emulsions, tablets, capsules, soft gels, elixirs, suspensions, syrups, wafers and the like. The compositions comprising a compound of the present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate cancer. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various agents for human therapy).

As used herein, the term "unit dosage" refers to physically discrete units suitable as unitary dosages for human subjects and other mammals, each unit containing a predetermined quantity of dibenzodiazepinone analogue calculated to produce the desired therapeutic effect, in association with a suitable pharmaceutically acceptable carriers. In one embodiment, the unit dosage contains from 10 to 3000 mg of active ingredient. In another embodiment, the unit dosage contains 20 to 1000 mg of active ingredient. The compositions of the present invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. Nos.

4,452,775 (issued to Kent), 5,039,660 (issued to Leonard), and 3,854,480 (issued to Zaffaroni), incorporated herein by reference in their entirety.

The pharmaceutically-acceptable compositions of the present invention comprise one or more compounds of the present invention in association with one or more non-toxic, pharmaceutically-acceptable carriers and/or diluents and/or adjuvants and/or excipients, collectively referred to herein as "carrier" materials, and if desired other active ingredients. Pharmaceutically acceptable carriers include, for example, solvents, vehicles or medium such as saline, buffered saline, dextrose, water, glycerol, ethanol, propylene glycol, polysorbate 80 (Tween-80™), poly(ethylene)glycol 300 and 400 (PEG 300 and 400), PEGylated castor oil (E.g. Cremophor EL), poloxamer 407 and 188, hydrophobic carriers, and combinations thereof. Hydrophobic carriers include, for example, fat emulsions, lipids, PEGylated phopholids, polymer matrices, biocompatible polymers, liposheres, vesicles, particles, and liposomes. The term specifically excludes cell culture medium.

Excipients or additives included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Formulations for parenteral administration can be in the form of aqueous or non-aqueous isotonic sterile injection solutions, suspensions or fat emulsions, comprising a compound of this invention, or a pharmaceutically acceptable salt or prodrug thereof. The parenteral form used for injection must be fluid to the extent that easy syringability exists. These solutions or suspensions can be prepared from sterile concentrated liquids, powders or granules. The compounds can be dissolved in a carrier such as a solvent or vehicle, for example, polyethylene glycol, propylene glycol, ethanol, corn oil, benzyl alcohol, glycofurol, N,N-dimethylacetamide, N-methylpyrrolidone, glycerine, saline, dextrose, water, glycerol, hydrophobic carriers, and combinations thereof.

Excipients used in parenteral preparations also include, without limitation, stabilizing agents (e.g. carbohydrates, amino acids and polysorbates), solubilizing agents (e.g. cetrimide, sodium docusate, glyceryl monooleate, polyvinylpyrolidone (PVP) and polyethylene glycol (PEG)) and surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, liposheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of the compound can be a ready-to-use solution of the compound in a suitable carrier in sterile, hermetically sealed ampoules or in sterile pre-loaded syringes. The suitable carrier optionally comprises any of the above-mentioned excipients.

Alternatively, the unit dosage of the compound of the present invention can be in a concentrated liquid, powder or granular form for ex tempore reconstitution in the appropriate pharmaceutically acceptable carrier at the time of delivery. In addition the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

For example, in intravenous (IV) use, a sterile formulation of the compound of formula I and optionally one or more additives, including solubilizers or surfactants, can be dissolved or suspended in any of the commonly used intravenous fluids and administered by infusion. Intravenous fluids include, without limitation, physiological saline, phosphate buffered saline, 5% glucose or Ringer's™ solution.

In another example, in intramuscular preparations, a sterile formulation of the compound of the present invention or suitable soluble salts or prodrugs forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

The oral pharmaceutical composition is preferably made in the form of a unit dosage containing a therapeutically-effective amount of the active ingredient. Examples of such dosage units are tablets and capsules. For therapeutic purposes, the tablets and capsules which can contain, in addition to the active ingredient, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Providone), sorbitol, or tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), lubricants or lubricating agents (e.g., magnesium stearate or other metallic stearates, stearic acid, polyethylene glycol, waxes, oils, silica and colloical silica, silicon fluid or talc), disintegrants or disintegrating agents (e.g., potato starch, corn starch and alginic acid), flavouring, coloring agents, or acceptable wetting agents. Carriers may also include coating excipients such as glyceryl monostearate or glyceryl distearate, to delay absorption in the gastrointestinal tract.

Oral liquid preparations, generally in the form of aqueous or oily solutions, suspensions, emulsions, syrups or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For both liquid and solid oral preparations, flavoring agents such as peppermint, oil of wintergreen, cherry, grape, fruit flavoring or the like can also be used. It may also be desirable to add a coloring agent to make the dosage form more aesthetic in appearance or to help identify the product. For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For application to the eyes or ears, the compounds of the present invention can be presented in liquid or semi-liquid form formulated in hydrophobic or hydrophilic bases as ointments, creams, lotions, paints or powders. For rectal administration the compounds of the present invention can be administered in the form of suppositories admixed with conventional carriers such as cocoa butter, wax or other glyceride.

V. MEDICAL USE IN THE TREATMENT OF NEOPLASMS

In one aspect, the invention relates to a method for inhibiting growth and/or proliferation of cancer cells in a mammal. In another aspect, the invention provides a method for treating neoplasms in a mammal. Mammals include ungulates (e.g. sheeps, goats, cows, horses, pigs), and non-ungulates, including rodents, felines, canines and primates (i.e. human and non-human primates). In a preferred embodiment, the mammal is a human.

The dibenzodiazepinone analogues of the present invention may bind to or interact with other cancer-associated proteins and polypeptides, including, without limitation, polypeptides encoded by oncogenes, polypeptides that induce angiogenesis, proteins involved in metastasizing and/ or invasive processes, and proteases that regulate apoptosis and the cell cycle. Regardless of the mechanism of action, the dibenzodiazepinone analogues of the invention have been demonstrated to exhibit anti-cancer activity both in vitro and in vivo. Based on these discoveries, applicants have developed methods for treating neoplasms.

As used herein, the terms "neoplasm", "neoplastic disorder", "neoplasia" "cancer," "tumor" and "proliferative disorder" refer to cells having the capacity for autonomous growth, i.e., an abnormal state of condition characterized by rapidly proliferating cell growth which generally forms a distinct mass that show partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

The dibenzodiazepinone analogue is brought into contact with or introduced into a cancerous cell or tissue. In general, the methods of the invention for delivering the compositions of the invention in vivo utilize art-recognized protocols for delivering therapeutic agents with the only substantial procedural modification being the substitution of the dibenzodiazepinone analogue of the present invention for the therapeutic agent in the art-recognized protocols. The route by which the dibenzodiazepinone analogue is administered, as well as the formulation, carrier or vehicle will depend on the location as well as the type of the neoplasm. A wide variety of administration routes can be employed. The dibenzodiazepinone analogue may be administered by intravenous or intraperitoneal infusion or injection. For example, for a solid neoplasm that is accessible, the compound of the invention may be administered by injection directly into the neoplasm. For a hematopoietic neoplasm the compound may be administered intravenously or intravascularly. For neoplasms that are not easily accessible within the body, such as metastases or brain tumors, the compound may be administered in a manner such that it can be transported systemically through the body of the mammal and thereby reach the neoplasm and distant metastases for example intrathecally, intravenously or intramuscularly or orally. Alternatively, the compound can be administered directly to the tumor. The compound can also be administered subcutaneously, intraperitoneally, topically (for example for melanoma), rectally (for example colorectal neoplasm) vaginally (for example for cervical or vaginal neoplasm), nasally or by inhalation spray (for example for lung neoplasm).

The dibenzodiazepinone analogue is administered in an amount that is sufficient to inhibit the growth or proliferation of a neoplastic cell, or to treat a neoplastic disorder. The term "inhibition" refers to suppression, killing, stasis, or destruction of cancer cells. The inhibition of mammalian cancer cell growth according to this method can be monitored in several ways. Cancer cells grown in vitro can be treated with the compound and monitored for growth or death relative to the same cells cultured in the absence of the compound. A cessation of growth or a slowing of the growth rate (i.e., the doubling rate), e.g., by 50% or more at 100 micromolar, is indicative of cancer cell inhibition (see Anticancer Drug Development Guide: preclinical screening, clinical trials and approval; B. A. Teicher and P. A. Andrews, ed., 2004, Humana Press, Totowa, N.J.). Alternatively, cancer cell inhibition can be monitored by administering the compound to an animal model of the cancer of interest. Examples of experimental non-human animal cancer models are known in the art and described below and in the examples herein. A cessation of tumor growth (i.e., no further increase in size) or a reduction in tumor size (i.e., tumor volume by least a 58%) in animals treated with the compound relative to tumors in control animals not treated with the compound is indicative of significant tumor growth inhibition (see Anticancer Drug Development Guide: preclinical screening, clinical trials and approval; B. A. Teicher and P. A. Andrews, ed., 2004, Humana Press, Totowa, N.J.).

The term "treatment" refers to the application or administration of a dibenzodiazepinone analogue to a mammal, or application or administration of a dibenzodiazepinone analogue to an isolated tissue or cell line from a mammal, who has a neoplastic disorder, a symptom of a neoplastic disorder or a predisposition toward a neoplastic disorder, with the purpose to cure, heal, alleviate, relieve, alter, ameliorate, improve, or control the disorder, the symptoms of disorder, or the predisposition toward disorder. The term "treating" is defined as administering, to a mammal, an amount of a dibenzodiazepinone analogue sufficient to result in the prevention, reduction or elimination of neoplastic cells in a mammal ("therapeutically effective amount"). The therapeutically effective amount and timing of dosage will be determined on an individual basis and may be based, at least in part, on consideration of the age, body weight, sex, diet and general health of the recipient subject, on the nature and severity of the disease condition, and on previous treatments and other diseases present. Other factors also include the route and frequency of administration, the activity of the administered compound, the metabolic stability, length of action and excretion of the compound, drug combination, the tolerance of the recipient subject to the compound and the type of neoplasm or proliferative disorder. In one embodiment, a therapeutically effective amount of the compound is in the range of about 0.01 to about 750 mg/kg of body weight of the mammal. In another embodiment, the therapeutically effective amount is in the range of about 0.01 to about 300 mg/kg body weight per day. In yet another embodiment, the therapeutically effective amount is in the range of 10 to about 50 mg/kg body weight per day. The therapeutically effective doses of the above embodiments may also be expressed in milligrams per square meter ($mg/m^2$) in the case of a human patient. Conversion factors for different mammalian species may be found in: Freireich et al, Quantitative comparison of toxicity of anticancer agents in mouse, rat, dog, monkey and man, *Cancer Chemoth. Report,* 1966, 50(4): 219-244, incorporated herein by reference in its entirety. When special requirements may be needed (e.g. for children patients), the therapeutically effective doses described above may be outside the ranges stated herein. Such higher or lower doses are within the scope of the present invention.

To monitor the efficacy of tumor treatment in a human, tumor size and/or tumor morphology is measured before and after initiation of the treatment, and treatment is considered effective if either the tumor size ceases further growth, or if the tumor is reduced in size, e.g., by at least 10% or more (e.g., 20%, 30%, 40%, 50%, 60%, 70%, 80%, 90% or even 100%, that is, the absence of the tumor). Prolongation of survival, time-to-disease progression, partial response and objective response rate are surrogate measures of clinical activity of the investigational agent. Tumor shrinkage is considered to be one treatment-specific response. This system is limited by the requirement that patients have visceral masses that are amenable to accurate measurement. Methods of determining the size of a tumor in vivo vary with the type of tumor, and include, for example, various imaging techniques well known to those in the medical imaging or oncology fields (MRI, CAT, PET, etc.), as well as histological techniques and flow cytometry. For certain types of cancer, evaluation of serum tumor markers are also used to evaluate response (eg prostate-specific antigen (PSA) for prostate cancer, and carcino-embryonic antigen (CEA), for colon cancer). Other methods of monitoring cancer growth include cell counts (e.g. in leukemias) in blood or relief in bone pain (e.g. prostate cancer).

The dibenzodiazepinone compound may be administered once daily, or the compound may be administered as two, three, four, or more sub-doses at appropriate intervals throughout the day. In that case, the dibenzodiazepinone compound contained in each sub-dose must be correspondingly smaller in order to achieve the total daily dosage. The dosage unit can also be compounded for delivery over several days, e.g., using a conventional sustained release formulation which provides sustained release of the dibenzodiazepinone compound over a several day period. Sustained release formulations are well known in the art. In this embodiment, the dosage unit contains a corresponding multiple of the daily dose. The effective dose can be administered either as a single administration event (e.g., a bolus injection) or as a slow injection or infusion, e.g. over 30 minutes to about 24 hours. The compound may be administered as a treatment, for up to 30 days. Moreover, treatment of a subject with a therapeutically effective amount of a composition can include a single treatment or a series of treatments (e.g., a four-week treatment repeated 3 times, with a 2 months interval between each treatment). Estimates of effective dosages, toxicities and in vivo half-lives for the dibenzodiazepinone compounds encompassed by the invention can be made using conventional methodologies or on the basis of in vivo testing using an appropriate animal model.

The dibenzodiazepinone compound may be administered in conjunction with or in addition to other known anticancer treatments such as surgery, radiotherapy, or other known anticancer compounds or chemotherapeutic agents. Such agents include, but are not limited to, 5-fluorouracil, mitomycin C, methotrexate, hydroxyurea, nitrosoureas (e.g., BCNU, CCNU), cyclophosphamide, procarbazine, dacarbazine, thiotepa, atreptozocine, temozolomide, enzastaurin, erlotinib, mitoxantrone, anthracyclins (Epirubicin and Doxurubicin), CPT-11, camptothecin and derivatives thereof, etoposide, navelbine, vinblastine, vincristine, pregnasone, platinum compounds such as carboplatin and cisplatin, taxanes such as taxol and taxotere; hormone therapies such as tamoxifen and anti-estrogens; antibodies to receptors, such as herceptin and Iressa; aromatase inhibitors, progestational agents and LHRH analogs; biological response modifiers such as IL2 and interferons; multidrug reversing agents such as the cyclosporin analog PSC 833. (For more examples, see: *The Merck Index,* $12^{th}$ edition (1996), Therapeutic Category and Biological Activity Index, lists under "Antineoplastic" sections.

Toxicity and therapeutic efficacy of dibenzodiazepinone compounds can be determined by standard pharmaceutical procedures in cell cultures or experimental animals. Therapeutic efficacy is determined in animal models as described above and in the examples herein. Toxicity studies are done to determine the lethal dose for 10% of tested animals (LD10). Animals are treated at the maximum tolerated dose (MTD): the highest dose not producing mortality or greater than 20% body weight loss. The effective dose (ED) is related to the MTD in a given tumor model to determine the therapeutic index of the compound. A therapeutic index (MTD/ED) close to 1.0 has been found to be acceptable for some chemotherapeutic drugs, a preferred therapeutic index for classical chemotherapeutic drugs is 1.25 or higher.

The data obtained from cell culture assays and animal studies can be used in formulating a range of dosage for use in humans. The dosage of compositions of the invention will generally be within a range of circulating concentrations that include the MTD. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound. Such information can be used to more accurately determine useful doses in humans. Levels in plasma may be measured, for example, by HPLC.

Animal models to determine antitumor efficacy of a compound are generally carried out in mice. Either murine tumor cells are inoculated subcutaneously into the hind flank of mice from the same species (syngeneic models) or human tumor cells are inoculated subcutaneously into the hind flank of severe combined immune deficient (SCID) mice or other immune deficient mice (nude mice) (xenograft models).

Advances in mouse genetics have generated a number of mouse models for the study of various human diseases including cancer. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dibenzodiazepinone compounds, as well as for determining a therapeutically effective dose.

In addition to the compounds of the invention, pharmaceutically acceptable salts, solvates or prodrugs of said compounds may also be employed in compositions to treat or prevent the above-identified disorders.

EXAMPLES

Unless otherwise noted, all reagents were purchased from Sigma Chemical Co. (St. Louis, Mo.), Aldrich.

All NMR spectra were collected in deuterated solvent on a Varian 500™ Spectrometer ($^1$H NMR at 500 MHz, $^{13}$C NMR at 125 MHz). UV and mass spectra were collected by Waters 2690™ HPLC using a photodiode array detector (PDA, 210-400 nm) coupled to a Waters Micromass™ ZQ™ mass detector.

Unless otherwise indicated, all numbers expressing quantities of ingredients, properties such as molecular weight, reaction conditions, molar equivalents (eq), percentage of binding and/or inhibition, $GI_{50}$, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

In the following section, examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperature, solvent and/or reagents could increase the yields.

In addition, the materials, methods, and examples, including in vitro and in vivo efficacy, bioavailability, toxicity and pharmacological properties are illustrative only and not intended to be limiting. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

Example 1

Production of Compound 1 by Fermentation

Exemplary Fermentation Procedures:

a) Fermentation Procedure

*Micromonospora* sp. (deposit accession number IDAC 070303-01) was maintained on agar plates of ISP2 agar (Difco Laboratories, Detroit, Mich.). An inoculum for the production phase was prepared by transferring the surface growth of the *Micromonospora* sp. from the agar plates to 125-mL flasks containing 25 mL of sterile medium comprised of glucose 10 g, potato dextrin type IV (Sigma) 20 g, yeast extract 5 g, N Z Amine-A 5 g, 1 g $CaCO_3$ made up to one liter with tap water (pH 7.0). The culture was incubated at about 28° C. for approximately 70-72 hours on a rotary shaker set at 250 rpm. Following incubation, 10 mL of culture was transferred to a 2 L baffled flask containing 600 mL of sterile production medium containing 20 g/L potato dextrin type IV (sigma), 30 g/L glycerol, 2.5 g/L Bacto-peptone, 8.34 g/L yeast extract, 3 g/L $CaCO_3$, pH 7.0. Fermentation broth was prepared by incubating the production culture at 28° C. in a rotary shaker set at 250 rpm for 5 days.

b) Alternate Procedure:

The fermentation was accomplished as a 1×10 L batch in a 14.5 L fermentor (BioFlo 110™ Fermentor, New Brunswick Scientific, Edison, N.J., USA) using an improved procedure described in CA patent application 2,466,340, filed Jan. 21, 2004.

*Micromonospora* sp. (deposit accession number IDAC 070303-01) was maintained on agar plates of ISP2 agar (Difco Laboratories, Detroit, Mich.). An inoculum for the production phase was prepared by transferring the surface growth of the *Micromonospora* sp. from the agar plates to 2-L flasks containing 500 mL of sterile medium comprised of 10 g glucose, 20 g potato dextrin, 5 g yeast extract, 5 g NZ-Amine A, and 1 g $CaCO_3$ made up to one liter with tap water (pH 7.0). The culture was incubated at about 28° C. for approximately 70 hours on a rotary shaker set at 250 rpm. Following incubation, 300 mL of culture was transferred to a 14.5 L fermentor containing 10 L of sterile production medium. Each liter of production medium was composed of 20 g potato dextrin, 30 g glycerol, 2.5 g Bacto-peptone, 8.34 g yeast extract, 0.3 mL Silicone defoamer oil (Chem Service), 0.05 ml Proflo Oil™ (Traders protein) and 3 g $CaCO_3$ made to one liter with distilled water and adjusted to pH 7.0. The culture was incubated at 28° C., with dissolved oxygen ($dO_2$) controlled at 25% in a cascade loop with agitation varied between 320-600 RPM and aeration set at a fixed rate of 0.5 v/v/m.

In addition to the above medium, other preferred media for the production of Compound 1 by fermentation are provided in Table 1 (QB, MA, KH, RM, JA, FA, CL). Any one of *Micromonospora* sp. 046-ECO11 or [S01]046 may be used in these exemplified methods.

Example 2

Isolation of Compound 1

Exemplary Isolation Procedures:

a) Isolation Procedure 1:

500 mL ethyl acetate was added to 500 mL of fermentation broth prepared as described in Example 1 above. The mixture was agitated for 30 minutes on an orbital shaker at 200 rpm to create an emulsion. The phases were separated by centrifugation and decantation. Between 4 and 5 g of anhydrous $MgSO_4$ was added to the organic phase, which was then filtered and the solvents removed in vacuo.

An ethyl acetate extract from 2 L fermentation was mixed with HP-20 resin (100 mL; Mitsubishi Casei Corp., Tokyo, Japan) in water (300 mL). Ethyl acetate was removed in vacuo, the resin was filtered on a Buchner funnel and the filtrate was discarded. The adsorbed HP-20 resin was then washed successively with 2×125 mL of 50% acetonitrile in water, 2×125 mL of 75% acetonitrile in water and 2×125 mL of acetonitrile.

Fractions containing Compound 1 were evaporated to dryness and 100 mg was digested in the 5 mL of the upper phase of a mixture prepared from chloroform, cyclohexane, methanol, and water in the ratios, by volume, of 5:2:10:5. The sample was subjected to centrifugal partition chromatography using a High Speed Countercurrent Chromatography (HSCC) system (Kromaton Technologies, Angers, France) fitted with a 200 mL cartridge and prepacked with the upper phase of this two-phase system. The HSCC was run with the lower phase mobile and Compound 1 was eluted at approximately one-half column volume. Fractions were collected and Compound 1 was detected by TLC of aliquots of the fractions on commercial Kieselgel $60F_{254}$ plates. Compound could be visualized by inspection of dried plates under UV light or by spraying the plates with a spray containing vanillin (0.75%) and concentrated sulfuric acid (1.5%, v/v) in ethanol and subsequently heating the plate. Fractions contained substantially pure Compound 1, although highly colored. A buff-colored sample could be obtained by chromatography on HPLC as follows.

6 mg of sample was dissolved in acetonitrile and injected onto a preparative HPLC column (Xterra™ ODS (10 µm), 19×150 mm, Waters Co., Milford, Mass.), with a 9 mL/min flow rate and UV peak detection at 300 nm. The column was eluted with acetonitrile/buffer (5 mM of $NH_4HCO_3$) according to the following gradient shown in Table 2.

TABLE 2

| Preparative HPLC gradient | | |
|---|---|---|
| Time (min) | Water (%) | Acetonitrile (%) |
| 0 | 50 | 50 |
| 10 | 0 | 100 |
| 20 | 0 | 100 |
| 25 | 50 | 50 |
| 30 | 50 | 50 |

Fractions containing Compound 1 were combined, concentrated and lyophilized to give a yield of 3.8 mg compound.

b) Isolation Procedure 2:

Compound 1 was also isolated using the following alternative protocol. At the end of the incubation period, the fermentation broth from the baffled flasks of Example 1 was centrifuged and the supernatant decanted from the pellet containing the bacterial mycelia. 100 mL of 100% MeOH was added to the mycelial pellet and the sample was stirred for 10 minutes and centrifuged for 15 minutes. The methanolic supernatant was decanted and saved. 100 mL of acetone was then added to the mycelial pellet and stirred for 10 minutes then centrifuged for 15 minutes. The acetonic supernatant was decanted and combined with the methanolic supernatant. Finally, 100 mL of 20% MeOH/$H_2O$ was added to the mycelial pellet, stirred for 10 minutes and centrifuged for 15 minutes. The supernatant was combined with the acetonic and methanolic supernatants.

The combined supernatant was added to 400 ml of HP-20 resin in 1000 mL of water and the organics were removed in vacuo. The resulting slurry was filtered on a Buchner funnel and the filtrate was discarded. HP-20 resin was washed successively with 2×500 mL of 50% MeOH/$H_2O$, 2×500 mL of 75% MeOH/$H_2O$ and 2×500 mL of MeOH.

The individual washes were collected separately and analyzed by TLC as described above. Those fractions containing Compound 1 were evaporated to near dryness and lyophilized. The lyophilizate was dissolved in methanol and injected onto a preparative HPLC column (Xterra™ ODS (10 µm), 19×150 mm, Waters Co., Milford, Mass.) with a flow rate of 9 mL/min and peak detection at 300 nm.

The column was eluted with acetonitrile/buffer (5 mM of $NH_4HCO_3$) according to gradient shown in Table 3.

TABLE 3

| Preparative HPLC gradient | | |
|---|---|---|
| Time (min) | Buffer (%) | Acetonitrile (%) |
| 0 | 95 | 5 |
| 15 | 45 | 55 |
| 20 | 5 | 95 |
| 30 | 5 | 95 |
| 35 | 95 | 5 |

Fractions containing Compound 1 were combined, concentrated and lyophilized to yield about 33.7 mg of compound.

c) Isolation Procedure 3:

10 liters of the whole broth from Example 1 was extracted twice with equal volumes of ethyl acetate and the two extracts were combined and concentrated to dryness. The dried extract was weighed, and for every gram of dry extract, 100 mL of MeOH—H$_2$O (2:1 v/v) and 100 mL of hexane was added. The mixture was swirled gently but well to achieve dissolution. The two layers were separated and the aqueous layer is washed with 100 mL of hexane. The two hexane layers were combined and the combined hexane solution was washed with 100 mL methanol:water (2:1, v/v). The two methanol:water layers were combined and treated with 200 mL of EtOAc and 400 mL of water. The layers were separated and the aqueous layer extracted twice further with 200 mL portions of EtOAc. The EtOAc layers are combined and concentrated. The residue obtained (220 mg) was suitable for final purification, either by HSCC or by HPLC as described above. This extraction process achieved a ten-fold purification when compared with the extraction protocol used in (a) or (b).

Example 3

Elucidation of the Structure of Compound 1

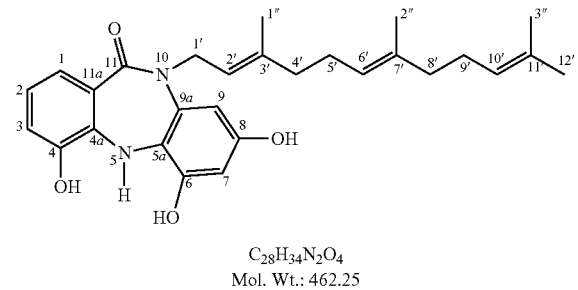

C$_{28}$H$_{34}$N$_2$O$_4$
Mol. Wt.: 462.25

The calculated molecular weight of the major isotope (462.25) and formula (C$_{28}$H$_{34}$N$_2$O$_4$) of Compound 1 was confirmed by mass spectral analysis: negative ionization gave an (M–H)$^-$ molecular ion of 461.2 and positive ionization gave an (M+H)$^+$ molecular ion of 463.3. UVmax was determined to be 230 nm with a shoulder at 290 nm.

Proton and carbon NMR spectral analysis is shown in Table 4. NMR data were collected dissolved in MeOH-d4 including proton, carbon and multidimensional pulse sequences gDQ-COSY, gHSQC, gHMBC, and NOESY. A number of cross peaks in the 2D spectra of Compound 1 are key in the structural determination. For example, the farnesyl chain is placed on the amide nitrogen by a strong cross peak between the proton signal of the terminal methylene of that chain at 4.52 ppm and the amide carbonyl carbon at 170 ppm in the gHMBC experiment. This conclusion is confirmed by a cross peak in the NOESY spectrum between the same methylene signals at 4.52 ppm and the aromatic proton signal at 6.25 ppm from one of the two protons of the tetra substituted benzenoid ring. Assignment of proton and carbon signals are shown in Table 4.

TABLE 4

$^1$H and $^{13}$C NMR ($\delta_H$, ppm) Data of Compound 1 in MeOH-D$_4$

| Assignment | $^1$H | $^{13}$C | Group |
|---|---|---|---|
| 1 | 7.15 | 122.3 | CH |
| 2 | 6.74 | 121.0 | CH |
| 3 | 6.83 | 116.9 | CH |
| 4 | — | 146.0 | C—OH |
| 4a | — | 142.0 | C |
| 5a | — | 126.0 | C |
| 6 | — | 148.2 | C—OH |
| 7 | 6.20 | 100.0 | CH |
| 8 | — | 153.0 | C—OH |
| 9 | 6.25 | 101.0 | CH |
| 9a | — | 135.0 | C |
| 11 | — | 170.0 | C(O) |
| 11a | — | 125.0 | C |
| 1' | 4.52 | 48.7 | CH$_2$ |
| 2' | 5.35 | 121.1 | CH |
| 3' | — | 138.5 | C |
| 4' | 2.03 | 39.5 | CH$_2$ |
| 5' | 2.08 | 26.7 | CH$_2$ |
| 6' | 5.09 | 124.1 | CH |
| 7' | — | 135.0 | C |
| 8' | 1.95 | 39.6 | CH$_2$ |
| 9' | 2.02 | 26.3 | CH$_2$ |
| 10' | 5.06 | 124.4 | CH |
| 11' | — | 130.9 | C |
| 12' | 1.64 | 24.8 | CH$_3$ |
| 1" | 1.72 | 15.5 | CH$_3$ |
| 2" | 1.59 | 14.9 | CH$_3$ |
| 3" | 1.55 | 16.5 | CH$_3$ |

Based on the mass, UV and NMR spectroscopy data, the structure of the compound was determined to be the structure of Compound 1 shown above.

Example 4

Dialkylsulfate Reactions a) Synthesis and Structural Elucidation of Compounds 2 and 80

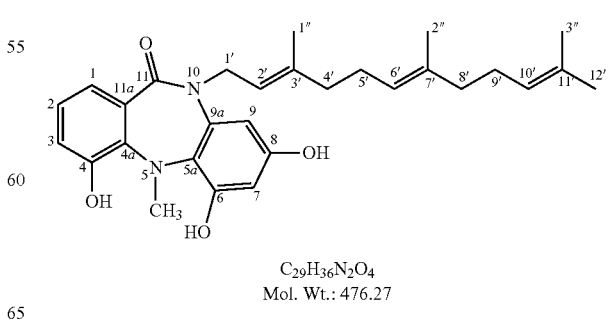

C$_{29}$H$_{36}$N$_2$O$_4$
Mol. Wt.: 476.27

Compound 2, namely 10-farnesyl-4,6,8-trihydroxy-5-methyl-5,10-dihydro-dibenzo[b,e][1,4]diazepin-11-one, and

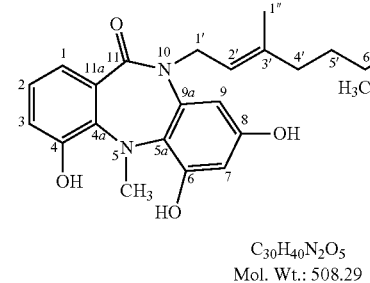

C$_{30}$H$_{40}$N$_2$O$_5$
Mol. Wt.: 508.29

Compound 80, namely 10-(7-methoxy-3,7,11-trimethyl-dodeca-2,10-dienyl)-4,6,8-trihydroxy-5-methyl-5,10-dihydro-dibenzo[b,e][1,4]diazepin-11-one, were prepared and identified as follows:

Preparation:

Compound 1 (500.0 mg) was dissolved in methanol (MeOH, 20 mL) and stirred with dimethyl sulfate (0.5 mL) and NaHCO$_3$ (250 mg) at room temperature for 48 hrs. The reaction mixture was diluted to 200 mL by adding water and extracted with ethyl acetate (EtOAc, 300 mL×3). The organic layer was separated and dried under vacuum, re-dissolved in MeOH and filtered through a 0.45 μm 13 mm Acrodisc™ GHP syringe filter. The filtrate was subjected for isolation on a Waters HPLC coupled to a photodiode array detector. Compound 80 (12.1 mg) and Compound 2 (308.5 mg) were isolated by the multiple injections on Nova-Pack™ HR 6 μm C18 25×200 mm column (20 mL/min, H$_2$O/CH$_3$CN gradient 80:20-30:70, 0-8 min; 30:70-0:100, 8-18 min), eluting at 14.5 and 16.8 min, respectively.

Structural Elucidation of Compounds 2 and 80:

The calculated molecular weight for the major isotope (476.27) and formula (C$_{29}$H$_{36}$N$_2$O$_4$) of Compound 2 was confirmed by mass spectral analysis: negative ionization gave an (M−H)$^−$ molecular ion of 475.6 and positive ionization gave an (M+Na)$^+$ molecular ion of 499.4. Proton and carbon NMR spectral analysis is shown in Table 5. Signals were easily assigned based on Compound 1 structure knowledge. The calculated molecular weight for the major isotope (508.29) and formula (C$_{30}$H$_{40}$N$_2$O$_5$) of Compound 80 was confirmed by mass spectral analysis: negative ionization gave an (M−H)$^−$ molecular ion of 507.3 and positive ionization gave an (M+H)$^+$ molecular ion of 509.3. The characteristic N-methyl (signal 5), methoxy (signal 7'-OMe) and the methylene group (6'), from the addition of methanol on the farnesyl chain were easily assigned as shown in Table 5.

TABLE 5

NMR (δ, ppm) Data of Compounds 2 and 80 in MeOH-D$_4$

| Assignment | Compound 2 $^1$H | Compound 2 $^{13}$C | Compound 80 $^1$H | Group |
|---|---|---|---|---|
| 1 | 7.21 | 122.1 | 7.21 | CH |
| 2 | 7.14 | 127.3 | 7.14 | CH |
| 3 | 7.02 | 118.4 | 7.02 | CH |
| 4 | — | 152.6 | — | C—OH |
| 4a | — | 139.3 | — | C |
| 5-N—Me | 2.92 | 41.1 | 2.93 | N—CH$_3$ |
| 5a | — | 125.4 | — | C |
| 6 | — | 154.8 | — | C—OH |
| 7 | 6.22 | 99.6 | 6.20 | CH |
| 8 | — | 156.8 | — | C—OH |
| 9 | 6.34 | 101.4 | 6.34 | CH |
| 9a | — | 142.0 | — | C |
| 11 | — | 168.2 | — | C(O) |
| 11a | — | 133.5 | — | C |
| 1' | 4.83, 4.58 | 47.7 | 4.89, 4.57 | CH$_2$ |
| 2' | 5.44 | 119.8 | 5.42 | CH |
| 3' | — | 139.3 | — | C |
| 4' | 2.07$^b$ | 39.5 | 2.06 | CH$_2$ |
| 5' | 2.12$^b$ | 26.2 | 1.42 | CH$_2$ |
| 6' | 5.10 | 123.8 | 1.42 | CH(CH$_2$)$^a$ |
| 7' | — | 135.1 | — | C |
| 7' OMe | N/A | N/A | 3.13 | OCH$_3$ |
| 8' | 1.95$^b$ | 39.8 | 1.42 | CH$_2$ |
| 9' | 2.04$^b$ | 26.8 | 1.93 | CH$_2$ |
| 10' | 5.07 | 124.3 | 5.12 | CH |
| 11' | — | 130.8 | — | C |
| 12' | 1.65 | 24.9 | 1.68 | CH$_3$ |
| 1" | 1.78 | 15.8 | 1.77 | CH$_3$ |
| 2" | 1.60 | 15.1 | 1.10 | CH$_3$ |
| 3" | 1.55 | 16.6 | 1.60 | CH$_3$ |

N/A: not applicable, group not present in the molecule $^a$CH in Compound 2, CH$_2$ in Compound 80

$^b$Signals for 4', 5', 8' and 9' are very close; assignment was based on Compound 1 b) Synthesis and Structural Elucidation of Compounds 14, 82, 83, 84, 85, and 87

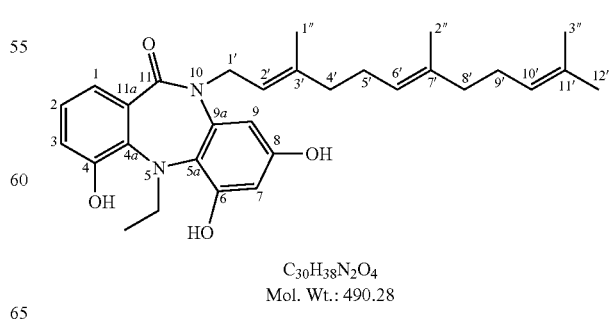

C$_{30}$H$_{38}$N$_2$O$_4$
Mol. Wt.: 490.28

Compound 14: 10-farnesyl-4,6,8-trihydroxy-5,10-dihydro-dibenzo[b,e][1,4]diazepin-11-one;

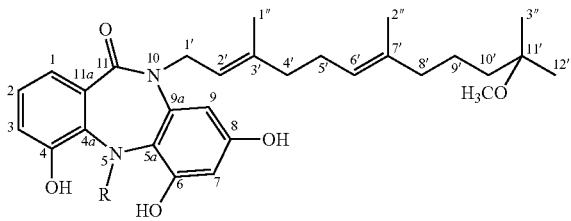

Compound 82:
R:H
$C_{29}H_{38}N_2O_5$
Mol. Wt.: 494.28
Compound 85:
R:Et
$C_{31}H_{42}N_2O_5$
Mol. Wt.: 522.31

Compound 82: 10-(1-methoxy-3,7,11-trimethyl-2,6-dodecadienyl)-4,6,8-trihydroxy-5,10-dihydro-dibenzo[b,e][1,4]diazepin-11-one;

Compound 85: 10-(1-methoxy-3,7,11-trimethyl-2,6-dodecadienyl)-4,6,8-trihydroxy-5-ethyl-5,10-dihydro-dibenzo[b,e][1,4]diazepin-11-one;

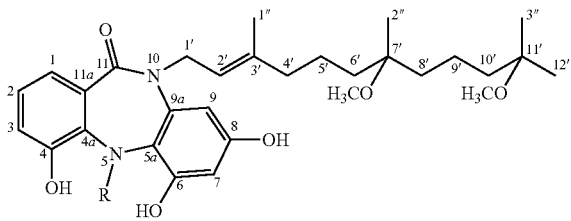

Compound 84:
R:H
$C_{30}H_{42}N_2O_6$
Mol. Wt.: 526.30
Compound 87:
R:Et
$C_{32}H_{46}N_2O_6$
Mol. Wt.: 554.34

Compound 84: 10-(7,11-dimethoxy-3,7,11-trimethyl-2-dodecenyl)-4,6,8-trihydroxy-5,10-dihydro-dibenzo[b,e][1,4]diazepin-11-one;

Compound 87: 10-(7,11-dimethoxy-3,7,11-trimethyl-2-dodecenyl)-4,6,8-trihydroxy-5-ethyl-5,10-dihydro-dibenzo[b,e][1,4]diazepin-11-one;

Preparation:

Compound 1 (85.3 mg) was stirred for 72 hrs at room temperature in a mixture of diethyl sulfate (2.0 mL) and $NaHCO_3$ (99.9 mg) in MeOH (2 mL). The resulting mixture was filtered through a 0.45 μm 13 mm Acrodisc™ GHP syringe filter. The solution was purified by preparative HPLC (multiple injections on a NovaPack™ HR C-18 25×200 mm column (20 mL/min, $H_2O/CH_3CN$ gradient 80:20-30:70, 0-8 min; 30:70-0:100, 8-18 min) to give four major peaks: Compound 14 (20.0 mg with some impurities, RT: 16.6 min), Compound 82 (5.65 mg, RT: 11.6 min), Compound 84 (2.20 mg, RT: 10.3 min), Compound 85 (17.54 mg, RT: 14.3 min) and Compound 87 (7.82 mg, RT: 12.6 min) were obtained. The fraction containing Compound 14 was further purified by HPLC using the same column (20 mL/min, $H_2O/CH_3CN$ gradient 80:20-30:70, 0-8 min; 30:70-0:100, 8-18 min, curve 7), to give substantially pure Compound 14 (13.85 mg, RT: 17.9 min).

Structural Elucidation of Compounds 14, 82, 84, 85 and 87:

The calculated molecular weight of the major isotope (490.28) and formula ($C_{30}H_{38}N_2O_4$) of Compound 14 was confirmed by mass spectral analysis: negative ionization gave an $(M-H)^-$ molecular ion of 489.3 and positive ionization gave an $(M+H)^+$ molecular ion of 491.3. Proton NMR signals were easily assigned based on Compounds 1 and 2 structures knowledge. The characteristic N-ethyl group (5-N-Et) was easily assigned as shown in Table 6.

The calculated molecular weight of the major isotope (494.28) and formula ($C_{29}H_{38}N_2O_5$) of Compound 82 was confirmed by mass spectral analysis: negative ionization gave an $(M-H)^-$ molecular ion of 493.3 and positive ionization gave an $(M+H)^+$ molecular ion of 495.4, and a fragment having an $(M+H-HOCH_3)^+$ molecular ion of 463.3. Proton NMR signals were easily assigned based on Compound 1 structure knowledge. The characteristic methoxy group (11'-OMe) and the methylene group (10'), from the addition of methanol on the farnesyl chain were easily assigned as shown in Table 6.

The calculated molecular weight (526.30) and formula ($C_{30}H_{42}N_2O_6$) of Compound 84 was confirmed by mass spectral analysis: negative ionization gave an $(M-H)^-$ molecular ion of 525.3 and positive ionization gave an $(M+H)^+$ molecular ion of 527.4, and fragments having respectively $(M+H-HOCH_3)^+$ and $(M+H-HOCH_3-HOCH_3)^+$ molecular ion of 495.4 and 463.4. Proton NMR signals were easily assigned based on Compound 1 structure knowledge. The characteristic methoxy groups (signals 7'-OMe and 11'-OMe) from the addition of two molecules of methanol on the farnesyl chain were easily assigned as shown in Table 6. The methylene groups (5', 6', 8', 9' and 10') were found to have similar chemical shifts, which is consistent with a saturated chain.

The calculated molecular weight of the major isotope (522.31) and formula ($C_{31}H_{42}N_2O_5$) of Compound 85 was confirmed by mass spectral analysis: negative ionization gave an $(M-H)^-$ molecular ion of 521.3 and positive ionization gave an $(M+H)^+$ molecular ion of 523.5, and a fragment having an $(M+H-HOCH_3)^+$ molecular ion of 491.3. The characteristic N-ethyl group (5-N-Et), and the methoxy (11'-OMe) and methylene (10') groups from the addition of methanol on the farnesyl chain were easily assigned as shown in Table 6.

The calculated molecular weight of the major isotope (554.34) and formula ($C_{32}H_{46}N_2O_6$) of Compound 87 was confirmed by mass spectral analysis: negative ionization gave an $(M-H)^-$ molecular ion of 553.4 and positive ionization gave an $(M+H)^+$ molecular ion of 555.4, and fragments having respectively $(M+H-HOCH_3)^+$ and $(M+H-HOCH_3-HOCH_3)^+$ molecular ion of 523.5 and 491.3. The characteristic N-ethyl group (5-N-Et), and methoxy (7'-OMe and 11'-OMe) groups from the addition of two molecules of methanol on the farnesyl chain were easily assigned as shown in Table 6. The methylene groups (5', 6', 8', 9' and 10') were all found to have similar chemical shifts, which is consistent with the saturated alkyl group.

TABLE 6

$^1$H NMR ($\delta_H$, ppm) Data of Compounds 14, 82, 84, 85 and 87 in MeOH-D$_4$

| Assignment | 14 | 82 | 84 | 85 | 87 | Group |
|---|---|---|---|---|---|---|
| 1 | 7.20 | 7.17 | 7.17 | 7.20 | 7.20 | CH |
| 2 | 7.13 | 6.77 | 6.76 | 7.14 | 7.14 | CH |
| 3 | 7.02 | 6.85 | 6.83 | 7.03 | 7.03 | CH |
| 5-N-Et (C1) | 3.23, 3.15 | N/A | N/A | 3.23, 3.15 | 3.24, 3.16 | CH$_2$ |
| 5-N-Et (C2) | 1.07 | N/A | N/A | 1.09 | 1.09 | CH$_3$ |
| 7 | 6.22 | 6.23 | 6.22 | 6.22 | 6.22 | CH |
| 9 | 6.34 | 6.28 | 6.27 | 6.34 | 6.34 | CH |
| 1' | 4.58, 4.56 | 4.55 | 4.57 | 4.82, 4.56 | 4.91, 4.54 | CH$_2$ |
| 2' | 5.41 | 5.37 | 5.37 | 5.41 | 5.38 | CH |
| 4' | 2.06 | 2.07 | 2.04 | 2.07 | 2.05 | CH$_2$ |
| 5' | 2.11 | 2.13 | * | 2.13 | ** | CH$_2$ |
| 6' | 5.10 | 5.12 | * | 5.11 | ** | CH (CH$_2$)$^a$ |
| 7'-OMe | N/A | N/A | 3.18 | N/A | 3.17 | OCH$_3$ |
| 8' | 1.95 | 1.97 | * | 1.95 | ** | CH$_2$ |
| 9' | 2.04 | 1.40 | * | 1.38 | ** | CH$_2$ |
| 10' | 5.07 | 1.40 | * | 1.38 | ** | CH (CH$_2$)$^b$ |
| 11'-OMe | N/A | 3.14 | 3.11 | 3.13 | 3.12 | OCH$_3$ |
| 12' | 1.65 | 1.10 | 1.16 | 1.08 | 1.14 | CH$_3$ |
| 1" | 1.77 | 1.74 | 1.72 | 1.78 | 1.78 | CH$_3$ |
| 2" | 1.60 | 1.61 | 1.10 | 1.10 | 1.10 | CH$_3$ |
| 3" | 1.55 | 1.10 | 1.16 | 1.08 | 1.14 | CH$_3$ |

N/A: not applicable, group not present in the molecule
* signal 1.22-1.51 ppm, 10 protons
** signal 1.22-1.49 ppm, 10 protons
$^a$CH in Compounds 14, 82 and 85, CH$_2$ in Compounds 84 and 87
$^b$CH in Compound 14, CH$_2$ in Compounds 82, 84, 85 and 87

Alternate Procedure, Preparation of Compounds 82 and 83:

Compound 1 (107.2 mg) and p-toluenesulfonic acid (PTSA, 13.8 mg) were stirred reflux in methanol for 30 minutes. The reaction was filtered and subjected to Waters HPLC purification (multiple injections on a NovaPack™ HR C-18 25×200 mm column: 20 mL/min, H$_2$O/CH$_3$CN gradient 70:30-20:80, 0-4 min; 20:80-0:100, 4-9 min) to give Compound 82 (8.5 mg, RT 7.2 min) and Compound 83 (4.3 mg, RT 7.7 min).

Structural elucidation of Compound 83 was done as for Compounds 82 and 84. Mass spectral analysis (ES$^+$: 495.5; ES$^-$: 493.3) confirmed a calculated molecular weight of the major isotope (494.28) and formula (C$_{29}$H$_{38}$N$_2$O$_5$) as for Compound 82. Proton NMR analysis showed signals 6' (1.42 ppm, CH$_2$) and 7'-OMe (3.13 ppm, OCH$_3$) corresponding to the addition of a methanol molecule on the second double bond of the farnesyl group (as for Compound 80).

c) Synthesis and Structural Elucidation of Compound 63

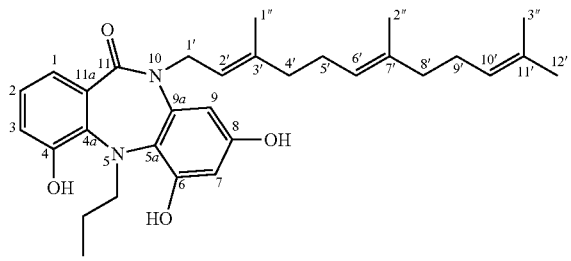

C$_{31}$H$_{40}$N$_2$O$_4$
Mol. Wt.: 504.30

Compound 63, namely 10-farnesyl-4,6,8-trihydroxy-5-n-propyl-5,10-dihydro-dibenzo[b,e][1,4]diazepin-11-one, was prepared and identified as follows:

Preparation:

Compound 1 (46.7 mg) was stirred for 72 hrs at room temperature in a mixture of dipropyl sulfate (0.5 mL) and NaHCO$_3$ (46.3 mg) in MeOH (3 mL). The resulting mixture was filtered through a 0.45 µm 13 mm Acrodisc™ GHP syringe filter. The solution was purified by preparative HPLC (multiple injections on a NovaPack™ HR C-18 25×200 mm column: 20 mL/min, H$_2$O/CH$_3$CN gradient 80:20-30:70, 0-8 min; 30:70-0:100, 8-18 min) to give substantially pure Compound 63 (18.0 mg, RT: 17.3 min).

Structural Elucidation of Compound 63:

The calculated molecular weight of the major isotope (504.30) and formula (C$_{31}$H$_{40}$N$_2$O$_4$) of Compound 63 was confirmed by mass spectral analysis: negative ionization gave an (M–H)$^-$ molecular ion of 503.4 and positive ionization gave an (M+H)$^+$ molecular ion of 505.5. Proton NMR signals were easily assigned based on Compounds 1 and 2 structures knowledge. The characteristic N-Propyl group (5-N-Pr (C1 to C3)) was easily assigned as shown in Table 7 below.

d) Synthesis and Elucidation of Compound 98

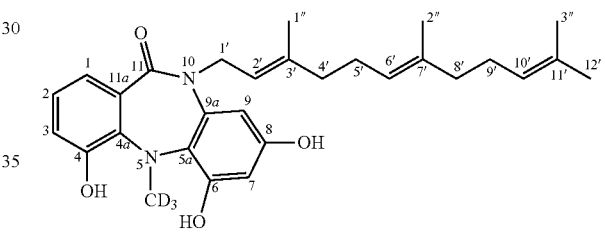

C$_{29}$H$_{33}$D$_3$N$_2$O$_4$
Mol. Wt.: 479.29

Compound 98: 10-Farnesyl-4,6,8-trihydroxy-5-(trideuteriomethyl)-5,10-dihydro-dibenzo[b,e][1,4]diazepin-11-one, was prepared and identified according to the following procedure:

Preparation:

Compound 1 (121.3 mg) was dissolved in MeOH (3.0 mL), dimethyl sulfate-d$_6$ (150 µL, CDN isotopes Inc.) and NaHCO$_3$ (58.1 mg) were added, and the reaction was stirred at room temperature overnight. The reaction mixture was filtered and the filtrate was subjected to Waters HPLC purification (multiple injections on Nova Pack™ HR C-18 25×200 mm column: 20 mL/min, H$_2$O/CH$_3$CN gradient 70:30-20:80, 0-4 min; 20:80-0:100, 4-9 min, and 100% CH$_3$CN, 9-12 min) to give Compound 98 (82.7 mg, RT 9.4 min).

Structural Elucidation:

The calculated molecular weight of the major isotope (479.29) and formula (C$_{29}$H$_{33}$D$_3$N$_2$O$_4$) of Compound 98 was confirmed by mass spectral analysis: negative ionization gave an (M–H)$^-$ molecular ion of 478.5, and positive ionization gave an (M+H)$^+$ molecular ion of 480.6. The structure was further confirmed by proton NMR spectrum as shown in Table 7 below.

TABLE 7

¹H NMR ($\delta_H$, ppm) Data of Compounds 63 and 98 in MeOH-D₄

| Assign | Compound 63 | Compound 98 | Group |
| --- | --- | --- | --- |
| 1 | 7.19 | 7.21 | CH |
| 2 | 7.12 | 7.14 | CH |
| 3 | 7.01 | 7.02 | CH |
| 5-N—Pr (C1) | 3.04, 3.15 | — | $CH_2^a$ |
| 5-N—Pr (C2) | 1.50 | N/A | $CH_2$ |
| 5-N—Pr (C3) | 0.91 | N/A | $CH_3$ |
| 7 | 6.22 | 6.22 | CH |
| 9 | 6.34 | 6.34 | CH |
| 1' | 4.54, 4.88 | 4.83, 4.59 | $CH_2$ |
| 2' | 5.40 | 5.44 | CH |
| 4' | 2.07 | 2.07 | $CH_2$ |
| 5' | 2.12 | 2.12 | $CH_2$ |
| 6' | 5.09 | 5.10 | CH |
| 8' | 1.96 | 1.95 | $CH_2$ |
| 9' | 2.03 | 2.03 | $CH_2$ |
| 10' | 5.07 | 5.07 | CH |
| 12' | 1.65 | 1.65 | $CH_3$ |
| 1" | 1.78 | 1.77 | $CH_3$ |
| 2" | 1.60 | 1.60 | $CH_3$ |
| 3" | 1.55 | 1.55 | $CH_3$ |

N/A: not applicable, group not present in the molecule
$^a CH_2$ in Compound 63, $CD_3$ in Compound 98.

Example 5

Alkyl Halide Reactions a) Synthesis and Structural Elucidation of Compound 3

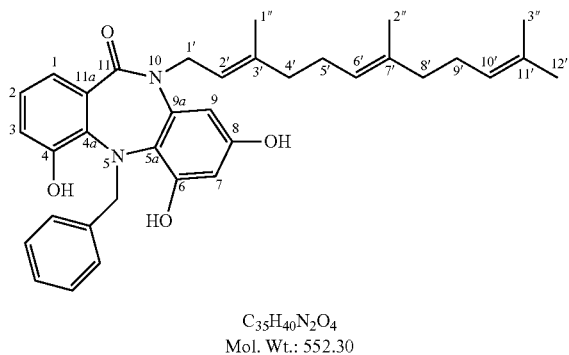

$C_{35}H_{40}N_2O_4$
Mol. Wt.: 552.30

Compound 3, namely 5-benzyl-10-farnesyl-4,6,8-trihydroxy-5,10-dihydro-dibenzo[b,e][1,4]diazepin-11-one was prepared and identified as follows:

Preparation:

Compound 1 (60.5 mg) was stirred 84 hrs with benzyl chloride (1.8 mL, 120 eq, Sigma) in presence of two drops of pyridine (Aldrich). The resulting mixture was directly subjected to HPLC separation. Purification by multiple injection on a Waters™ RCM Nova-Pak™ HR C18 6 μm 60A 25×200 mm column (20 mL/min H₂O/CH₃CN 80:20-30:70, 0-8 min; 30:70-0:100, 8-18 min, and 100% CH₃CN, 18-20 min) gave Compound 3 (46.0 mg) with retention time of 17.5 min.

Structural Elucidation:

The calculated molecular weight of the major isotope (552.30) and formula ($C_{35}H_{40}N_2O_4$) of Compound 3 was confirmed by mass spectral analysis: negative ionization gave an (M–H)⁻ molecular ion of 551.7 and positive ionization gave an (M+Na)⁺ molecular ion of 575.5. Proton NMR signals were easily assigned based on Compound 1 structure knowledge. The characteristic N-benzyl group (5-N-alkyl (C1-C5)) were assigned as shown in Table 8 below.

b) Synthesis and Structural Elucidation of Compound 64

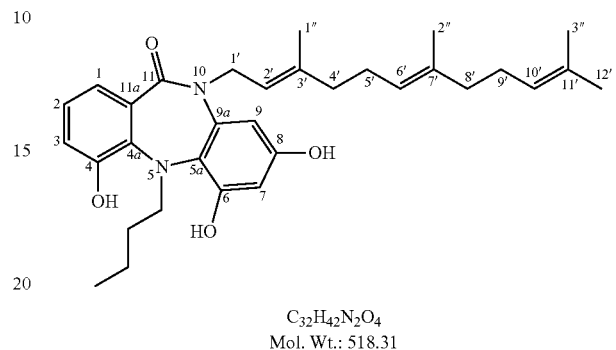

$C_{32}H_{42}N_2O_4$
Mol. Wt.: 518.31

Compound 64, namely 10-farnesyl-4,6,8-trihydroxy-5-n-butyl-5,10-dihydro-dibenzo[b,e][1,4]diazepin-11-one, was prepared and identified as follows:

Preparation:

Compound 1 (43.5 mg) was stirred in 1-bromobutane (2.0 mL) with pyridine (50 μL) at 80° C. overnight. The reaction mixture was diluted with MeOH (1.0 mL), filtered and subjected for Waters HPLC as described above (in a) to give a semi-purified Compound 64 (RT: 18.1 min). The semi-purified compound was further purified using the same conditions (except with curve 7) to give substantially pure Compound 64 (10.5 mg, RT: 17.9 min).

Structure Elucidation:

The calculated molecular weight of the major isotope (518.31) and formula ($C_{32}H_{42}N_2O_4$) of Compound 64 was confirmed by mass spectral analysis: negative ionization gave an (M–H)⁻ molecular ion of 517.4 and positive ionization gave an (M+H)⁺ molecular ion of 519.5. The characteristic N-n-butyl group (5-N-alkyl (C1-C4)) was easily assigned as shown in Table 8 below.

c) Synthesis and Structural Elucidation of Compound 67

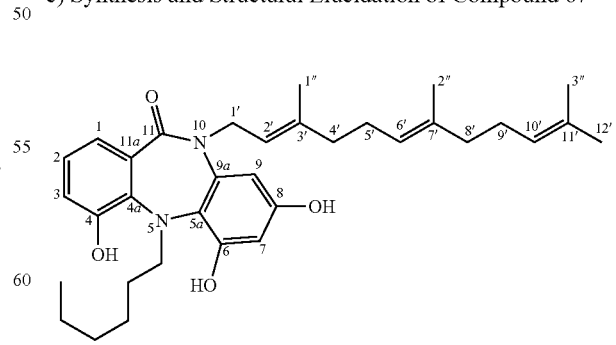

$C_{34}H_{46}N_2O_4$
Mol. Wt.: 546.35

Compound 67, namely 10-farnesyl-4,6,8-trihydroxy-5-n-hexyl-5,10-dihydro-dibenzo[b,e][1,4]diazepin-11-one, was prepared and identified as follows:

Preparation:

Compound 1 (39.2 mg) was stirred in 1-bromohexane (2.0 mL) with pyridine (50 µL) at 80° C. overnight. The reaction mixture was diluted with MeOH (1.0 mL), filtered and subjected for Waters HPLC (multiple injections on a Nova-Pack™ HR C-18 25×200 mm column: 20 mL/min, $H_2O$/$CH_3CN$ gradient 80:20-30:70, 0-8 min; 30:70-0:100, 8-18 min; isocratic $CH_3CN$ 18-24 minutes) to give substantially pure Compound 67 (14.0 mg, RT: 20.1 min).

Structural Elucidation:

The calculated molecular weight (546.35) and formula ($C_{34}H_{46}N_2O_4$) of Compound 67 was confirmed by mass spectral analysis: negative ionization gave an $(M-H)^-$ molecular ion of 545.6 and positive ionization gave an $(M+H)^+$ molecular ion of 547.6. Proton NMR signals were easily assigned based on Compounds 1 and 2 structures knowledge. The characteristic N-n-hexyl group (5-N-alkyl (C1-C6)) was easily assigned as shown in Table 8 below.

d) Synthesis and Structural Elucidation of Compound 77

$C_{32}H_{42}N_2O_4$
Mol. Wt.: 518.31

Compound 77, namely 10-Farnesyl-4,6,8-trihydroxy-5-sec-butyl-5,10-dihydro-dibenzo[b,e][1,4]diazepin-11-one, was prepared and identified as follows:

Preparation Procedure 1:

Compound 1 (26.0 mg) was stirred in 2-bromobutane (4.0 mL) with pyridine (100 µL) under reflux for one hour. The reaction mixture was concentrated in vacuo, diluted with MeOH (2.0 mL), filtered and subjected for Waters HPLC as described above (in a) to give Compound 77 (1.65 mg, RT: 18.0 min).

Preparation Procedure 2:

Compound 1 (104.5 mg) was stirred in 2-bromobutane (5.0 mL) with pyridine (400 µL) under reflux for two hours. The reaction mixture was concentrated in vacuo, diluted with MeOH (4.0 mL), filtered and subjected for Waters HPLC (multiple injections on a NovaPack™ HR C-18 25×200 mm column: 20 mL/min, $H_2O$/$CH_3CN$ gradient 70:30-20:80, 0-4 min; 20:80-0:100, 4-9 min) to give Compound 77 (7.38 mg, RT: 11.2 min).

Structure Elucidation:

The calculated molecular weight of the major isotope (518.31) and formula ($C_{32}H_{42}N_2O_4$) of Compound 77 was confirmed by mass spectral analysis: negative ionization gave an $(M-H)^-$ molecular ion of 517.4 and positive ionization gave an $(M+H)^+$ molecular ion of 519.6. The characteristic N-sec-butyl group (5-N-Alkyl (C1-C4)) was easily assigned as shown in Table 8 below.

TABLE 8

$^1$H NMR ($\delta_H$, ppm) Data of Compounds 3, 64, 67 and 77 in MeOH-$D_4$

| Assign | | 3 | 64 | 67 | 77 | Group |
|---|---|---|---|---|---|---|
| 1 | | 7.19 | 7.20 | 7.20 | 7.19 | CH |
| 2 | | 7.09 | 7.13 | 7.12 | 7.14 | CH |
| 3 | | 6.96 | 7.02 | 7.02 | 7.01 | CH |
| 5-N-alkyl | (C1) | 4.34, 4.25 | 3.18, 3.09 | 3.18, 3.08 | 3.29 | $a$ |
| | (C2) | — | 1.46 | 1.48 | 1.34 | $b$ |
| | (C3) | 7.20 | 1.35 | 1.30 | 086, 0.81$^h$ | $c$ |
| | (C4) | 7.23 | 0.89 | 1.30 | 1.00, 0.96$^h$ | $d$ |
| | (C5)$^e$ | 7.23 | N/A | 1.30 | N/A | $e$ |
| | (C6) | N/A | N/A | 0.89 | N/A | $f$ |
| 7 | | 6.16 | 6.22 | 6.23 | 6.22 | CH |
| 9 | | 6.31 | 6.34 | 6.33 | 6.34, 6.32$^h$ | CH |
| 1' | | 4.55, 4.48 | 4.89, 4.54 | 4.92, 4.52 | 4.90, 4.53 | $CH_2$ |
| 2' | | 5.44 | 5.40 | 5.39 | 5.41, 5.36$^h$ | CH |
| 4'$^g$ | | 2.08 | 2.06 | 2.06 | 2.06 | $CH_2$ |
| 5'$^g$ | | 2.13 | 2.12 | 2.11 | 2.13 | $CH_2$ |
| 6' | | 5.10 | 5.09 | 5.09 | 5.10 | CH |
| 8'$^g$ | | 1.94 | 1.96 | 1.96 | 1.97 | $CH_2$ |
| 9'$^g$ | | 2.01 | 2.04 | 2.04 | 2.05 | $CH_2$ |
| 10' | | 5.04 | 5.07 | 5.07 | 5.08 | CH |
| 12' | | 1.64 | 1.65 | 1.64 | 1.66 | $CH_3$ |
| 1" | | 1.79 | 1.78 | 1.78 | 1.80, 1.79$^h$ | $CH_3$ |
| 2" | | 1.56 | 1.60 | 1.60 | 1.61 | $CH_3$ |
| 3" | | 1.52 | 1.55 | 1.56 | 1.56 | $CH_3$ |

N/A: not applicable, group not present in the molecule
$^a$$CH_2$ in Compounds 3, 64, and 67; and CH in Compound 77.
$^b$C in Compound 3; $CH_2$ in Compounds 64, 67 and 77.
$^c$CH (2H) in Compound 3; $CH_2$ in Compounds 64 and 67; and $CH_3$ in Compound 77.
$^d$CH (2H) in Compound 3; $CH_3$ in Compounds 64 and 77; and $CH_2$ in Compound 67.
$^e$CH in Compound 3; $CH_2$ in Compound 67; absent in Compounds 64 and 77.
$^f$$CH_3$ in Compound 67; absent in Compounds 3, 64 and 77.
$^g$Signals at 4', 5', 8' and 9' are very close; assignment was based on Compound 1
$^h$From two different isomers.

e) Synthesis and Structural Elucidation of Compound 101

$C_{32}H_{40}N_2O_6$
Mol. Wt.: 548.29

Compound 101, namely (10-Farnesyl-4,6,8-trihydroxy-5,10-dihydrodibenzo[b,e][1,4]diazepin-11-on-5-yl)acetic acid ethyl ester, was prepared and identified as follows:

Preparation Procedure:

Compound 1 (100 mg) and bromoacetic acid (1.0 g) were stirred in ethanol (5.0 mL) under reflux for 30 minutes. The reaction mixture was diluted with water (150 mL) and extracted with ethyl acetate (3×150 mL). The organic layer was concentrated in vacuo, dissolved in MeOH (2.0 mL), filtered and subjected to Waters HPLC as described above (in Example 4(c)) to give Compound 101 (2.9 mg, RT: 17.0 min).

Structure Elucidation:

The calculated molecular weight of the major isotope (548.29) and formula ($C_{32}H_{40}N_2O_6$) of Compound 101 was confirmed by mass spectral analysis: positive ionization gave $(M+H)^+$ and $(M+Na)^+$ molecular ions respectively of 549.4 and 572.2. The characteristic ethyl acetate group (5-N-Alkyl (C1-C3)) was easily assigned as shown in Table 9 below.

f) Synthesis and Structural Elucidation of Compounds 102 and 103

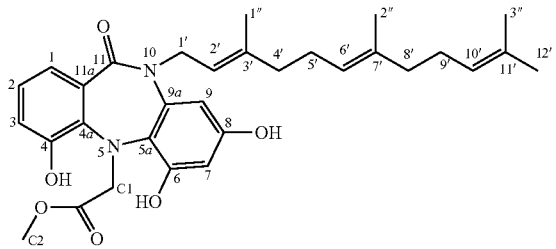

$C_{31}H_{38}N_2O_6$
Mol. Wt.: 534.27

Compound 102, namely (10-Farnesyl-4,6,8-trihydroxy-5,10-dihydrodibenzo[b,e][1,4]diazepin-11-on-5-yl)acetic acid methyl ester; and

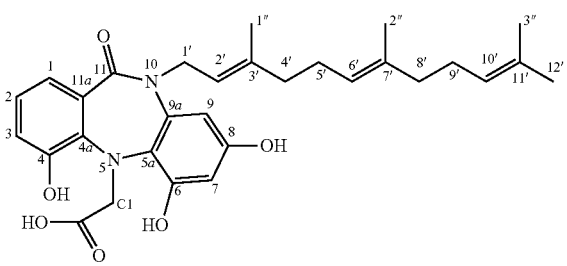

$C_{30}H_{36}N_2O_6$
Mol. Wt.: 520.26

Compound 103, namely (10-Farnesyl-4,6,8-trihydroxy-5,10-dihydrodibenzo[b,e][1,4]diazepin-11-on-5-yl)acetic acid; were prepared and identified as follows:

Preparation Procedure:

Compound 1 (100 mg) and bromoacetic acid (1.0 g) were stirred in methanol (5.0 mL) under reflux for 30 minutes. The reaction mixture was diluted with water (150 mL) and extracted with ethyl acetate (3×150 mL). The organic layer was concentrated in vacuo, dissolved in MeOH (2.0 mL), filtered and subjected to Waters HPLC as described above (in Example 4(c)) to give pure Compound 102 (12.5 mg, RT: 16.0 min) and Compound 103 (4.8 mg, RT: 12.6 min).

Structure Elucidation:

The calculated molecular weight of the major isotope (534.27) and formula ($C_{31}H_{38}N_2O_6$) of Compound 102 was confirmed by mass spectral analysis: positive ionization gave $(M+H)^+$ and $(M+Na)^+$ molecular ions respectively of 535.4 and 557.4. The characteristic methyl acetate group (5-N-Alkyl (C1-C2)) was easily assigned as shown in Table 9 below.

The calculated molecular weight of the major isotope (520.26) and formula ($C_{30}H_{36}N_2O_6$) of Compound 103 was confirmed by mass spectral analysis: negative ionization gave an $(M-H)^-$ molecular ion of 519.2. The characteristic acetic acid group (5-N-Alkyl (C1)) was easily assigned as shown in Table 9 below.

TABLE 9

$^1$H NMR ($\delta_H$, ppm) Data of Compounds 101, 102 and 103*

| Assignment | 101 | 102 | 103 | Group |
|---|---|---|---|---|
| 1 | 7.19 | 7.25 | 7.18 | CH |
| 2 | 7.14 | 7.21 | 7.14 | CH |
| 3 | 7.01 | 7.07 | 7.01 | CH |
| 5-N—R (C1) | 4.09, 3.95 | 4.08, 4.04 | 3.87, 3.80 | $CH_2$ |
| 5-N—R (C2) | 4.19 | 3.78 | N/A | a |
| 5-N—R (C3) | 1.25 | N/A | N/A | b |
| 7 | 6.22 | 6.24 | 6.20 | CH |
| 9 | 6.35 | 6.40 | 6.35 | CH |
| 1' | 4.88, 4.53 | 4.90, 4.48 | 4.88, 4.50 | $CH_2$ |
| 2' | 5.44 | 5.42 | 5.42 | CH |
| 4' | 2.07 | 2.07 | 2.08 | $CH_2$ |
| 5' | 2.12 | 2.12 | 2.12 | $CH_2$ |
| 6' | 5.08 | 5.11 | 5.08 | CH |
| 8' | 1.95 | 1.97 | 1.95 | $CH_2$ |
| 9' | 2.03 | 2.07 | 2.03 | $CH_2$ |
| 10' | 5.08 | 5.08 | 5.08 | CH |
| 12' | 1.66 | 1.68 | 1.65 | $CH_3$ |
| 1" | 1.77 | 1.76 | 1.77 | $CH_3$ |
| 2" | 1.60 | 1.62 | 1.59 | $CH_3$ |
| 3" | 1.56 | 1.59 | 1.55 | $CH_3$ |

*NMR done in MeOH-$D_4$ for Compounds 101 and 103, and in $CD_3CN$ for Compound 102
N/A: not applicable, group not present in the molecule
$^a CH_2$ in Compound 101, $CH_3$ in Compound 102.
$^b CH_3$ in Compound 101.

g) Synthesis of Compounds 104A, 104B and 104C

Compound 104A is prepared by reacting Compound 103 with, for example ammonia (bubbled in a solvent such as acetonitrile, and concentrated in vacuo), or by treating with one molar equivalent of an aqueous ammonium hydroxide. The aqueous solution is concentrated in vacuo, or freeze-dried to give the ammonium salt.

Compounds 104B and 104C are prepared by reacting Compound 103 with one molar equivalent of the corresponding base, e.g. aqueous sodium bicarbonate or potassium bicarbonate. Aqueous solutions of the salt formed are freeze-dried to give the desired base addition salt.

h) Synthesis of N-Alkyl Compounds:

N-Alkyl compounds of Formula I, and more specifically Compounds 2, 14, and 60 to 77 are also prepared by the procedures detailed in any of (a) to (e), by reaction of Compound 1 with the appropriate alkyl halide. Examples of alkyl halides to be used are methyl iodide, iodoethane, 3-chloro-1-butene, 1-chloro-2-methylpropane, crotylchloride, 1-bromopropane, 1-bromobutane, 1-bromo-2-methylbutane, 2-chloro-2-methylpropane, 1-bromohexane, 1-chlorooctane, trifluoromethyl iodide, heptafluoro-1-iodopropane, heptafluoro-2-iodopropane, 2-iodo-1,1,1-trifluoroethane, bromocyclopropane, bromocyclohexane, (2-bromoethyl)benzene, 1-bromo-3-phenylpropane, and 2-bromobutane, respectively for the production of Compounds 2, 14, and 60 to 77.

i) Synthesis and Structural Elucidation of Compounds 131 to 143

Compound 131

Preparation of Compound 131 (namely, [4,6,8-Trihydroxy-11-oxo-10-farnesyl-10,11-dihydro-dibenzo[b,e][1,4]diazepin-5-yl]-acetic acid ammonium salt): Compound 1 (1.0 g) was dissolved in dimethyl formamide (10.0 mL), 2.3 g of bromoacetic acid was added and the solution was stirred at 80° C. for 1 hour. The reaction mixture was filtered through a Waters GHP 0.45 □m filter and the filtrate was subjected to HPLC purification. Multiple injections on an ACE C-18 21×250 mm column (20 mL/min, 10 mM Ammonium acetate $H_2O/CH_3CN$ gradient 50:50-50:50, 0-5 min; 50:50-0:100, 5-12 min) yielded Compound 131 (501.0 mg) eluting at 8.0 min.

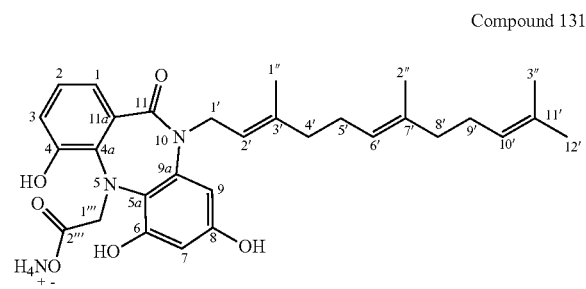

Compound 131

Compound 131 was calculated to have a molecular weight of 537.65, and a formula of $C_{30}H_{39}N_3O_6$. The structure of Compound 131 was confirmed by proton NMR, the data for which is presented in Table 91 below.

TABLE 9i $^1$H NMR data of Compound 131*

| Assignment. | Compound |
|---|---|
| 1 | 7.14 |
| 2 | 7.11 |
| 3 | 6.97 |
| 7 | 6.32 |
| 9 | 6.17 |
| 1' | 4.87, 4.48 |
| 2' | 5.38 |
| 4' | 2.07 |
| 5' | 2.10 |
| 6' | 5.07 |
| 8' | 1.94 |
| 9' | 2.02 |
| 10' | 5.06 |
| 12' | 1.63 |
| 1" | 1.74 |
| 2" | 1.58 |
| 3" | 1.55 |
| 1''' | 3.70 |
| 4''' | — |
| 5''' | — |

*The $^1$H NMR were measured in methanol-$d_4$

Compounds 132 to 136

Preparation of Compound 132 (namely, 5-(2-Bromo-ethyl)-4,6,8-trihydroxy-10-farnesyl-5,10-dihydro-dibenzo[b,e][1,4]diazepin-11-one): Compound 1 (200.0 mg) was dissolved in N,N-dimethylformamide (2.0 mL), 1.0 mL of 1,2-dibromoethane was added and the solution was stirred at water bath at 10° C. for 4 hrs. The reaction mixture was filtered through a Waters GHP 0.45 μm filter and the filtrate was subjected to HPLC purification. Multiple injections on an ACE C-18 21×250 mm column (20 mL/min, $H_2O/CH_3CN$ gradient 60:40-50:50, 0-2 min; 50:50-0:100, 2-6 min; 100% $CH_3CN$ till 12 min) yielded Compound 132 (20.1 mg) eluting at 10.0 min.

Compound 132 was calculated to have a molecular weight of 569.53, and to have a formula of $C_{30}H_{37}BrN_2O_4$.

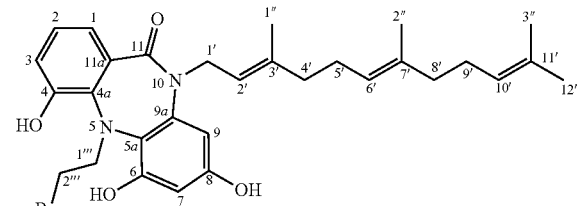

Compound 132

Preparation of Compound 133 (namely, 5-(3-Bromo-propyl)-4,6,8-trihydroxy-10-farnesyl-5,10-dihydro-dibenzo[b,e][1,4]diazepin-11-one): Compound 1 (200.0 mg) was dissolved in N,N-dimethylformamide (2.0 mL), 200 μL of 1,3-dibromopropane was added and the solution was stirred at water bath at 100° C. for 4 hrs. The reaction mixture was filtered through a Waters GHP 0.45 μm filter and the filtrate was subjected to HPLC purification. Multiple injections on an ACE C-18 21×250 mm column (20 mL/min, $H_2O/CH_3CN$ gradient 60:40-50:50, 0-2 min; 50:50-0:100, 2-6 min; 100% $CH_3CN$ till 12 min) yielded Compound 133 (13.9 mg) eluting at 10.1 min.

Compound 133 was calculated to have a molecular weight of 583.56, and to have a formula of $C_{31}H_{39}BrN_2O_4$.

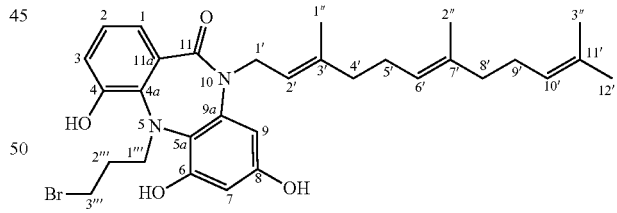

Compound 133

Preparation of Compound 134 (namely, 5-(4-Bromo-butyl)-4,6,8-trihydroxy-10-farnesyl-5,10-dihydro-dibenzo[b,e][1,4]diazepin-11-one): Compound 1 (100.0 mg) was dissolved in N,N-dimethylformamide (2.0 mL), 500 □L of 1,4-dibromobutane was added and the solution was stirred at water bath at 100° C. 3 hrs. The reaction mixture was filtered through a Waters GHP 0.45 □m filter and the filtrate was subjected to HPLC purification. Multiple injections on an ACE C-18 21×250 mm column (20 mL/min, 10 $H_2O/CH_3CN$ gradient 60:40-50:50, 0-2 min; 50:50-0:100, 2-12 min) yielded Compound 134 (45.5 mg) eluting at 10.0 min.

Compound 134 was calculated to have a molecular weight of 597.58, and to have a formula of $C_{32}H_{41}BrN_2O_4$.

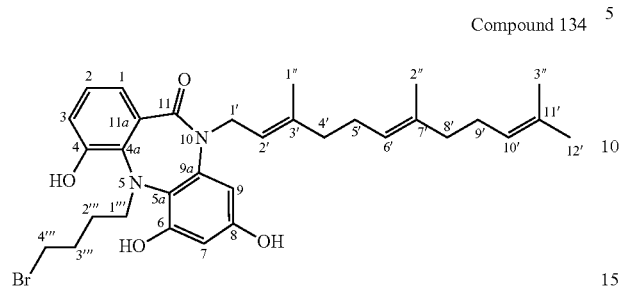

Compound 134

Preparation of Compound 135 (namely, 5-(3-Amino-propyl)-4,6,8-trihydroxy-10-farnesyl-5,10-dihydro-dibenzo[b,e][1,4]diazepin-11-one): Compound 133 (86.0 mg) was dissolved in tetrahydrofuran/dimethyl sulfoxide (1:2, 6.0 mL), 200 mg of sodium azide was added and the solution was stirred at room temperature for 72 hrs. The reaction mixture was filtered through a Waters GHP 0.45 □m filter and the filtrate was subjected to HPLC purification. Multiple injections on an ACE C-18 21×250 mm column eluting with CH₃CN (20 mL/min) yielded azide [N-(3-azopropyl) Compound 1] intermediate (45.0 mg) eluting at 4.6 min.

The azide [N-(3-azopropyl) Compound 1; 30.0 mg] was dissolved in MeOH (4.0 mL), 20 mg of Palladium (5% wt on calcium carbonate poisoned lead) was added and the solution was stirred at room temperature under hydrogen for 45 minutes. The reaction mixture was filtered through a Waters GHP 0.45 □m filter and the filtrate was subjected to HPLC purification. Multiple injections on an ACE C-18 21×250 mm column (20 mL/min, 10 mM ammonium acetate in H₂O/CH₃CN gradient 50:50-50:50, 0-3 min; 50:50-0:100, 3-10 min; 100% CH₃CN till 14 min) yielded Compound 135 (11.3 mg) eluting at 9.6 min.

Compound 135 was calculated to have a molecular weight of 519.67, and to have a formula of $C_{31}H_{41}N_3O_4$.

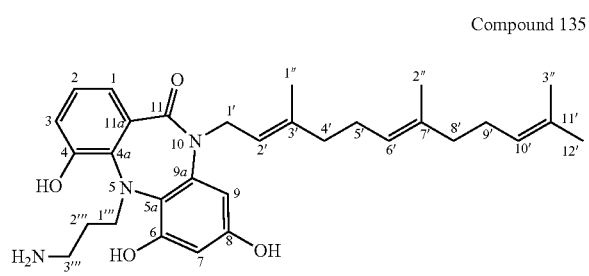

Compound 135

Preparation of Compound 136 (namely, 5-(3-Amino-propyl)-4,6,8-trihydroxy-10-farnesyl-5,10-dihydro-dibenzo[b,e][1,4]diazepin-11-one hydrochloride): Compound 135 (7.0 mg) was dissolved in diethyl ether/MeOH (9:1, 2.0 mL), few drops of 2M HCl in diethylether was added and the solution. The sample was dried under reduced pressure yielded Compound 136 (6.4 mg) soluble in water.

Compound 136 was calculated to have a molecular weight of 556.14, and to have a formula of $C_{31}H_{42}ClN_3O_4$.

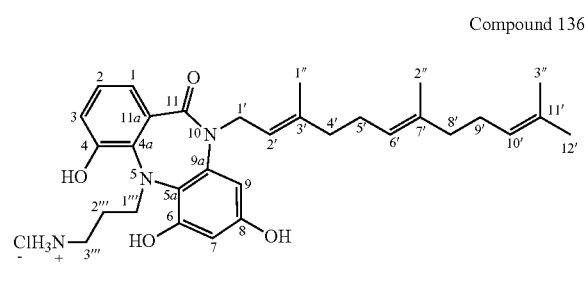

Compound 136

The structure of Compounds 132, 133, 134, 135 and 136 were confirmed by proton NMR, the data for which is presented in Table 9ii below.

TABLE 9ii $^1$H NMR data of Compounds 132 to 136*

| Assignment | Compound 132 | Compound 133 | Compound 134 | Compound 135 | Compound 136 |
|---|---|---|---|---|---|
| 1 | 7.21 | 7.22 | 7.21 | 7.21 | 7.23 |
| 2 | 7.14 | 7.15 | 7.13 | 7.14 | 7.16 |
| 3 | 7.03 | 7.04 | 7.03 | 7.03 | 7.05 |
| 7 | 6.36 | 6.36 | 6.35 | 6.35 | 6.38 |
| 9 | 6.24 | 6.24 | 6.24 | 6.23 | 6.25 |
| 1' | 4.90, 4.55 | 4.87, 4.58 | 4.57 | 4.58 | 4.69 |
| 2' | 5.43 | 5.44 | 5.41 | 5.43 | 5.45 |
| 4' | 2.09 | 2.08 | 2.09 | 2.08 | 2.10 |
| 5' | 2.14 | 2.13 | 2.13 | 2.13 | 2.16 |
| 6' | 5.09 | 5.11 | 5.10 | 5.11 | 5.13 |
| 8' | 1.96 | 1.96 | 1.96 | 1.96 | 1.96 |
| 9' | 2.04 | 2.04 | 2.04 | 2.04 | 2.03 |
| 10' | 5.07 | 5.07 | 5.07 | 5.07 | 5.06 |
| 12' | 1.66 | 1.65 | 1.66 | 1.66 | 1.64 |
| 1" | 1.79 | 1.79 | 1.79 | 1.79 | 1.80 |
| 2" | 1.61 | 1.61 | 1.61 | 1.61 | 1.62 |
| 3" | 1.55 | 1.55 | 1.55 | 1.56 | 1.53 |
| 1''' | 3.63, 3.54 | 3.37, 3.26 | 3.23, 3.13 | 3.29, 3.19 | 3.27 |
| 2'''' | 3.41 | 2.00 | 1.94 | 1.73 | 1.82 |
| 3'''' | — | 3.59 | 1.94 | 3.45 | 3.10 |
| 4'''' | — | — | 3.41 | — | — |

*The $^1$H NMR were measured in methanol-d₄

Compound 137

Preparation of Compound 137 (namely, 4,6,8-Trihydroxy-5,10-bisfarnesyl-5,10-dihydro-dibenzo[b,e][1,4]diazepin-11-one): Compound 1 (40.0 mg) was dissolved in dioxane (2.0 mL), 200 μL of farnesyl bromide and 40 mg of NaHCO₃ were added and the solution was stirred at room temperature overnight. The reaction mixture was filtered through a Waters GHP 0.45 μm filter and the filtrate was subjected to HPLC purification. Multiple injections on an ACE C-18 21×250 mm column (20 mL/min, H₂O/CH₃CN gradient 90:10-0:100, 0-18 min; 100% CH₃CN till 24 min) yielded ECO-04663 (15.6 mg) eluting at 19.2 min.

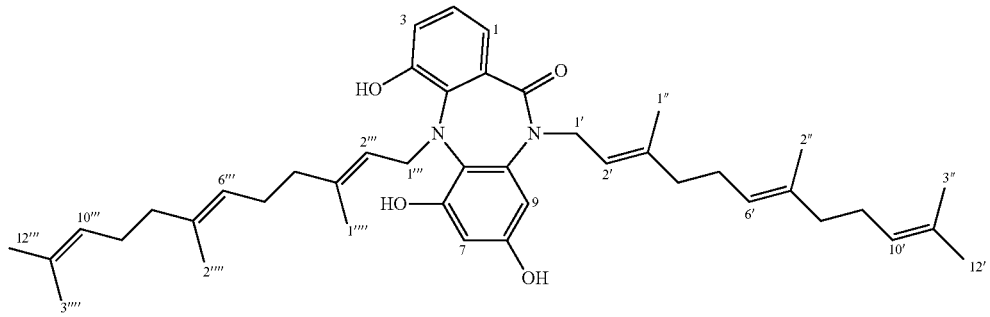

Compound 137

Compound 137 was calculated to have a molecular weight of 666.93, and to have a formula of $C_{43}H_{58}N_2O_4$. The structure of Compound 137 was confirmed by proton NMR, the data for which is presented in Table 9iii below.

TABLE 9iii $^1$H NMR data of Compound 137*

| Assignment | Compound 137 |
| --- | --- |
| 1 | 7.20 |
| 2 | 7.12 |
| 3 | 7.00 |
| 7 | 6.32 |
| 9 | 6.22 |
| 1' | 4.77, 4.62 |
| 2' | 5.45 |
| 4' | 2.05 |
| 5' | 2.12 |
| 6' | 5.11 |
| 8' | 1.96 |
| 9' | 1.96 |
| 10' | 5.06 |
| 12' | 1.65 |
| 1'' | 1.79 |
| 2'' | 1.60 |
| 3'' | 1.54 |
| 1''' | 3.83, 3.74 |
| 2''' | 5.23 |
| 4''' | 1.96 |
| 5''' | 2.07 |
| 6''' | 5.09 |
| 8''' | 1.96 |
| 9''' | 1.96 |
| 10''' | 5.05 |
| 12''' | 1.61 |
| 1'''' | 1.68 |
| 2'''' | 1.58 |
| 3'''' | 1.48 |

*The $^1$H NMR were measured in methanol-$d_4$

Compounds 138 to 143

Preparation of Compound 138 (namely, 6-Oxo-6-[4,6,8-trihydroxy-11-oxo-10-farnesyl-10,11-dihydro-dibenzo[b,e][1,4]diazepin-5-yl]-hexanoic acid): Compound 1 (12.0 mg) was dissolved in acetone (1.5 mL), 50 μL of adipoyl chloride was added and the solution was stirred at room temperature for 1 hours. The reaction mixture was diluted by water (2.0 mL) and filtered through a Waters GHP 0.45 μm filter. The filtrate was subjected to HPLC purification, multiple injections on an ACE C-18 21×250 mm column (20 mL/min, $H_2O/CH_3CN$ gradient 95:5-0:100, 0-30 min) yielded Compound 138 (5.7 mg) eluting at 8.4 min.

Compound 138 was calculated to have a molecular weight of 590.71, and to have a formula of $C_{34}H_{42}N_2O_7$.

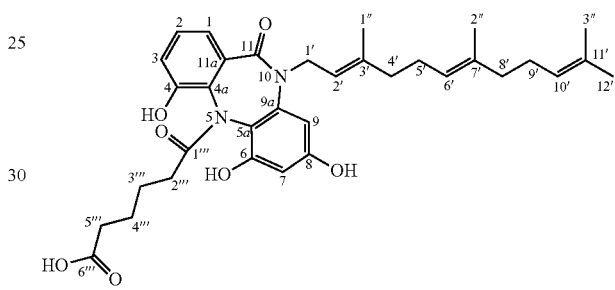

Compound 138

Preparation of Compound 139 (namely, 6-Oxo-6-[4,6,8-trihydroxy-11-oxo-10-farnesyl-10,11-dihydro-dibenzo[b,e][1,4]diazepin-5-yl]-hexanoic acid ammonium salt): Compound 138 (5.7 mg) was dissolved in MeOH (2.0 mL) and NaOH solution (10 μL 30% in water) was added and the sample was dried under reduced pressure yielded Compound 139 (5.0 mg).

Compound 139 was calculated to have a molecular weight of 612.69, and to have a formula of $C_{34}H_{41}N_2NaO_7$.

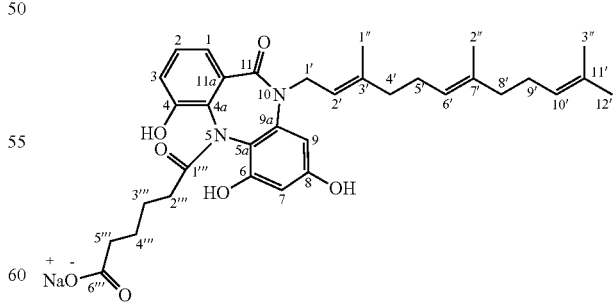

Compound 139

Preparation of Compound 140 (namely, 5-(4-Dimethylamino-benzoyl)-4,6,8-trihydroxy-10-farnesyl-5,10-dihydro-dibenzo[b,e][1,4]diazepin-11-one): Compound 103 (50.0 mg) was dissolved in acetonitrile/DMF (3:1, 4.0 mL), 50.0 mg of 4-(dimethylamino)benzoyl chloride was added and the solution was stirred at room temperature for 1 hours. The reaction mixture was filtered through a Waters GHP 0.45 μm filter and the filtrate was subjected to HPLC purification. Multiple injections on an ACE C-18 21×250 mm column (20 mL/min, $H_2O/CH_3CN$ gradient 50:50-0:100, 0-15 min; 100% $CH_3CN$ till 18 min) yielded Compound 140 (47.0 mg) eluting at 15.4 min.

Compound 140 was calculated to have a molecular weight of 609.75, and to have a formula of $C_{37}H_{43}N_3O_5$.

Compound 140

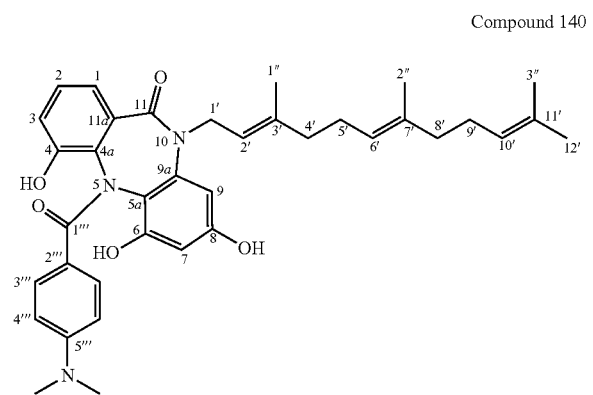

Preparation of Compound 141 (namely, 4,6,8-Trihydroxy-5-(pyridine-3-carbonyl)-10-farnesyl-5,10-dihydro-dibenzo[b,e][1,4]diazepin-11-one): Compound 103 (116.0 mg) was dissolved in N,N-dimethylformamide (2.0 mL), 133.5 mg of nicotinoyl chloride hydrochloride was added and the solution was stirred at room temperature for 1 hours. The reaction mixture was filtered through a Waters GHP 0.45 □m filter and the filtrate was subjected to HPLC purification. Multiple injections on an ACE C-18 21×250 mm column (20 mL/min, $H_2O/CH_3CN$ gradient 80:20-30:70, 0-8 min; 30:70-0:100, 8-18 min) yielded Compound 141 (100 mg) eluting at 14.1 min.

Compound 141 was calculated to have a molecular weight of 567.67, and to have a formula of $C_{34}H_{37}N_3O_5$.

Compound 141

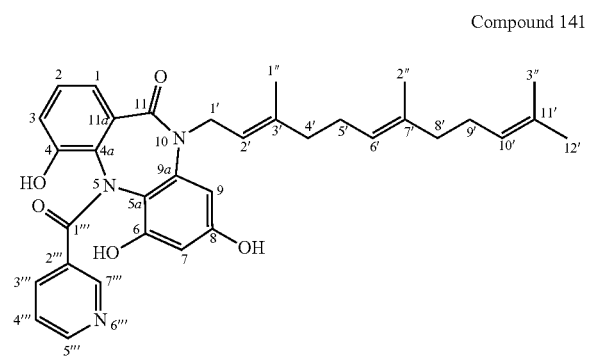

Preparation of Compound 142 (namely, 4,6,8-Trihydroxy-5-(2-morpholin-4-yl-ethyl)-10-farnesyl-5,10-dihydro-dibenzo[b,e][1,4]diazepin-11-one): Compound 103 (1.0 g) was dissolved in N,N-dimethylformamide (15.0 mL), 2.0 mL of 4-(2-chloroethyl)morpholine was added and the solution was refluxed for 1 hour. 4-(2-Chloroethyl)morpholine (1.0 mL) further added to the reaction mixture twice in 1 hr interval. The reaction mixture was finally filtered through a Waters GHP 0.45 μm filter and the filtrate was subjected to HPLC purification. Multiple injections on an ACE C-18 21×250 mm column (20 mL/min, $H_2O/CH_3CN$ gradient 50:50-50:50, 0-2 min; 50:50-0:100, 2-9 min, 100% $CH_3CN$ till 15 min) yielded Compound 142 (600 mg) eluting at 12.4 min.

Compound 142 was calculated to have a molecular weight of 575.74, and to have a formula of $C_{34}H_{45}N_3O_5$.

Compound 142

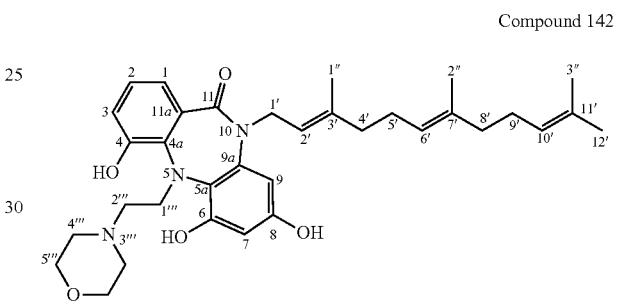

Preparation of Compound 143 (namely, 4,6,8-Trihydroxy-5-(2-morpholin-4-yl-ethyl)-10-farnesyl-5,10-dihydro-dibenzo[b,e][1,4]diazepin-11-one hydrochloride): Compound 142 (5.0 mg) was dissolved in diethyl ether/MeOH (9:1, 2.0 mL), few drops of 2M HCl in diethyl was added and the solution. The sample was dried under reduced pressure yielded Compound 143 (4.8 mg) soluble in water.

Compound 143 was calculated to have a molecular weight of 612.20, and to have a formula of $C_{34}H_{46}ClN_3O_5$.

Compound 143

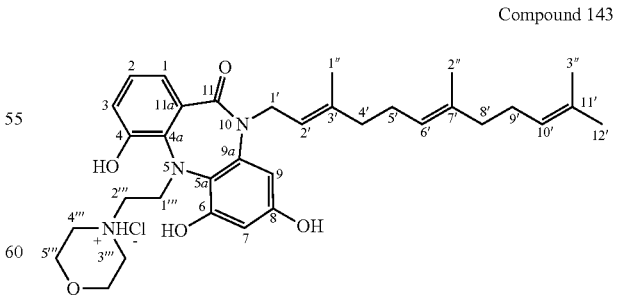

The structure of Compounds 138 to 143 were confirmed by proton NMR, the data for which is presented in Table 9iv below.

TABLE 9iv $^1$H NMR data of Compounds 138 to 143*

| Assignment | Compound 138 | Compound 139 | Compound 140 | Compound 141** | Compound 142 | Compound 143 |
|---|---|---|---|---|---|---|
| 1 | 7.29 | 7.23 | 7.26 | 7.17 | 7.20 | 7.20 |
| 2 | 7.23 | 7.19 | 7.21 | 6.77 | 7.15 | 7.15 |
| 3 | 7.12 | 7.06 | 7.12 | 6.86 | 7.02 | 7.02 |
| 7 | 6.45 | 6.38 | 6.46 | 6.26 | 6.36 | 6.36 |
| 9 | 6.33 | 6.28 | 6.33 | 6.05 | 6.22 | 6.22 |
| 1' | 4.85, 4.53 | 4.77, 4.57 | 4.80, 4.54 | 4.55 | 4.88, 4.52 | 4.88, 4.52 |
| 2' | 5.32 | 5.37 | 5.39 | 5.34 | 5.42 | 5.42 |
| 4' | 2.05 | 2.05 | 1.98 | 2.05 | 2.06 | 2.06 |
| 5' | 2.12 | 2.14 | 2.04 | 2.08 | 2.11 | 2.11 |
| 6' | 5.11 | 5.12 | 5.08 | 5.09 | 5.09 | 5.09 |
| 8' | 1.96 | 1.97 | 1.98 | 1.96 | 1.96 | 1.96 |
| 9' | 2.05 | 2.05 | 1.98 | 2.05 | 2.04 | 2.04 |
| 10' | 5.08 | 5.07 | 5.05 | 5.09 | 5.07 | 5.07 |
| 12' | 1.65 | 1.65 | 1.66 | 1.67 | 1.66 | 1.66 |
| 1" | 1.78 | 1.78 | 1.76 | 1.73 | 1.77 | 1.77 |
| 2" | 1.61 | 1.62 | 1.58 | 1.60 | 1.60 | 1.60 |
| 3" | 1.55 | 1.54 | 1.55 | 1.58 | 1.56 | 1.56 |
| 1''' | — | — | — | — | 2.49 | 2.49 |
| 2''' | 2.50 | 2.49 | — | — | 2.45 | 2.45 |
| 3''' | 2.04 | 2.05 | 7.54 | 7.83 | — | — |
| 4''' | 2.04 | 2.14 | 5.59 | 6.78 | 2.61 | 2.61 |
| 5''' | 2.28 | 2.28 | — | 7.67 | 3.81 | 3.81 |
| 5'''-N(Me)$_2$ | — | — | 2.99 | — | — | — |
| 7''' | — | — | — | 6.37 | — | — |

*The $^1$H NMR were measured in methanol-d$_4$
**The $^1$H NMR was measured in dimethylsulfoxide-d$_4$

Example 6

O-alkyl Analogs a) Diazoalkane Reaction (O-methylation):

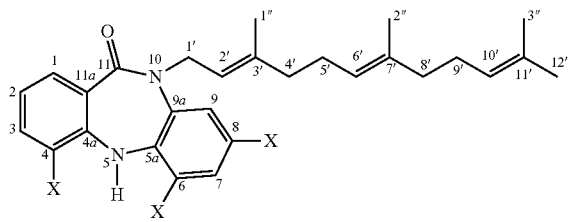

Compound 4: 4-OMe  6-OH  8-OH
Compound 5: 4-OH   6-OMe 8-OH
Compound 6: 4-OH,  6-OMe 8-OMe
Compound 7: 4-OMe  6-OMe 8-OH
Compound 8: 4-OMe  6-OMe 8-OMe Compounds 4 and 5: 10-farnesyl-6,8-dihydroxy-4-methoxy-5,10-dihydro-dibenzo[b,e][1,4]diazepin-11-one and 10-farnesyl-4,8-dihydroxy-6-methoxy-5,10-dihydro-dibenzo[b,e][1,4]diazepin-11-one, are monomethylated have a calculated molecular weight of the major isotope of 476.27 g/mol and a formula of $C_{29}H_{36}N_2O_4$.

Compounds 6 and 7: 10-farnesyl-4-hydroxy-6,8-dimethoxy-5,10-dihydro-dibenzo[b,e][1,4]diazepin-11-one and 10-farnesyl-8-hydroxy-4,6-dimethoxy-5,10-dihydro-dibenzo[b,e][1,4]diazepin-11-one, are dimethylated and have a calculated molecular weight of the major isotope of 490.28 g/mol and a formula of $C_{30}H_{38}N_2O_4$.

Compound 8: 10-farnesyl-4,6,8-trimethoxy-5,10-dihydro-dibenzo[b,e][1,4]diazepin-11-one, is trimethylated and has a calculated molecular weight of the major isotope of 504.30 g/mol and a formula of $C_{31}H_{40}N_2O_4$.

All O-methylated compounds (4 to 8) were prepared and identified according to the following procedure:

Preparation:

Compound 1 (20.0 mg) in MeOH (2.0 mL) was treated with excess of $CH_2N_2$ in diethyl ether and the mixture stirred overnight. The resulting mixture was separated by preparative TLC (Merck Silica gel 60 $F_{254}$), using 2.5% MeOH in $CHCl_3$ as eluent. A mixture of Compounds 4 and 5 (1.0 mg), Compound 6 (0.5 mg), Compound 7 (5.5 mg) and Compound 8 (3.0 mg) were isolated with Rf value of 0.09, 0.35, 0.39 and 0.92 respectively.

Structural Elucidation:

The calculated molecular weights of the major isotopes (mono: 476.27, di: 490.28 and tri: 504.30) and formulae (mono: $C_{29}H_{36}N_2O_4$, di: $C_{30}H_{38}N_2O_4$ and tri: $C_{31}H_{40}N_2O_4$) respectively of mono methylated (Compounds 4 and 5), dimethylated (Compounds 6 and 7) and trimethylated (Compound 8) were confirmed by mass spectral (MS) analysis. MS of both Compounds 4 and 5 gave a (M−H)$^−$ molecular ion of 475.5 by negative ionization and a (M+Na)$^+$ molecular ion of 499.4 by positive ionization. MS of Compound 6 gave a (M−H)$^−$ molecular ion of 489.5 by negative ionization and a (M+Na)$^+$ molecular ion of 513.4 by positive ionization. MS of Compound 7 gave a (M−H)$^−$ molecular ion of 489.5 by negative ionization and a (M+Na)$^+$ molecular ion of 513.4 by positive ionization. MS of Compound 8 gave a (M−H)$^−$ molecular ion of 503.6 by negative ionization and a (M+Na)$^+$ molecular ion of 527.4 by positive ionization. Proton NMR spectral analysis for Compounds 4 to 8 is shown in Table 10. Signals were easily assigned based on comparison with the spectra of Compound 1.

(b) Isolation of a Mono-Glucuronide Analog:

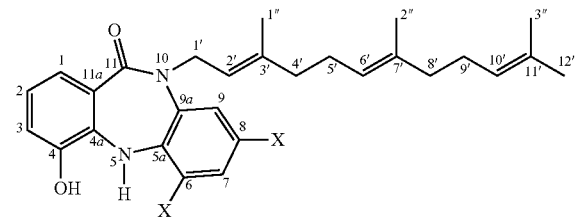

Compound 107: 4-OH 6-OG 8-OH
Compound 108: 4-OH, 6-OH 8-OG
$C_{34}H_{42}N_2O_{10}$
Exact Mass: 638.28

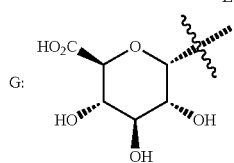

G:

A mono-glucuronide analog (Compound 107 or 108) was isolated and identified as follows:

Compound 107: 10-farnesyl-6-β-glucoronyloxy-4,8-dihydroxy-5,10-dihydro-dibenzo[b,e][1,4]diazepin-11-one; OR Compound 108: 10-farnesyl-8-β-glucoronyloxy-4,6-dihydroxy-5,10-dihydro-dibenzo[b,e][1,4]diazepin-11-one;

Preparation Procedure:

A 200 mL sample of urine taken from a rat fed with Compound 1 was stirred with HP-20 resin (20 mL) overnight at room temperature. The resin was washed with water (400 mL) followed by gradient elution by water/methanol (200 mL) to get four fractions (Fraction 1: 80:20; Fraction 2: 50:50; Fraction 3: (20:80); and Fraction 4 (0:100)). Fractions 3 and 4 were combined, concentrated in vacuo, re-dissolved in DMSO and filtered. The filtrate was subjected HPLC purification on a YMC-Pack ODS-AQ™ C18, 20×250 mm column (20 mL/min, $H_2O/CH_3CN$ 95:5-50:50, 0-12 min; 50:50-0:100, 12-16 min) to give a mono glucuronide that would be identified either as Compound 107 or 108 (46 μg, RT: 18.2 min).

Structure Elucidation:

The calculated molecular weight of the major isotope (638.28) and formula ($C_{34}H_{42}N_2O_{10}$) of the mono-glucuronide analog (Compound 107 or 108) isolated was confirmed by mass spectral analysis: positive ionization gave an $(M+H)^+$ molecular ion of 639.2. NMR signals were assigned as shown in Table 10. Signals having chemical shifts of 4.85, 3.66, 3.68, 3.78, and 3.57 ppm, each integrating for one proton, were assigned to the characteristic glucuronide group. The first CH (4.85 ppm) was determined as the anomeric proton attached to the phenolic alcohol.

TABLE 10

$^1$H NMR ($\delta_H$, ppm) Data of Compounds 4, 5, 6, 7, 8 and mono-G in MeOH-$D_4$

| Assign. | 4 | 5 | 6 | 7 | 8 | Mono-G | Group |
|---|---|---|---|---|---|---|---|
| 1 | 7.28 | 7.17 | 7.19 | 7.28 | 7.29 | 7.20 | CH |
| 2 | 6.91 | 6.78 | 6.86 | 6.92 | 6.92 | 6.81 | CH |
| 3 | 7.03 | 6.86 | 6.79 | 7.03 | 7.03 | 6.92 | CH |
| 4-OMe | 3.94 | N/A | N/A | 3.93 | 3.94 | N/A | a |
| 5 | N/D | N/D | N/D | N/D | 6.95 | N/D | NH |

TABLE 10-continued $^1$H NMR ($\delta_H$, ppm) Data of Compounds 4, 5, 6, 7, 8 and mono-G in MeOH-$D_4$

| Assign. | 4 | 5 | 6 | 7 | 8 | Mono-G | Group |
|---|---|---|---|---|---|---|---|
| 6-OMe | N/A | 3.87 | 3.91 | 3.87 | 3.89 | N/A$^e$ | b |
| 7 | 6.28 | 6.23 | 6.46 | 6.33 | 6.45 | 6.65 | CH |
| 8-OMe | N/A | N/A | 3.75 | N/A | 3.74 | N/A$^e$ | c |
| 9 | 6.38 | 6.34 | 6.52 | 6.38 | 6.57 | 6.49 | CH |
| 1' | 4.56 | 4.56 | 4.61 | 4.57 | 4.60 | 4.56 | $CH_2$ |
| 2' | 5.36 | 5.36 | 5.38 | 5.34 | 5.31 | 5.40 | CH |
| 4'$^d$ | 2.05 | 2.05 | 2.05 | 2.05 | 2.04 | 2.07 | $CH_2$ |
| 5'$^d$ | 2.10 | 2.10 | 2.09 | 2.09 | 2.08 | 2.12 | $CH_2$ |
| 6' | 5.09 | 5.09 | 5.07 | 5.08 | 5.06 | 5.13 | CH |
| 8'$^d$ | 1.96 | 1.96 | 1.95 | 1.95 | 1.93 | 1.97 | $CH_2$ |
| 9'$^d$ | 2.04 | 2.04 | 2.04 | 2.04 | 2.03 | 2.03 | $CH_2$ |
| 10' | 5.09 | 5.09 | 5.07 | 5.08 | 5.06 | 5.08 | CH |
| 12' | 1.66 | 1.66 | 1.65 | 1.66 | 1.65 | 1.65 | $CH_3$ |
| 1" | 1.74 | 1.74 | 1.75 | 1.73 | 1.73 | 1.75 | $CH_3$ |
| 2" | 1.60 | 1.60 | 1.60 | 1.59 | 1.59 | 1.62 | $CH_3$ |
| 3" | 1.57 | 1.57 | 1.55 | 1.57 | 1.55 | 1.56 | $CH_3$ |

N/D: Not determined - not observed
$^a$X is $OCH_3$ in Compounds 4, 7 and 8; X is OH in Compounds 5 and 6.
$^b$X is $OCH_3$ in Compounds 5, 6, 7 and 8; X is OH in Compound 4.
$^c$X is $OCH_3$ in Compounds 6 and 8; X is OH in Compounds 4, 5 and 7.
$^d$Signals of 4', 5', 8' and 9' are very close; assignement was based on Compound 1.
$^e$Glucuronide (X is O-G) signals (G in 6 or 8) appeared at 4.85, 3.66, 3.68, 3.78, and 3.57 as described above.

Example 7

O-Acylations a) Synthesis and Structural Elucidation of Compounds 9 to 12 (O-acetylation):

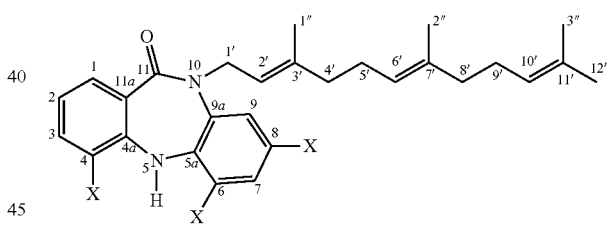

X is:
Compound 9: 4-OH 6-OAc 8-OAc
Compound 10: 4-OAc 6-OAc 8-OH
Compound 11: 4-OAc 6-OH 8-OAc
Compound 12: 4-OAc 6-OAc 8-OAc Ac is:

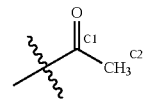

Compounds 9, 10 and 11: 6,8-diacetoxy-10-farnesyl-4-hydroxy-5,10-dihydro-dibenzo[b,e][1,4]diazepin-11-one; 4,6-diacetoxy-10-farnesyl-8-hydroxy-5,10-dihydro-dibenzo[b,e][1,4]diazepin-11-one and 4,8-diacetoxy-10-farnesyl-6-hydroxy-5,10-dihydro-dibenzo[b,e][1,4]diazepin-11-one, are diacetylated and have a calculated molecular weight of the major isotope of 546.27 g/mol and a formula of $C_{32}H_{38}N_2O_6$.

Compound 12: 4,6,8-triacetoxy-10-farnesyl-5,10-dihydrodibenzo[b,e][1,4]diazepin-11-one, is triacetylated and has a calculated molecular weight of the major isotope of 588.28 g/mol and a formula of $C_{34}H_{40}N_2O_7$.

All acetylated compounds (9 to 12) were prepared and identified according to the following procedure:

Preparation:

Compound 1 (120.5 mg) was stirred overnight with acetic anhydride (720 µL, 29 eq, Aldrich) in presence of 6 drops of pyridine (Aldrich). The reaction mixtures submitted to HPLC separation. Purification by multiple injection on a Waters™ RCM Nova-Pak HR™ C18, 6 µm, 60A 25×200 mm column (20 mL/min H₂O/CH₃CN 80:30-70:75, 0-8 min; 30:70-0:100, 8-18 min and HPLC run for 20 min) gave Compound 11 (11.4 mg), Compound 10 (9.2 mg), Compound 9 (11.4 mg), Compound 12 (91.2 mg) with retention time of 16.2, 17.6, 18.0 and 18.5 min, respectively.

Structural Elucidation:

The calculated molecular weights of the major isotopes (di: 546.27 and tri: 588.28) and formulae (di: $C_{32}H_{38}N_2O_6$ and tri: $C_{34}H_{40}N_2O_7$) respectively of diacetylated (Compounds 9, 10 and 11) and triacetylated (Compound 12) were confirmed by mass spectral (MS) analysis. MS of Compound 9 gave a $(M-H)^-$ molecular ion of 545.6 by negative ionization and a $(M+Na)^+$ molecular ion of 569.4 by positive ionization. MS of Compound 10 gave a $(M-H)^-$ molecular ion of 545.6 by negative ionization and a $(M+Na)^+$ molecular ion of 569.5 by positive ionization. MS of Compound 11 gave a $(M-H)^-$ molecular ion of 545.5 by negative ionization and a $(M+Na)^+$ molecular ion of 569.4 by positive ionization. MS of Compound 12 gave a $(M-H)^-$ molecular ion of 587.6 by negative ionization and a $(M+Na)^+$ molecular ion of 611.5 by positive ionization. Proton NMR spectral analysis for Compounds 9 to 12 is shown in Table 11. Signals were easily assigned based on comparison with the spectra of Compound 1.

b) Synthesis and Structural Elucidation of Compound 105 (O-benzoylation):

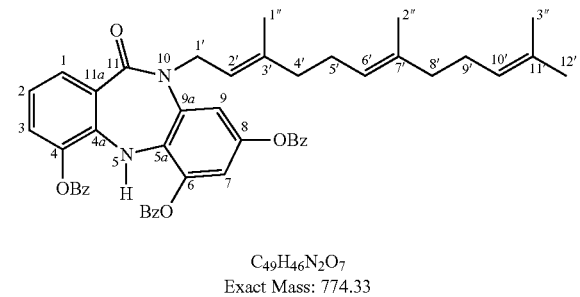

Compound 105: 4,6,8-tribenzoyloxy-10-farnesyl-5,10-dihydro-dibenzo[b,e][1,4]diazepin-11-one $C_{49}H_{46}N_2O_7$
Exact Mass: 774.33

Bz is:

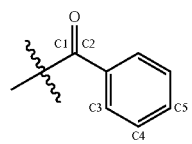

The tribenzoylated Compound 105 was prepared and identified according to the following procedure:

Preparation:

Compound 1 (200 mg) was dissolved in pyridine (4.0 mL) and benzoyl chloride (400 mL) was added and the reaction stirred at room temperature for 3 hours. The reaction mixture was diluted in water (200 mL) and extracted with ethyl acetate (2×200 mL). The organic layers were combined and concentrated in vacuo. The residue was dissolved in methanol, filtered, and submitted to HPLC separation. Purification by multiple injection on a Waters™ RCM Nova-Pak™ HR C18, 6 µm, 60A 25×200 mm column (20 mL/min H₂O/CH₃CN 70:30-0:100, 0-4 min; 100% CH₃CN 4-14 min) gave a semi-purified Compound 105 (RT: 11.2 min). The semi-purified product was submitted to the same HPLC column (20 mL/min, isocratic CH₃CN) to give pure Compound 105 (84.2 mg, RT 5.3 min).

Structural Elucidation:

The calculated molecular weight of the major isotopes (774.33) and formulae ($C_{49}H_{46}N_2O_7$) of Compound 105 were confirmed by mass spectral (MS) analysis. MS of Compound 105 gave $(M+H)^+$ and $(M+Na)^+$ molecular ions respectively of 535.4 and 557.4 by positive ionization. Proton NMR spectral analysis of Compound 105 is shown in Table 11. Signals were easily assigned based on comparison with the spectra of Compound 1.

TABLE 11

$^1$H NMR ($\delta_H$, ppm) Data of Compounds 9, 10, 11, 12 (in CDCl₃) and 105 (in CD₃CN)

| Assignment | | 9 | 10 | 11 | 12 | 105 | Group |
|---|---|---|---|---|---|---|---|
| 1 | | 7.27 | 7.72 | 7.75 | 7.75 | 7.26 | CH |
| 2 | | 6.67 | 6.99 | 7.02 | 7.10 | 7.10 | CH |
| 3 | | 6.67 | 7.15 | 7.15 | 7.16 | 7.74 | CH |
| 4 OR | C(2) | N/D | 2.42 | 2.42 | 2.41 | $^b$ | $^b$ |
| | C(3) | N/A | N/A | N/A | N/A | 8.15 | $^c$ |
| | C(4) | N/A | N/A | N/A | N/A | 7.58 | $^d$ |
| | C(5) | N/A | N/A | N/A | N/A | 7.72 | $^e$ |
| 5 | | 6.45 | 5.90 | 6.29 | 6.15 | 6.57 | NH |
| 6 OR | C(2) | 2.36 | 2.41 | N/D | 2.40 | $^f$ | $^f$ |
| | C(3) | N/A | N/A | N/A | N/A | 8.00 | $^c$ |
| | C(4) | N/A | N/A | N/A | N/A | 7.33 | $^d$ |
| | C(5) | N/A | N/A | N/A | N/A | 7.58 | $^e$ |
| 7 | | 6.82 | 6.52 | 6.15 | 6.96 | 7.25 | CH |
| 8 OR | C(2) | 2.28 | N/D | 2.25 | 2.27 | $^g$ | $^g$ |
| | C(3) | N/A | N/A | N/A | N/A | 7.80 | $^c$ |
| | C(4) | N/A | N/A | N/A | N/A | 7.21 | $^d$ |
| | C(5) | N/A | N/A | N/A | N/A | 7.50 | $^e$ |
| 9 | | 6.95 | 6.67 | 6.55 | 6.84 | 7.01 | CH |
| 1' | | 4.60 | 4.57 | 4.57 | 4.58 | 4.64 | CH₂ |
| 2' | | 5.43 | 5.38 | 5.41 | 5.42 | 5.43 | CH |
| 4'$^a$ | | 2.08 | 2.06 | 2.05 | 2.06 | 2.07 | CH₂ |
| 5'$^a$ | | 2.09 | 2.08 | 2.09 | 2.09 | 2.08 | CH₂ |
| 6' | | 5.10 | 5.09 | 5.09 | 5.10 | 5.08 | CH |
| 8'$^a$ | | 1.98 | 1.97 | 1.98 | 1.98 | 1.93 | CH₂ |
| 9'$^a$ | | 2.08 | 2.06 | 2.05 | 2.06 | 2.02 | CH₂ |
| 10' | | 5.10 | 5.09 | 5.09 | 5.10 | 5.08 | CH |
| 12' | | 1.69 | 1.69 | 1.69 | 1.68 | 1.64 | CH₃ |
| 1" | | 1.72 | 1.70 | 1.71 | 1.72 | 1.74 | CH₃ |
| 2" | | 1.61 | 1.60 | 1.60 | 1.61 | 1.56 | CH₃ |
| 3" | | 1.60 | 1.60 | 1.60 | 1.60 | 1.56 | CH₃ |

N/D: Not determined - not observed
N/A: Not applicable, group not present in the molecule
$^a$Signals of 4', 5', 8' and 9' are very close; assignement was based on Compound 1.
$^b$Ac (CH₃) in Compounds 10, 11 and 12; H in Compound 9; C(1) (aryl) in Compound 105.
$^c$CH in Compound 105 (ortho, 2H).
$^d$CH in Compound 105 (meta, 2H).
$^e$CH in Compound 105 (para, 1H).
$^f$Ac (CH₃) in Compounds 9, 10 and 12; H in Compound 11; C (aryl) in Compound 105.
$^g$Ac (CH₃) in Compounds 9, 11 and 12; H in Compound 10; C (aryl) in Compound 105.

c) Synthesis and Structural Elucidation of Compounds 144 to 154

Compound 144

Preparation of Compound 144 (namely, 4,6,8-Tri-O-(pyridine-3-carbonyl)-10-farnesyl-5,10-dihydro-dibenzo[b,e][1, 4]diazepin-11-one): Compound 1 (23.1 mg) was dissolved in pyridine/N,N-dimethylformamide (1:1, 2.0 mL) and stirred at room temperature overnight with nicotinoyl chloride hydrochloride (131.7 mg). The reaction mixture was filtered through a Waters GHP 0.45 µm filter and the filtrate was subjected to HPLC purification. Multiple injections on an ACE C-18 21×250 mm column (20 mL/min, $H_2O/CH_3CN$ gradient 80:20-30:70, 0-8 min; 30:70-0:100, 8-18 min; 100% $CH_3CN$ till 24 min) yielded Compound 144 (5.0 mg, purity 80%) eluting at 14.1 min.

Compound 144 was calculated to have a molecular weight of 777.86, and to have a formula of $C_{46}H_{43}N_5O_7$.

Compound 144

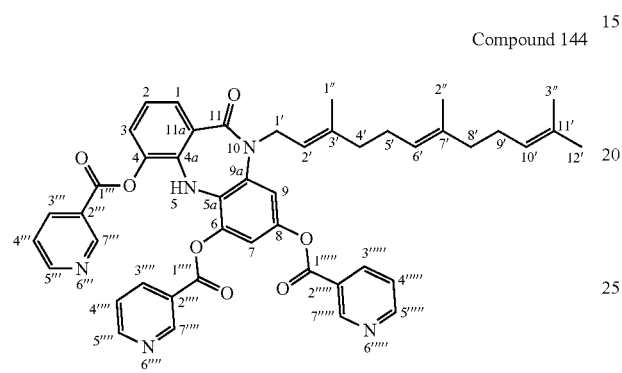

The structure of Compound 144 was confirmed by proton NMR, the data for which is presented in Table 11i below.

TABLE 11i $^1$H NMR data of Compound 144*

| Assignment. | Compound 144 |
|---|---|
| 1 | *** |
| 2 | *** |
| 3 | *** |
| NH | *** |
| 7 | *** |
| 9 | *** |
| 1' | 4.55 |
| 2' | 5.38 |
| 4' | 1.97 |
| 5' | 2.10 |
| 6' | 5.11 |
| 8' | 1.97 |

TABLE 11i-continued $^1$H NMR data of Compound 144*

| Assignment. | Compound 144 |
|---|---|
| 9' | 2.05 |
| 10' | 5.04 |
| 12' | 1.64 |
| 1" | 1.74 |
| 2" | 1.61 |
| 3" | 1.57 |
| 3''' | *** |
| 4''' | *** |
| 5''' | *** |
| 7''' | *** |
| 3'''' | *** |
| 4'''' | *** |
| 5'''' | *** |
| 7'''' | *** |
| 3''''' | *** |
| 4''''' | *** |
| 5''''' | *** |
| 7''''' | *** |

*The $^1$H NMR were measured in methanol-$d_4$
*** Signals were overlaps from 8.67-6.07 ppm Compounds 145 to 147

Preparation of Compound 145 (namely, 4-Dimethylamino-benzoic acid 6,8-dihydroxy-11-oxo-10-farnesyl-10,11-dihydro-5H-dibenzo[b,e][1,4]diazepin-4-yl ester), Compound 146 (namely, 4-Dimethylamino-benzoic acid 4,8-dihydroxy-11-oxo-10-farnesyl-10,11-dihydro-5H-dibenzo[b,e][1,4]diazepin-6-yl ester) and Compound 147 (namely, 4-Dimethylamino-benzoic acid 6-(4-dimethylamino-benzoylloxy)-8-hydroxy-11-oxo-10-farnesyl-10,11-dihydro-5H-dibenzo[b,e][1,4]diazepin-4-yl ester): Compound 1 (10.0 mg) was dissolved in pyridine (2.0 mL) and stirred at room temperature overnight 4-(dimethylamino)benzoyl chloride (10.0 □L). The reaction mixture was filtered through a Waters GHP 0.45 µm filter and the filtrate was subjected to HPLC purification. Multiple injections on an ACE C-18 21×250 mm column (20 mL/min, $H_2O/CH_3CN$ gradient 90:5-0:100, 0-30 min) yielded Compound 145 (1.3 mg), Compound 146 (1.7 mg) and Compound 147 (0.7 mg) eluting at 12.2, 12.6 and 14.4 minutes, respectively.

Compound 145 was calculated to have a molecular weight of 609.75, and to have a formula of $C_{37}H_{43}N_3O_5$.

Compound 145

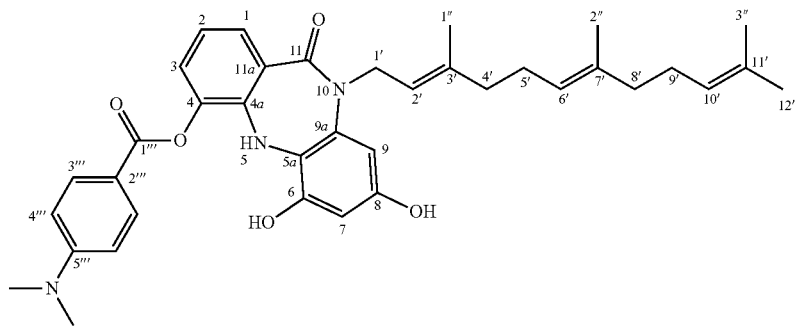

Compound 146 was calculated to have a molecular weight of 609.75, and to have a formula of $C_{37}H_{43}N_3O_5$.

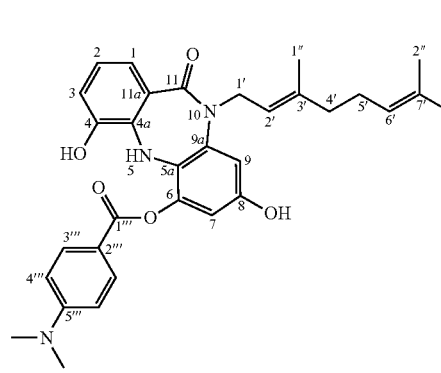

Compound 146

Compound 147 was calculated to have a molecular weight of 756.93, and to have a formula of $C_{46}H_{52}N_4O_6$.

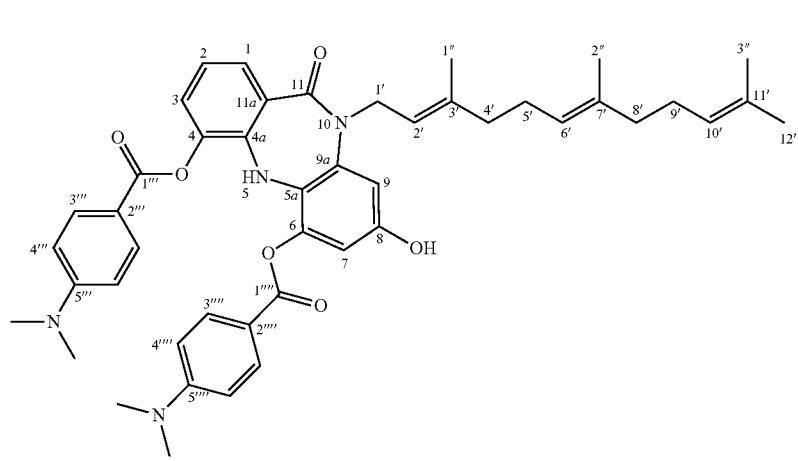

Compound 147

The structure of Compounds 145 to 147 were confirmed by proton NMR, the data for which is presented in Table 11ii below.

TABLE 11ii $^1$H NMR data of Compounds 145 to 147*

| Assignment | Compound 145 | Compound 146 | Compound 147 |
|---|---|---|---|
| 1 | 7.62 | 7.24 | 7.65 |
| 2 | 7.04 | 6.83 | 7.04 |
| 3 | 7.29 | 6.88 | 7.18 |
| NH | 6.23 | 6.47 | 6.29 |
| 7 | 6.43 | 6.72 | 6.75 |
| 9 | 6.34 | 6.57 | 6.46 |
| 1' | 4.57 | 4.61 | 4.63 |
| 2' | 5.35 | 5.38 | 5.40 |
| 4' | 2.06 | 2.08 | 2.08 |
| 5' | 2.11 | 2.12 | 2.12 |
| 6' | 5.12 | 5.14 | 5.14 |
| 8' | 1.96 | 2.01 | 2.03 |
| 9' | 2.06 | 2.08 | 2.08 |
| 10' | 5.10 | 5.14 | 5.11 |
| 12' | 1.67 | 1.68 | 1.67 |

TABLE 11ii-continued $^1$H NMR data of Compounds 145 to 147*

| Assignment | Compound 145 | Compound 146 | Compound 147 |
|---|---|---|---|
| 1'' | 1.74 | 1.77 | 1.77 |
| 2'' | 1.61 | 1.64 | 1.63 |
| 3'' | 1.59 | 1.60 | 1.60 |
| 3''' | 8.13 | 8.11 | 7.83 |
| 4''' | 6.84 | 6.84 | 6.56 |
| N(Me)$_2$ | 3.33, 3.12 | 3.33, 3.12 | 3.33, 3.06 |
| 3'''' | — | — | 7.64 |
| 4'''' | — | — | 6.39 |
| N(Me)$_2$ | — | — | 3.33, 3.02 |

*The $^1$H NMR were measured in acetronitrle-d$_3$

Compounds 148 to 152

Preparation of Compound 148 (namely, Dimethyl-carbamic acid 6,8-dihydroxy-11-oxo-10-farnesyl-10,11-dihydro-5H-dibenzo[b,e][1,4]diazepin-4-yl ester), Compound 149 (namely, hydroxy-11-oxo-10-farnesyl-10,11-dihydro-5H-dibenzo[b,e][1,4]diazepin-4-yl ester), Compound 150 (namely, Dimethyl-carbamic acid 8-dimethylcarbamoyloxy-6-hydroxy-11-oxo-10-farnesyl-10,11-dihydro-5H-dibenzo[b,e][1,4]diazepin-4-yl ester), Compound 151 (namely, Dimethyl-carbamic acid 8-dimethylcarbamoyloxy-4-hydroxy-11-oxo-10-farnesyl-10,11-dihydro-5H-dibenzo[b,e][1,4]diazepin-6-yl ester) and Compound 152 (namely, Dimethyl-carbamic acid 6,8-bis-dimethylcarbamoyloxy-11-oxo-10-farnesyl-10,11-dihydro-5H-dibenzo[b,e][1,4]diazepin-4-yl ester): Compound 1 (316 g) was dissolved in pyridine (5.0 mL) and stirred at room temperature for 24 hours with N,N-dimethylcarbamide chloride (130 µL). Additional 30 µL N,N-dimethylcarbamide chloride was added to the reaction and further stirred the reaction additional 24 hrs more. The reaction mixture was filtered through a Waters GHP 0.45 µm filter and the filtrate was subjected to HPLC purification. Multiple injections on an ACE C-18 21×250 mm column (20 mL/min, H$_2$O/CH$_3$CN gradient 50:50-0:100, 0-15 min; 100% CH$_3$CN till 18 min) yielded Compound 148 (5.0 mg), Compound 149 (50.5 mg), Compound 150 (2.5 mg), Compound 151 (20.1 mg) and Compound 152 (51.1 mg) eluting at 12.1, 13.9, 15.5, 15.9 and 16.3 minutes, respectively.

Compound 148 was calculated to have a molecular weight of 533.66, and to have a formula of $C_{31}H_{39}N_3O_5$.

Compound 148

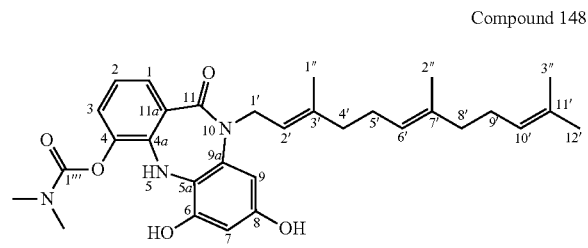

Compound 149 was calculated to have a molecular weight of 604.74, and to have a formula of $C_{34}H_{44}N_4O_6$.

Compound 149

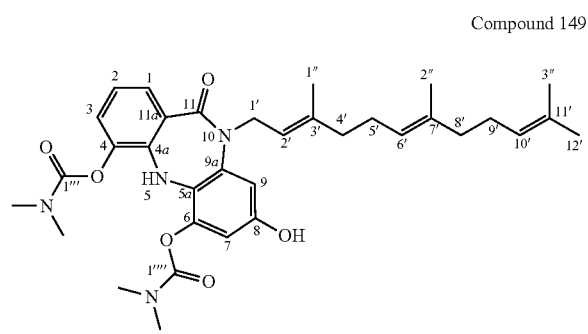

Compound 150 was calculated to have a molecular weight of 604.74, and to have a formula of $C_{34}H_{44}N_4O_6$.

Compound 150

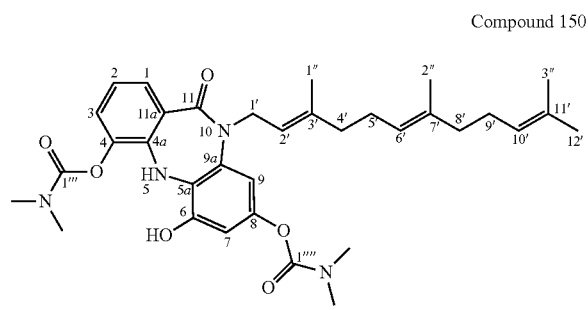

Compound 151 was calculated to have a molecular weight of 604.74, and to have a formula of $C_{34}H_{44}N_4O_6$.

Compound 151

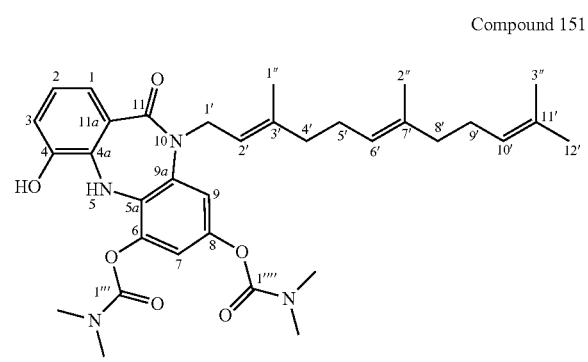

Compound 152 was calculated to have a molecular weight of 675.81, and to have a formula of $C_{37}H_{49}N_5O_7$ Compound 152

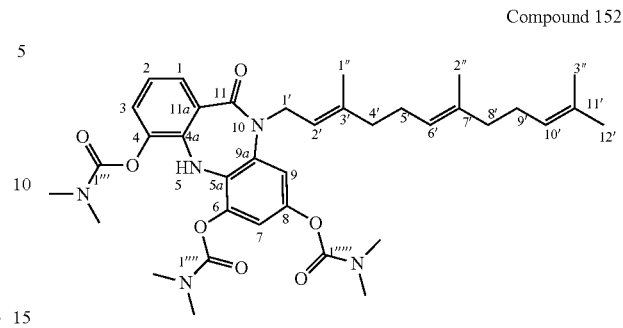

The structure of Compounds 148 to 152 were confirmed by proton NMR, the data for which is presented in Table 11iii below.

TABLE 11iii $^1$H NMR data of Compounds 148 to 152

| Assignment. | Compound 148 | Compound 149 | Compound 150 | Compound 151 | Compound 152 |
|---|---|---|---|---|---|
| 1 | 7.57 | 7.58 | 7.59 | 7.20 | 7.61 |
| 2 | 6.99 | 7.00 | 7.03 | 6.85 | 7.04 |
| 3 | 7.19 | 7.17 | 7.23 | 6.90 | 7.20 |
| 7 | 6.30 | 6.70 | 6.64 | 7.06 | 7.08 |
| 9 | 6.23 | 6.41 | 6.48 | 6.85 | 6.83 |
| 1' | 4.58 | 4.60 | 4.59 | 4.62 | 4.61 |
| 2' | 5.37 | 5.38 | 5.39 | 5.42 | 5.42 |
| 4' | 2.05 | 2.05 | 2.05 | 2.07 | 2.05 |
| 5' | 2.10 | 2.11 | 2.09 | 2.12 | 2.07 |
| 6' | 5.10 | 5.10 | 5.10 | 5.10 | 5.11 |
| 8' | 1.97 | 1.96 | 1.95 | 1.95 | 1.96 |
| 9' | 2.05 | 2.05 | 2.05 | 2.04 | 2.05 |
| 10' | 5.08 | 5.08 | 5.07 | 5.07 | 5.07 |
| 12' | 1.66 | 1.66 | 1.65 | 1.65 | 1.65 |
| 1" | 1.74 | 1.75 | 1.73 | 1.75 | 1.74 |
| 2" | 1.60 | 1.61 | 1.61 | 1.61 | 1.61 |
| 3" | 1.57 | 1.57 | 1.55 | 1.55 | 1.57 |
| 1'''-N(Me)$_2$ | 3.27, 3.05 | 3.20, 3.06 | 3.28, 3.06 | 3.26, 3.04 | 3.21, 3.06 |
| 1''''-N(Me)$_2$ | — | 3.17, 3.04 | 3.09, 2.98 | 3.10, 2.99 | 3.18, 3.04 |
| 1'''''-N(Me)$_2$ | — | — | — | — | 3.09, 2.98 |

*The $^1$H NMR were measured in methanol-$d_4$

Compounds 153 and 154

Preparation of Compound 153 (namely, 8-Hydroxy-4,6-bis-(2-morpholin-4-yl-ethoxy)-10-farnesyl-5,10-dihydro-dibenzo[b,e][1,4]diazepin-11-one): Compound 1 (1.15 g) was dissolved in N,N-dimethylformamide (10.0 mL) and solution was kept at 150° C. for 2 min. Sodium bicarbonate (1.15 g) and 4-(2-chloroethyl)-morpholine hydrochloride (1.15 g) were added to the solution and the resulting mixture was refluxed for 1 hour. The reaction mixture diluted by MeOH (50 mL) and filtered. The filtrate was concentrated under reduced pressure and subjected to HPLC purification. Multiple injections on an ACE C-18 21×250 mm column (20 mL/min, H$_2$O/CH$_3$CN gradient 80:20-30:70, 0-5 min; 30:70-0:100, 5-10 min and 100% CH$_3$CN till 18 min) yielded Compound 153 (0.85 g) eluting at 12.9 min.

Compound 153 was calculated to have a molecular weight of 688.90, and to have a formula of $C_{40}H_{56}N_4O_6$.

Compound 153

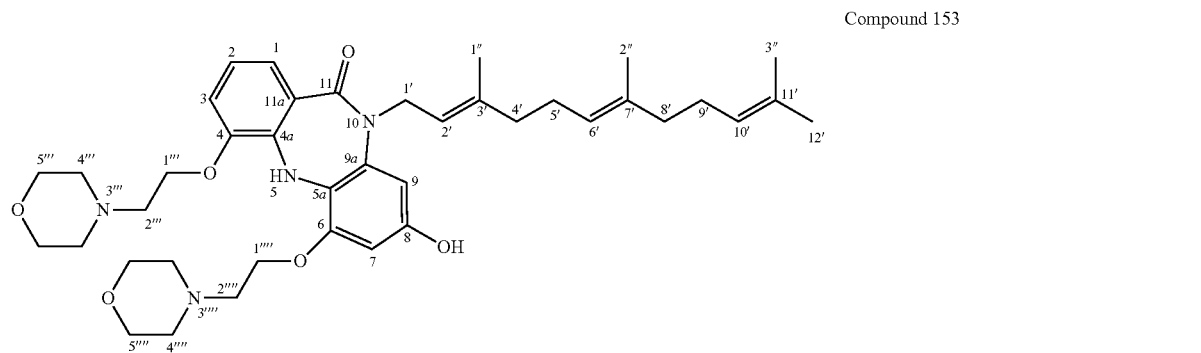

Preparation of Compound 154 (namely, 8-Hydroxy-4,6-bis-(2-morpholin-4-yl-ethoxy)-10-farnesyl-5,10-dihydro-dibenzo[b,e][1,4]diazepin-11-one hydrochloride): Compound 153 (200 mg) was dissolved in diethyl ether (10.0 mL) and few drops of 2M HCl (in diethyl ether) were added to the solution. White precipitate was developed, which was further dissolved by addition of MeOH (10.0 mL). The resulting solution was concentrated under reduced pressure to 5.0 mL and kept at 2-8° C. for overnight. Colorless crystal of Compound 154 (157.2 mg) was obtained by filtration.

Compound 154 was calculated to have a molecular weight of 761.82, and to have a formula of $C_{40}H_{58}C_{12}N_4O_6$.

Compound 154

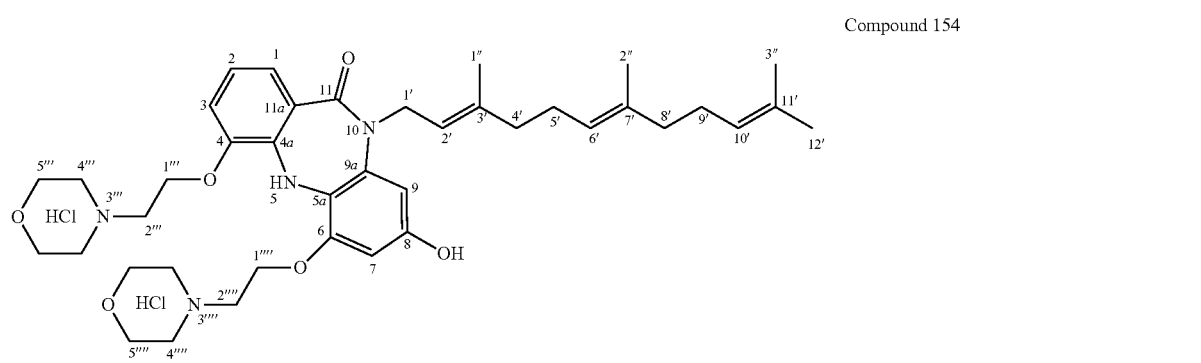

The structure of Compounds 153 and 154 were confirmed by proton NMR, the data for which is presented in Table 11iv below.

TABLE 11iv $^1$H NMR data of Compound 153 and Compound 154*

| Assignementt | Compound 153 | Compound 154** |
|---|---|---|
| 1 | 7.31 | 7.20 |
| 2 | 6.91 | 6.92 |
| 3 | 7.07 | 7.04 |
| 7 | 6.41 | 6.45 |
| 9 | 6.37 | 6.34 |
| 1' | 4.57 | 4.48 |
| 2' | 5.34 | 5.16 |
| 4' | 2.05 | 1.94 |
| 5' | 2.07 | 1.94 |
| 6' | 5.08 | 4.48 |
| 8' | 1.96 | 1.94 |
| 9' | 2.05 | 1.94 |
| 10' | 5.07 | 4.48 |
| 12' | 1.66 | 1.56 |
| 1" | 1.73 | 1.71 |
| 2" | 1.60 | 1.41 |
| 3" | 1.57 | 1.37 |
| 1''' | 4.27 | 4.41 |
| 2''' | 2.93 | 3.23 |
| 4''' | 2.65 | 3.27 |
| 5''' | 3.73 | 3.82 |
| 1'''' | 4.22 | 4.41 |
| 2'''' | 2.90 | 3.23 |
| 4'''' | 2.62 | 3.27 |
| 5'''' | 3.71 | 3.82 |

*The $^1$H NMR were measured in methanol-$d_4$
**Measured in $D_2O$ and the signals are board

Example 8

Farnesyl Side Chain Modifications a) Synthesis and Structural Elucidation of Compound 46

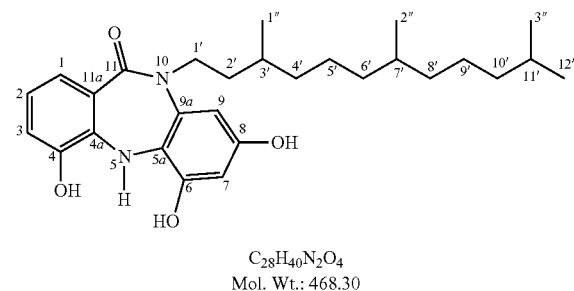

C$_{28}$H$_{40}$N$_2$O$_4$
Mol. Wt.: 468.30

Compound 46: 10-(3,7,11-trimethyldodecyl)-4,6,8-trihydroxy-5,10-dihydro-dibenzo[b,e][1,4]diazepin-11-one, was prepared and identified according to the following procedure:

Preparation:

A solution of Compound 1 (51.1 mg in 3.0 mL MeOH) was stirred under hydrogen gas overnight in presence of platinum oxide (PtO$_2$, 10 mg, 0.4 eq) as a catalyst. The reaction mixture was filtered and purified by direct preparative HPLC using a Phenomenex Synergi™ MAX RP 21.2×200 mm column (20 mL/min, H$_2$O/CH$_3$CN gradient 30:70-30:70, 0-2 min; 30:70-0:100, 2-20 min). Fractions having a retention time of 12.8 min were combined to give 45.2 mg of Compound 46.

Structural Elucidation:

Calculated molecular weight of the major isotope (468.30) and formula (C$_{28}$H$_{40}$N$_2$O$_4$) were confirmed by mass spectral analysis. Compound 46 mass spectra gave a (M−H)$^-$ molecular ion of 467.4 by negative ionization and a (M+H)$^+$ molecular ion of 469.4 by positive ionization. Proton NMR spectral analysis of Compound 46 is shown in Table 12 below. Signals were easily assigned based on Compound 1 structure knowledge. As expected, aliphatic proton signals at positions 2'-11' all have very close chemical shifts ranging from about 1 to 1.75 ppm (integrating for 17 protons), methyl protons at positions 12' and 1''-3'' are all very close as well (shifts 0.8-0.95 ppm, integrating for 12 protons). These signals are also complex from the fact that 2 diastereomers of positions 3' and 7' are present in the mixture, and in different proportions. Labile protons were not observed since NMR was done in deuterated methanol.

b) Synthesis and Structural Elucidation of Compound 78

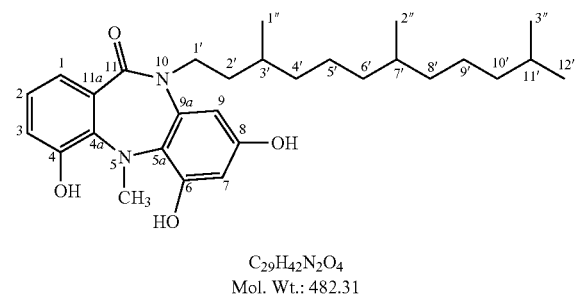

C$_{29}$H$_{42}$N$_2$O$_4$
Mol. Wt.: 482.31

Compound 78, namely 10-(3,7,11-trimethyldodecyl)-4,6,8-trihydroxy-5-methyl-5,10-dihydro-dibenzo[b,e][1,4]diazepin-11-one, was prepared and identified as follows:

Preparation:

A solution of Compound 2 (23.7 mg) in MeOH (2.0 mL) was stirred under hydrogen gas overnight in presence of platinum oxide (PtO$_2$, 10 mg, catalyst) as a catalyst. The reaction mixture was filtered and concentrated in vacuo to give 21.6 mg of Compound 78.

Structural Elucidation:

The calculated molecular weight (482.31) and formula (C$_{29}$H$_{42}$N$_2$O$_4$) of Compound 78 was confirmed by mass spectral analysis: negative ionization gave an (M−H)$^-$ molecular ion of 481.3 and positive ionization gave an (M+H)$^+$ molecular ion of 483.3. The farnesyl olefinic protons on the NMR spectra were replaced by aliphatic proton signals in the region of around 0.76-1.86 ppm, integrating for 17 protons, 3CH, 7CH$_2$. The characteristic N-methyl group (5-N-Me) was easily assigned as shown in Table 12 below.

c) Synthesis and Structural Elucidation of Compound 100

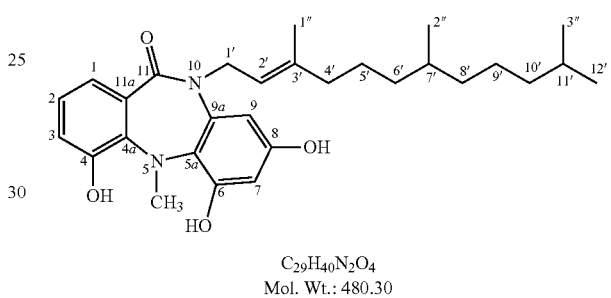

C$_{29}$H$_{40}$N$_2$O$_4$
Mol. Wt.: 480.30

Compound 100, namely 10-(3,7,11-trimethyl-2-dodecenyl)-4,6,8-trihydroxy-5-methyl-5,10-dihydro-dibenzo[b,e][1,4]diazepin-11-one, was prepared and identified as follows:

Preparation:

A solution of Compound 2 (308.5 mg) in MeOH (220 mL) was stirred under hydrogen gas overnight in presence of platinum oxide (PtO$_2$, 10 mg) as catalyst. The reaction mixture was filtered and purified by HPLC according to the procedure described in Example 5(a) to give pure Compound 100 (82.3 mg, RT: 17.0 min).

Structural Elucidation:

The calculated molecular weight (480.30) and formula (C$_{29}$H$_{40}$N$_2$O$_4$) of Compound 100 was confirmed by mass spectral analysis: negative ionization gave an (M−H)$^-$ molecular ion of 479.3 and positive ionization gave an (M+H)$^+$ molecular ion of 481.6. The NMR spectrum analysis was based on the structural elucidation of Compounds 2 and 78. The farnesyl olefinic protons of positions 6'-7' and 10'-11' on the NMR spectra were replaced by aliphatic proton signals and, together with the aliphatic protons of positions 5', 8' and 9', are observed in the region of about 1.07 to 1.51 ppm, integrating for 12 protons, 2CH, 5CH$_2$. The farnesyl olefinic proton at position 2'(CH) was shown on the NMR to have a chemical shift of 5.41 ppm. The methylene group at positions 4' was shown at 2.03 ppm. The characteristic 5-N-methyl group was also easily assigned to a chemical shift of 2.93 ppm.

TABLE 12

$^1$H NMR ($\delta_H$, ppm) Data of Compounds 46, 78 and 100 in $CD_3OD$

| Assignment | 46 | 78 | 100 | Group |
|---|---|---|---|---|
| 1 | 7.15 | 7.18 | 7.21 | CH |
| 2 | 6.76 | 7.12 | 7.14 | CH |
| 3 | 6.84 | 7.01 | 7.02 | CH |
| 5-N—Me | N/A | 2.96, 2.95[b] | 2.93 | $CH_3$ |
| 7 | 6.24 | 6.23 | 6.21 | CH |
| 9 | 6.26 | 6.33, 6.35[b] | 6.34 | CH |
| 1' | 4.16, 3.99 | 4.42, 3.86 | 4.56, 4.87 | $CH_2$ |
| 2'-11'[a] | ~1.00-1.75 | ~0.76-1.86 | c | c |
| 12' and 1"-3"[a] | ~0.8-0.95 | ~0.87-1.00 | d | d |

N/A: not applicable, group not present in the molecule
[a]Signals are very close.
[b]Mixture of isomers.
[c]Compounds 46 and 78: 3CH, 7$CH_2$ (17H); Compound 100: 2'(CH) at 5.41 ppm, 4'($CH_2$) at 2.03 ppm, 5'-11' (12H) at 1.07-1.51 ppm.
[d]Compounds 46 and 78: 4$CH_3$ (12H); Compound 100: 1" ($CH_3$) at 1.75 ppm, 2", 3" and 12' (9H) at 0.88-0.80 ppm.

d) Synthesis and Elucidation of Compounds 17 and 18 by Epoxidation

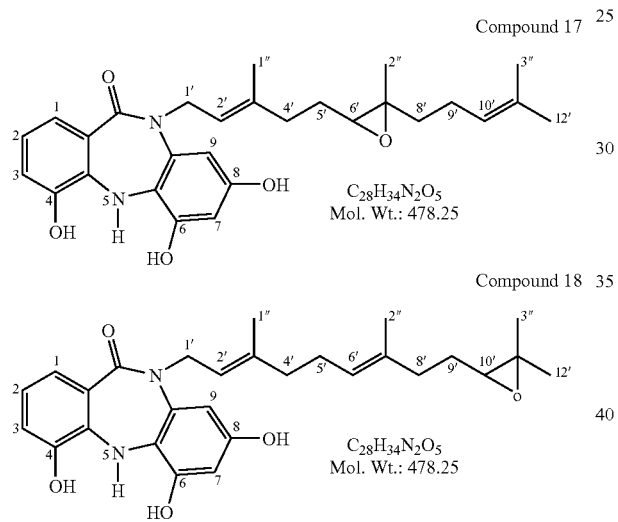

Compound 17
$C_{28}H_{34}N_2O_5$
Mol. Wt.: 478.25

Compound 18
$C_{28}H_{34}N_2O_5$
Mol. Wt.: 478.25

Compound 17: 10-(3,7,11-trimethyl-6,7-epoxydodeca-2,10-dienyl)-4,6,8-trihydroxy-5,10-dihydro-dibenzo[b,e][1,4]diazepin-11-one, and Compound 18: 10-(3,7,11-trimethyl-10,11-epoxydodeca-2,10-dienyl)-4,6,8-trihydroxy-5,10-dihydro-dibenzo[b,e][1,4]diazepin-11-one, were prepared and identified according to the following procedure:

Preparation:
A mixture of Compound 1 (24.0 mg) and 3-chloroperbenzoic acid (mCPBA, 7.8 mg, 0.9 eq) in THF (1.0 mL) were stirred overnight at room temperature. The reaction mixture was diluted with MeOH (1.0 mL) and subjected to purification on Waters HPLC using a Photodiode Array detector. The mixture was purified by multiple injections on a Waters™ RCM Nova-Pak™ HR C-18 25×200 mm column (20 mL/min, $H_2O/CH_3CN$ gradient 80:20-30:70, 0-8 min; 30:70-0:100, 8-20 min). Pure Compound 17 (2.11 mg) and Compound 18 (1.68 mg) were obtained by concentration in vacuo of the combined fractions respectively having retention time 11.2 min and 10.6 min.

Structural Elucidation:
Calculated molecular weights of the major isotopes (478.25) and formulae ($C_{28}H_{34}N_2O_5$) were confirmed by mass spectral analysis. Compound 17 mass spectra gave a (M−H)$^-$ molecular ion of 477.3 by negative ionization and a (M+H)$^+$ molecular ion of 479.4 by positive ionization. Compound 18 mass spectra gave a (M−H)$^-$ molecular ion of 477.3 by negative ionization and a (M+H)$^+$ molecular ion of 479.4 by positive ionization. Proton NMR spectral analysis of Compounds 17 and 18 is shown in Table 13. Signals were easily assigned based on Compound 1 structure knowledge. As expected, epoxide protons signals were shifted upfield, compared to the alkene protons of Compound 1 (from 5.09 to 2.75 ppm for Compound 17, and from 5.06 to 2.73 ppm for Compound 18). Exchangeable protons were not observed as NMR was done in deuterated methanol.

TABLE 13

$^1$H NMR ($\delta_H$, ppm) Data of Compounds 17 and 18 in $CD_3OD$

| Assignment | Compound 17 | Compound 18 | Group |
|---|---|---|---|
| 1 | 7.17 | 7.18 | CH |
| 2 | 6.77 | 6.77 | CH |
| 3 | 6.85 | 6.86 | CH |
| 7 | 6.22 | 6.23 | CH |
| 9 | 6.27 | 6.27 | CH |
| 1' | 4.61, 4.54 | 4.55 | $CH_2$ |
| 2' | 5.42 | 5.37 | CH |
| 4' | 2.17 | 2.08[a] | $CH_2$ |
| 5' | 1.62, 1.42 | 2.13[a] | $CH_2$ |
| 6' | 2.75 | 5.16 | CH |
| 8' | 1.62, 1.42 | 2.08[a] | $CH_2$ |
| 9' | 2.09 | 1.60 | $CH_2$ |
| 10' | 5.09 | 2.73 | CH |
| 12' | 1.67 | 1.26 | $CH_3$ |
| 1" | 1.77 | 1.74 | $CH_3$ |
| 2" | 1.26 | 1.64 | $CH_3$ |
| 3" | 1.60 | 1.20 | $CH_3$ |

[a]Signals are very close, and are interchangeable e) Synthesis and Structural Elucidation of Compound 89 and 92

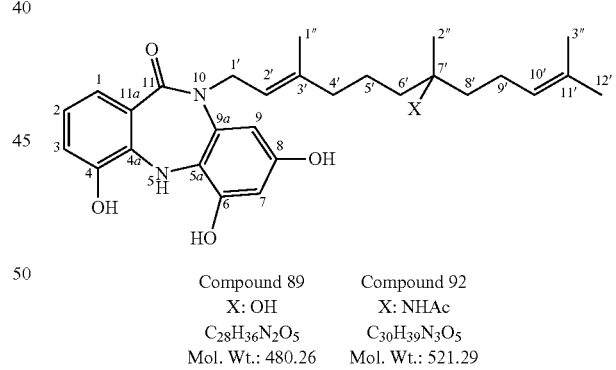

Compound 89
X: OH
$C_{28}H_{36}N_2O_5$
Mol. Wt.: 480.26

Compound 92
X: NHAc
$C_{30}H_{39}N_3O_5$
Mol. Wt.: 521.29

Compound 89, namely 10-(7-hydroxy-3,7,11-trimethyl-dodeca-2,10-dienyl)-4,6,8-trihydroxy-5,10-dihydro-dibenzo[b,e][1,4]diazepin-11-one, and Compound 92, namely 10-(7-acetamido-3,7,11-trimethyl-dodeca-2,10-dienyl)-4,6,8-trihydroxy-5,10-dihydro-dibenzo[b,e][1,4]diazepin-11-one, were prepared and identified as follows:

Preparation:
Compound 1 (20.0 mg) was dissolved in $CH_3CN$ (2.0 mL) and water (50 µL) and PTSA (56.0 mg) was added. The solution was stirred under reflux for 30 min. The reaction mixture was filtered and the filtrate subjected to Waters HPLC purification (multiple injections on Nova-Pack™ HR C-18 25×200 mm column: 20 mL/min, H₂O/CH₃CN gradient 70:30-20:80, 0-4 min; 20:80-0:100, 4-9 min), to give Compound 89 (0.73 mg, RT 10.0 min) and Compound 92 (0.33 mg, RT 10.5 min).

Structure Elucidation of Compounds 89 and 92:

The calculated molecular weight of the major isotope (480.26) and formula ($C_{28}H_{36}N_2O_5$) of Compound 89 was confirmed by mass spectral analysis: negative ionization gave an (M–H)⁻ molecular ion of 479.8 and positive ionization gave an (M+H—H₂O)⁺ molecular ion of 464.1. The characteristic side chain signal (signal 6') aliphatic methylene was easily assigned as shown in Table 14 below.

The calculated molecular weight of the major isotope (521.29) and formula ($C_{30}H_{39}N_3O_5$) of Compound 92 was confirmed by mass spectral analysis: negative ionization gave an (M–H)⁻ molecular ion of 522.8 and positive ionization gave an (M+H)⁺ molecular ion of 522.9. The characteristic side chain (signal 6') aliphatic methylene and the acetamide (signal 7'-NHAc) were easily assigned as shown in Table 14 below.

TABLE 14

¹H NMR ($\delta_H$, ppm) Data of Compounds 89 and 92 in CD₃OD

| Assignment | Compound 89 | Compound 92 | Group |
|---|---|---|---|
| 1 | 7.18 | 7.17 | CH |
| 2 | 6.77 | 6.77 | CH |
| 3 | 6.86 | 6.85 | CH |
| 7 | 6.23 | 6.22 | CH |
| 9 | 6.29 | 6.31 | CH |
| 1' | 4.56 | 4.54 | CH₂ |
| 2' | 5.39 | 5.40 | CH |
| 4' | 2.05 | 2.05 | CH₂ |
| 5', 6', 8', 9' | 1.49-1.27[a] | N/A | 4(CH₂) |
| 5', 6', 8' | — | 1.77-1.40[b] | 3(CH₂) |
| 7'-X | — | 1.92 | X[c] |
| 9' | — | 1.93 | CH₂ |
| 10' | 5.13 | 5.12 | CH |
| 12' | 1.68 | 1.67 | CH₃ |
| 1" | 1.73 | 1.71 | CH₃ |
| 2" | 1.14 | 1.23 | CH₃ |
| 3" | 1.61 | 1.59 | CH₃ |

N/A: not applicable, group not present in the molecule
[a]Signals 5', 6', 8' and 9' of Compound 89 are all very close.
[b]Signals 5', 6' and 8' of Compound 92 are all very close.
[c]In Compound 89, X is OH, in Compound 92, X is NHC(O)CH₃.

f) Synthesis and Structural Elucidation of Compounds 95 and 96 by Ozonolysis

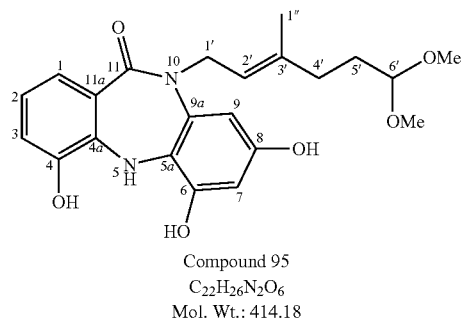

Compound 95
$C_{22}H_{26}N_2O_6$
Mol. Wt.: 414.18

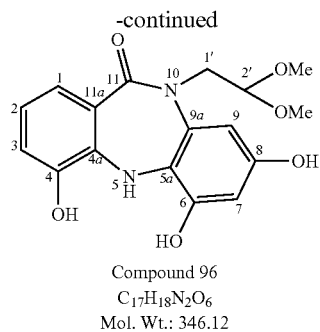

Compound 96
$C_{17}H_{18}N_2O_6$
Mol. Wt.: 346.12

Compound 95, namely 10-(6,6-dimethoxy-3-methyl-2-hexenyl)-4,6,8-trihydroxy-5,10-dihydro-dibenzo[b,e][1,4]diazepin-11-one, and Compound 96, namely 10-(6,6-dimethoxyethyl)-4,6,8-trihydroxy-5,10-dihydro-dibenzo[b,e][1,4]diazepin-11-one, were prepared and identified as follows:

Preparation:

Compound 1 (201.2 mg) was dissolved in MeOH (3.0 mL) and O₃ (ozone) was bubbled in the solution for 2 min at −80° C. (dry ice/acetone). Dimethyl sulfide (146 ml) was added and the reaction mixture was warmed up and stirred at room temperature for 24 hrs. The reaction mixture was filtered and the filtrate subjected to purification on a Waters Auto-Purification System (multiple injections on YMC-Pack ODS-AQ column 20×250 mm: 20 mL/min, H₂O/CH₃CN gradient: 75:25 isocratic 3 min, 75:25-5:95, 3-30 min; 5:95-0:100, 30-31 min and 100% CH₃CN isocratic for 5 min), to give Compound 95 (0.96 mg, RT 12.4 min) and Compound 96 (1.23 mg, RT 8.7 min).

Structural Elucidation of Compounds 95 and 96:

The calculated molecular weight of the major isotope (414.18) and formula ($C_{22}H_{26}N_2O_6$) of Compound 95 was confirmed by mass spectral analysis: negative ionization gave an (M–H)⁻ molecular ion of 413.4 and positive ionization gave an (M+Na)⁺ molecular ion of 437.6. The characteristic farnesyl side chain proton NMR signals (7' to 11', and 2", 3") were replaced by an aliphatic carbon (signal 6') and two methoxy groups (6'-OMe's), easily assigned as shown in Table 15 below.

The calculated molecular weight of the major isotope (346.12) and formula ($C_{17}H_{18}N_2O_6$) of Compound 96 was confirmed by mass spectral analysis: negative ionization gave an (M–H)⁻ molecular ion of 345.2 and positive ionization gave an (M+Na)⁺ molecular ion of 369.3. The characteristic farnesyl side chain proton NMR signals were replaced by aliphatic carbon (signal 2') and two methoxy groups (2'-OMe's), easily assigned as shown in Table 15 below.

TABLE 15

¹H NMR ($\delta_H$, ppm) Data of Compounds 95 and 96 in CD₃OD

| Assignment | Compound 95 | Compound 96 | Group |
|---|---|---|---|
| 1 | 7.18 | 7.15 | CH |
| 2 | 6.77 | 6.77 | CH |
| 3 | 6.86 | 6.86 | CH |
| 7 | 6.23 | 6.24 | CH |
| 9 | 6.27 | 6.41 | CH |
| 1' | 4.58 | 4.64 | CH₂ |
| 2' | 5.35 | 4.72 | CH |
| 2'-OMe | N/A | 3.40 | 2 × OCH₃ |
| 4' | 2.07 | N/A | CH₂ |

TABLE 15-continued $^1$H NMR ($\delta_H$, ppm) Data of Compounds 95 and 96 in CD$_3$OD

| Assignment | Compound 95 | Compound 96 | Group |
|---|---|---|---|
| 5' | 1.66 | N/A | CH$_2$ |
| 6' | 4.22 | N/A | CH |
| 6'-OMe | 3.37 | N/A | 2 × OCH$_3$ |
| 1''' | 1.74 | N/A | CH$_3$ |

N/A: not applicable, group not present in the molecule

Example 9

Aromatic Substitution Reaction a) Synthesis and Structural Elucidation of Compound 97 by Bromination

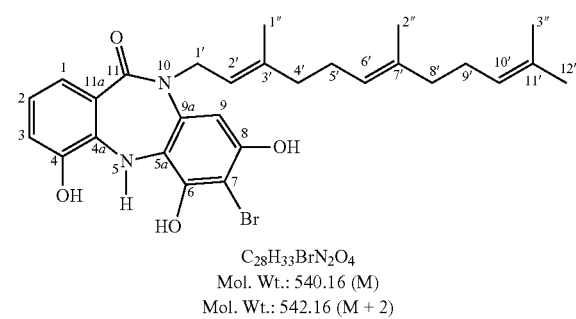

C$_{28}$H$_{33}$BrN$_2$O$_4$
Mol. Wt.: 540.16 (M)
Mol. Wt.: 542.16 (M + 2)

Compound 97: 10-(farnesyl)-7-bromo-4,6,8-trihydroxy-5,10-dihydro-dibenzo[b,e][1,4]diazepin-11-one, was prepared and identified according to the following procedure:

Preparation:

Compound 1 (116.0 mg) and N-bromosuccinimide (NBS, 45.5 mg) were dissolved in tetrahydrofuran (THF, 3.0 mL) and stirred at room temperature for 4 days. The reaction mixture was filtered and subjected to Waters HPLC purification (Nova-Pack™ HR C-18 25×200 mm column: 20 mL/min, H$_2$O/CH$_3$CN gradient 80:20-30:70, 0-8 min; 30:70-0:100, 8-18 min) to give Compound 97 (13.6 min) together with some impurities. The semi-purified sample was further purified by HPLC (Symmetry™ C-18 25×100 mm column: 20 mL/min, H$_2$O/CH$_3$CN gradient 70:30-30:70, 0-15 min), to give Compound 97 (9.5 mg, RT 13.0 min).

Structural Elucidation:

The calculated molecular weight of the major isotopes (540.16 and 542.16) and formula (C$_{28}$H$_{33}$BrN$_2$O$_4$) of Compound 97 was confirmed by mass spectral analysis: negative ionization gave (M−H)$^−$ molecular ions of 539.2 and 541.1, and positive ionization gave (M+H)$^+$ molecular ions of 541.3 and 543.2. The presence of the two molecular ions in each mass spectrum confirmed the presence of a bromine group in the molecule. The structure was further confirmed by the absence of the aromatic (7) signal in the proton NMR spectrum as shown in Table 16 below.

TABLE 16

$^1$H NMR ($\delta_H$, ppm) Data of Compound 97 in CD$_3$OD

| Assignment | Compound 97 | Group |
|---|---|---|
| 1 | 7.18 | CH |
| 2 | 6.79 | CH |
| 3 | 6.87 | CH |
| 9 | 6.49 | CH |
| 1' | 4.56 | CH$_2$ |
| 2' | 5.34 | CH |
| 4' | 2.06 | CH$_2$ |
| 5' | 2.09 | CH$_2$ |
| 6' | 5.10 | CH |
| 8' | 1.96 | CH$_2$ |
| 9' | 2.04 | CH$_2$ |
| 10' | 5.08 | CH |
| 12' | 1.66 | CH$_3$ |
| 1'' | 1.74 | CH$_3$ |
| 2'' | 1.60 | CH$_3$ |
| 3'' | 1.57 | CH$_3$ | b) Synthesis and Structural Elucidation of Compounds 155 to 158 and Compounds 159 to 161

Compounds 155 to 158

Preparation of Compound 155 (namely, 7-Bromo-10-(10,11-dibromo-3,7,11-trimethyl-dodeca-2,6-dienyl)-4,6,8-trihydroxy-5,10-dihydro-dibenzo[b,e][1,4]diazepin-11-one) and Compound 156 (namely, 7-Bromo-10-(6,7-dibromo-3,7,11-trimethyl-dodeca-2,10-dienyl)-4,6,8-trihydroxy-5,10-dihydro-dibenzo[b,e][1,4]diazepin-11-one): Compound 1 (1.08 g) was dissolved in tetrahydrofuran (10.0 mL) and stirred at room temperature for 4 days with N-bromosuccinimide (675 mg). The reaction mixtures than subjected for Sephadex LH-20 column (3.5×100 cm) eluting with MeOH (10 mL/fraction). Fraction 41-58 were pooled and concentrated under reduced pressure. The combine fraction was filtered through a Waters GHP 0.45 □m filter and the filtrate was subjected to HPLC purification. Multiple injections on an Nova Pack C-18 25×200 mm column (20 mL/min, H$_2$O/CH$_3$CN 3:7 isocratic) yielded Compound 155 (41.4 mg) and Compound 156 (10.5 mg) eluting at 9.2, 11.8 and 13.0 minutes, respectively.

Compound 155 was calculated to have a molecular weight of 701.28, and to have a formula of C$_{28}$H$_{33}$Br$_3$N$_2$O$_4$.

Compound 155

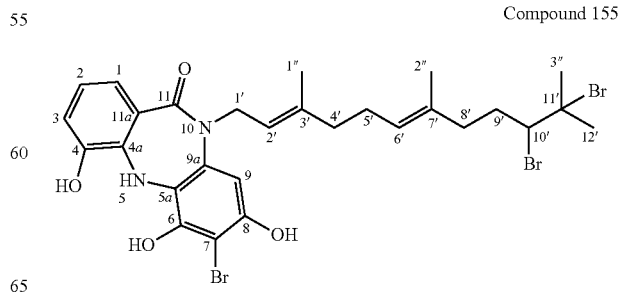

Compound 156 was calculated to have a molecular weight of 701.28, and to have a formula of $C_{28}H_{33}Br_3N_2O_4$.

Compound 156

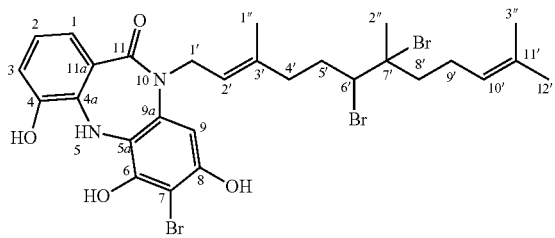

Preparation of Compound 157 (namely, 7-Bromo-4,6,8-trihydroxy-10-(3,7,11-trimethyl-dodecyl)-5,10-dihydro-dibenzo[b,e][1,4]diazepin-11-one): Compound 97 (15.0 mg) was dissolved in MeOH (2.0 mL) and stirred at room temperature overnight under hydrogen having Platinum oxide ($PtO_2$, 5.0 mg). The reaction mixture was filtered through a Waters GHP 0.45 μm filter and the filtrate was subjected to HPLC purification. Multiple injections on a Nova Pack C-18 25×200 mm column (20 mL/min, $H_2O/CH_3CN$ gradient 80:20-30:70, 0-8 min; 30:70-0:100, 5-18 min and 100% $CH_3CN$ till 24 min) yielded Compound 157 (5.0 g) eluting at 17.8 min.

Compound 157 was calculated to have a molecular weight of 547.52, and to have a formula of $C_{28}H_{39}BrN_2O_4$.

Compound 157

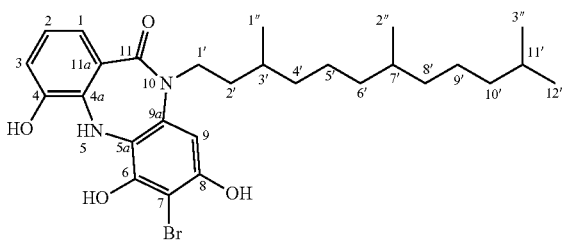

Preparation of Compound 158 (namely, 4,6,8-Trihydroxy-7-iodo-10-farnesyl-5,10-dihydro-dibenzo[b,e][1,4]diazepin-11-one): Compound 1 (24.7 mg) was dissolved in tetrahydrofuran/carbontetrachloride (1:1, 2.0 mL) and stirred at room temperature for 4 days with N-iodiosuccinimide (23.3 mg). The reaction mixture was filtered through a Waters GHP 0.45 μm filter and the filtrate was subjected to HPLC purification. Multiple injections on a Nova Pack C-18 25×200 mm column (20 mL/min, $H_2O/CH_3CN$ 3:7 isocratic) yielded Compound 158 (3.0 mg) eluting at 7.4 minutes.

Compound 158 was calculated to have a molecular weight of 588.48, and to have a formula of $C_{28}H_{33}IN_2O_4$.

Compound 158

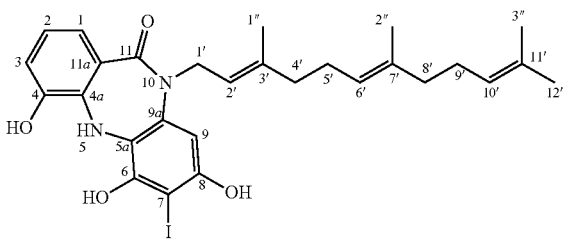

The structure of Compounds 155, 156, 157 and 158 were confirmed by proton NMR, the data for which is presented in Table 16i below.

TABLE 16i $^1$H NMR data of Compounds 155 to 158*

| Assignment | Compound 155 | Compound 156 | Compound 157 | Compound 158 |
|---|---|---|---|---|
| 1 | 7.18 | 7.18 | 7.16 | 7.17 |
| 2 | 6.79 | 6.78 | 6.78 | 6.78 |
| 3 | 6.87 | 6.87 | 6.86 | 6.86 |
| N—Me | — | — | — | — |
| 7 | — | — | — | — |
| 9 | 6.49 | 6.48 | 6.47 | 6.48 |
| 1' | 4.56 | 4.65, 4.53 | 4.17, 4.00 | 4.54 |
| 2' | 5.37 | 5.48 | ** | 5.33 |
| 4' | 2.08 | 2.37, 2.26 | ** | 2.05 |
| 5' | 2.14 | 2.55, 1.88 | ** | 2.07 |
| 6' | 5.22 | 4.19 | ** | 5.09 |
| 8' | 2.32, 2.17 | 2.04, 1.91 | ** | 1.96 |
| 9' | 2.48, 1.82 | 2.25, 2.17 | ** | 2.05 |
| 10' | 4.16 | 5.14 | ** | 5.09 |
| 12' | 1.93 | 1.70 | 0.89 | 1.60 |
| 1" | 1.75 | 1.77 | 0.90 | 1.73 |
| 2" | 1.64 | 1.79 | 0.85 | 1.60 |
| 3" | 1.76 | 1.63 | 0.83 | 1.57 |

*The $^1$H NMR were measured in methanol-$d_4$
**Overlap signals from 163-1.06 ppm Compounds 159 to 161

Preparation of Compound 159 (namely, 9-Chloro-4,6,8-trihydroxy-10-farnesyl-5,10-dihydro-dibenzo[b,e][1,4]diazepin-11-one): Compound 1 (30.0 mg) was dissolved in tetrahydrofuran (2.0 mL), 2 drops of hydrochloric acid (HCl) was added and the solution was stirred at room temperature for 48 hrs. The reaction mixture was filtered through a Waters GHP 0.45 μm filter and the filtrate was subjected to HPLC purification. Multiple injections on an ACE C-18 21×250 mm column (20 mL/min, $H_2O/CH_3CN$ gradient 95:5-00:100, 0-20 min) yielded Compound 159 (19.0 mg) eluting at 10.1 min.

Compound 159 was calculated to have a molecular weight of 497.03, and to have a formula of $C_{28}H_{33}ClN_2O_4$ Compound 159

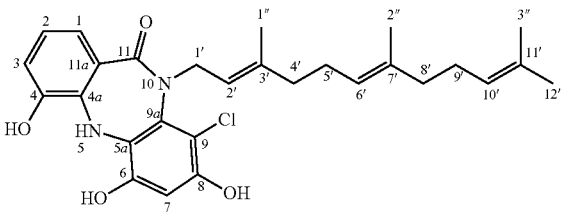

Preparation of Compound 160 (namely, 4,6,8-Trihydroxy-7-(tetrahydro-furan-2-yl)-10-farnesyl-5,10-dihydro-dibenzo[b,e][1,4]diazepin-11-one): Compound 1 (500.0 mg) was dissolved in tetrahydrofuran (40.0 mL). p-Toluene sulfonic acid (p-TsOH, 400 mg) was added and the solution was refluxed for 6 hrs. The reaction mixture was filtered through a Waters GHP 0.45 μm filter and the filtrate was subjected to HPLC purification. Multiple injections on an ACE C-18 21×250 mm column (20 mL/min, $H_2O/CH_3CN$ gradient 50:50-00:100, 0-20 min) yielded Compound 160 (140.0 mg) eluting at 16.2 min.

Compound 160 was calculated to have a molecular weight of 532.67, and to have a formula of $C_{32}H_{40}N_2O_5$.

Compound 160

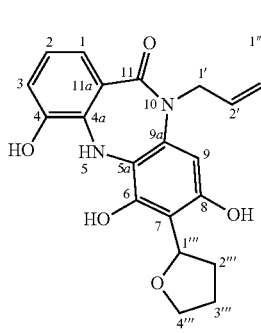

Preparation of Compound 161 (namely, 4,6,8-Trihydroxy-7-(4-hydroxy-1-methoxy-butyl)-10-farnesyl-5,10-dihydro-dibenzo[b,e][1,4]diazepin-11-one): Compound 160 (10.0 mg) was dissolved in methanol/5N HCl in water (8:2, 2.0 mL) and the solution was refluxed for 30 min. The reaction mixture was filtered through a Waters GHP 0.45 μm filter and the filtrate was subjected to HPLC purification. Multiple injections on an ACE C-18 21×250 mm column (20 mL/min, $H_2O$/MeOH gradient 50:50-00:100, 0-15 min) yielded Compound 161 (3.0 mg) eluting at 15.1 min.

Compound 161 was calculated to have a molecular weight of 564.71, and to have a formula of $C_{33}H_{44}N_2O_6$.

Compound 161

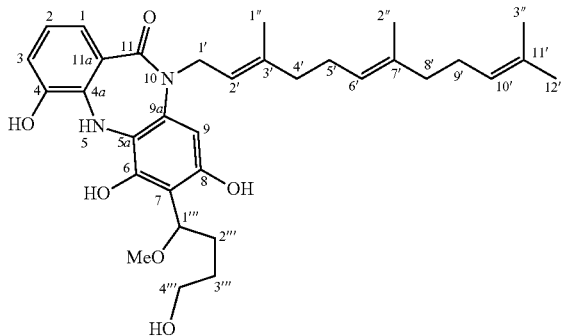

The structure of Compounds 159, 160 and 161 was confirmed by proton NMR, the data for which is presented in Table 16ii below.

TABLE 16ii $^1$H NMR data of Compound 159, Compound 160 and Compound 161*

| Assignment | Compound 159 | Compound 160 | Compound 161 |
|---|---|---|---|
| 1 | 7.16 | 7.17 | 7.18 |
| 2 | 6.80 | 6.77 | 6.78 |
| 3 | 6.85 | 6.86 | 6.86 |
| 7 | 6.48 | — | — |
| 9 | — | 6.29 | 6.33 |
| 1' | 4.99, 4.20 | 4.55 | 4.55 |
| 2' | 5.20 | 5.34 | 5.36 |
| 4' | 1.95 | 2.05 | 2.05 |
| 5' | 2.04 | 2.08 | 2.09 |
| 6' | 5.07 | 5.09 | 5.12 |
| 8' | 1.95 | 1.96 | 1.97 |
| 9' | 1.95 | 2.05 | 2.05 |
| 10' | 5.06 | 5.09 | 5.09 |
| 12' | 1.61 | 1.67 | 1.66 |
| 1" | 1.66 | 1.73 | 1.74 |
| 2" | 1.59 | 1.60 | 1.61 |
| 3" | 1.57 | 1.58 | 1.58 |
| 1'" | — | 5.20 | 4.83 |
| 2'" | — | 2.47 | 2.69 |
| 3'" | — | 2.05 | 2.05 |
| 4'" | — | 4.18, 3.19 | 3.56 |
| 1'"-OMe | — | — | 3.40 |

*The $^1$H NMR were measured in methanol-$d_4$

Example 10

In Vitro Profiling of the Compounds of the Invention (a) In Vitro Anticancer Activity of the Compounds of Formula I Against Four Cell Lines:

In vitro cytotoxic activities of exemplified Compounds are shown in Table 17, along with hemolytic activity of each compound. Compounds were tested in four cell lines: HT-29 (colorectal carcinoma), SF268 (CNS), MDA-MB-231 (mammary gland adenocarcinoma) and PC-3 (prostate adenocarcinoma). Procedures used for each series of tests are described below.

TABLE 17

In vitro Cytotoxic Activities

| Compound No: | HT-29 ($GI_{50}$ μM) | SF-268 ($GI_{50}$ μM) | PC-3 ($GI_{50}$ μM) | MDA-MB-231 ($GI_{50}$ μM) | Average[c] ($GI_{50}$ μM) |
|---|---|---|---|---|---|
| 1[a/b] | 11.2/9.33 | 1.96/1.55 | 1.95/3.76 | 1.79/3.18 | 4.23/4.45 |
| 2[b] | 0.65 | 0.12 | 0.45 | 0.24 | 0.36* |
| 3[a] | 7.3 | 5.73 | 5.36 | 6.32 | 6.18 |
| 4[a] | 14.7 | 4.97 | 5.86 | 11.3 | 9.20 |
| 5[a] | 14.4 | 13.4 | 15.6 | 20.5 | 16.0 |
| 6[a] | >30 | 18.9 | 19.0 | 24.6 | 20.8 |
| 7[a] | 14.1 | 18.5 | 14.6 | 17.4 | 16.1 |
| 9[a] | 12.6 | 1.88 | 1.44 | 2.48 | 4.60 |
| 10[a] | 13.0 | 2.02 | 1.35 | 1.55 | 4.48 |
| 11[a] | 16.0 | 5.79 | 5.35 | 7.72 | 8.72 |
| 12[a] | 9.33 | 1.95 | 1.2 | 2.79 | 3.82* |
| 14[b] | 2.04 | 0.76 | 1.15 | 2.16 | 1.53* |
| 17[b] | >30 | 13.4 | 18.7 | >30 | 16.0 |
| 18[b] | >30 | 7.45 | >30 | >30 | — |
| 46[a] | 4.26 | 0.72 | 0.90 | 0.59 | 1.62* |
| 63[b] | 2.57 | 0.89 | 1.25 | 2.27 | 1.74* |
| 64[b] | 2.5 | 0.56 | 1.14 | 1.39 | 1.40* |
| 67[b] | 2.44 | 0.53 | 1.33 | 1.92 | 1.55* |
| 77[b] | 13.9 | 3.31 | 17.1 | 5.62 | 9.98 |
| 78[b] | 0.29 | 0.07 | 0.23 | 0.24 | 0.21* |
| 80[b] | 1.43 | 0.33 | 1.80 | 1.02 | 1.14* |
| 82[b] | 23.6 | 4.75 | 13.4 | 11.0 | 13.2 |
| 83[b] | 19.6 | 9.74 | 13.2 | 6.71 | 12.3 |
| 84[b] | 21.5 | 3.49 | 16.4 | 23.5 | 16.2 |
| 85[b] | 1.89 | 1.73 | 1.08 | 2.19 | 1.72* |
| 87[b] | 1.83 | 0.91 | 1.39 | 2.40 | 1.63* |
| 89[b] | >30 | 13.7 | 13.5 | 25.3 | 17.5 |
| 92[b] | >30 | 13.5 | 16.6 | 11.1 | 13.7 |
| 97[b] | 2.02 | 2.04 | 1.19 | 2.02 | 1.82* |
| 98[b] | 0.69 | 0.16 | 0.82 | 0.51 | 0.54* |

TABLE 17-continued

In vitro Cytotoxic Activities

| Compound No: | HT-29 (GI$_{50}$ μM) | SF-268 (GI$_{50}$ μM) | PC-3 (GI$_{50}$ μM) | MDA-MB-231 (GI$_{50}$ μM) | Average[c] (GI$_{50}$ μM) |
|---|---|---|---|---|---|
| 100[b] | 0.69 | 0.23 | 0.65 | 0.37 | 0.49* |
| 101[b] | 18.2 | 3.27 | 8.73 | 3.67 | 8.47 |
| 105[b] | >30 | 28.2 | >30 | >30 | 28.2 |

[a]Results obtained by method (a) below
[b]Results obtained by method (b) below
[c]Values > 30 are not considered for calculation of averages;
*shows GI$_{50}$ values lower than Compound 1

All compounds described in Table 17 exhibited anticancer activity. The compounds bearing an asterisk (*) were shown to have a better anticancer activity than Compound 1. These compounds include Compounds 2, 63, 64, 67, 78, 80, 85, 87, 98, and 100 which are N-linear alkyl derivatives of Compound 1, encompassed by Formula II, and their hydrogenated and hydroalkoxylated farnesyl derivatives. The hydrogenated farnesyl derivative Compound 46, brominated aryl derivative Compound 97, and triacetylated Compound 12 were also found to be generally more active than Compound 1.

Method (a):

Cytotoxic activities were determined in vitro for Compounds 1, 3-7, 9-12 and 46 to determine the concentration of each compound needed to obtain a 50% inhibition of cell proliferation (GI$_{50}$). The GI$_{50}$ value emphasizes the correction for the cell count at time zero and, using the seven absorbance measurements [time zero, (Tz), control growth, (C), and test growth in the presence of drug at the five concentration levels (Ti)], GI$_{50}$ is calculated as [(Ti−Tz)/(C−Tz)]×100=−50, which is the drug concentration resulting in a 50% reduction in the net DNA content in treated relative to control cells during the drug incubation.

Compounds were dissolved at 10 mM in DMSO. Dilution in vehicle to concentrations of 30, 10, 3, 1 and 0.3 μM were prepared immediately before assays. Depending on the cell line's growth characteristics, 4000-10000 cells were plated in two 96-wells plates (day 0) and incubated for 16 hours. The following day, propidium iodide was added to one of the two plates and fluorescence measured (Tz). Test compounds were added to the second plate, as well as vehicle control, and cells further incubated for 96 hours. Each compound was tested at each concentration and in triplicates. The equivalent cell number was determined after adding propidium iodide by measuring the signal by fluorescence (C for control). GI$_{50}$ results were calculated using the formula above and are shown in Table 17.

Method (b):

In vitro cytotoxic activities (GI$_{50}$) of Compounds 1, 2, 14, 17, 18, 63, 64, 67, 77, 78, 80, 82 to 85, 87, 89, 92, 97, 98, 100, 101, and 105 were determined using propidium iodide (PI) as being the concentration of drug resulting in 50% growth inhibition, and by using the following method.

Two 96-well plates were seeded in duplicate with each cell line at the appropriate inoculation density (HT29: 3,000; SF268: 3,000; PC-3: 3,000; and MDA-MB-231: 7,500 cells) and according to the technical data sheet of each cell line (rows A-G, 75 μL of media per well). Row H was filled with medium only (150 μL, negative control-medium). The plates were incubated at appropriate temperature and CO$_2$ concentration for 24 hrs.

Test Compounds were prepared as 15× stock solutions in appropriate medium and corresponding to 450, 45, 0.45, 0.045, and 0.0045 μM (prepared the day of the experiment). An aliquot of each was diluted 7.5-fold in appropriate test medium to give a set of six 2× concentration solutions (60, 6, 0.6, 0.06, 0.006, and 0.0006 μM). A 75 μL aliquot of each concentration was added to each corresponding well (rows A to F) of the second plate. Row G was filled with 75 μL of medium/0.6% DMSO (negative control-cells). The second plate was incubated at appropriate temperature and CO$_2$ concentration for 96 hrs.

First Plate: PI (30 μL, 50 μg/mL) was added to each well of the first plate without removing the culture medium. The plate was centrifuged (Sorvall Legend-RT, swinging bucket) at 3500 rpm/10 min. Fluorescence intensity (Thermo, Varioskan, $\lambda_{ex}$: 530 nm; $\lambda_{em}$: 620 nm) was measured to give the first measurement, dead cells (DC at T$_0$; before freezing). Two round of Freeze (−80° C.)/Thaw (37° C.) were done. Fluorescence intensity was determined to give the second measure, total cells (TC at T$_0$; after freeze/thaw)

Second plate was processed as the first one, except there were three rounds of freeze/thaw instead of two. First measurement gave the treated dead cells value (TDC), and the second measurement gave the treated total cells value (TTC). Both values were collected for each treated well and control (CTC and CDC).

Each value (DC, TC, TDC, TTC, CTC and CDC) was corrected by removing the background value (medium only) to give the value ($FU_{DC(T=0)}$, $FU_{TC(T=0)}$, $FU_{TDC}$, $FU_{TTC}$, $FU_{CTC}$ and $FU_{CDC}$) used in the calculation of the T/C (%) (Treated/Control) for each concentration. T/C (%) for each concentration is calculated using the following formula:

$$T/C(\%) = \frac{(FU_{TTC} - FU_{TDC}) - (FU_{TC(T=0)} - FU_{DC(T=0)}) \times 100}{(FU_{CTC} - FU_{CDC}) - (FU_{TC(T=0)} - FU_{DC(T=0)})}$$

The GI$_{50}$ value emphasizes the correction for the cell count at time zero for cell survival. The T/C values are transposed in a graph to determine GI$_{50}$ values, the concentration at with the T/C is 50%.

(b) Anticancer Activity Profiling of Compound 2 Against 36 Cell Lines (IC$_{50}$):

Culture conditions and activity evaluations of Compound 2 against 36 cancer cell lines were done as described in Method (a) of Example 10(a), except that results were expressed as the concentration of drug which inhibits 50% of the cell growth (IC$_{50}$, calculated using the formula: [Ti/C]×100=−50). The low micromolar to nanomolar levels of IC$_{50}$ values shown in Table 18 demonstrated a pharmacologically relevant cytotoxic activity of Compound 2 against a variety of 36 tumor types including melanomas, pancreatic, lung, colon, gastric, bladder, renal, CNS, head and neck, prostate, uterus, ovarian and breast carcinomas.

TABLE 18

In vitro profiles of Compound 2 (IC$_{50}$)

| # | Type | Cell line | Origin | Histology in nude mice | IC$_{50}$ (μM) |
|---|---|---|---|---|---|
| 1 | Bladder | T24 | ATCC | transitional cell ca | 0.127 |
| 2 | Bladder | 1218L | Xenograft | urothelial adeno ca | 0.166 |
| 3 | Colon | HCT116 | NCI | adeno ca, pd | 0.156 |
| 4 | Colon | HT29 | NCI | adeno ca, pd | 0.223 |
| 5 | CNS | 498NL | Xenograft | glioblastoma | 0.176 |

TABLE 18-continued

In vitro profiles of Compound 2 (IC$_{50}$)

| # | Type | Cell line | Origin | Histology in nude mice | IC$_{50}$ (μM) |
|---|---|---|---|---|---|
| 6 | CNS | SF268 | NCI | nd | 0.010 |
| 7 | Gastric | 251L | Xenograft | adeno ca, pd | 0.105 |
| 8 | Head & Neck | 536L | Xenograft | hypopharynx ca | 0.181 |
| 9 | Lung | 1121L | Xenograft | large cell ca | 0.125 |
| 10 | Lung | 289L | Xenograft | adeno ca | 1.553 |
| 11 | Lung | 526L | Xenograft | adeno ca | 0.104 |
| 12 | Lung | 629L | Xenograft | adeno ca | 0.164 |
| 13 | Lung | 529L | Xenograft | large cell ca, | 0.127 |
| 14 | Lung | H460 | NCI | large cell ca | 0.366 |
| 15 | Mammary | 401NL | Xenograft | pap adeno ca, wd | 0.194 |
| 16 | Mammary | MCF7 | NCI | mamma ca | 0.276 |
| 17 | Melanoma | 276L | Xenograft | mm, amelanotic | 1.948 |
| 18 | Melanoma | 394NL | Xenograft | mm, amelanotic, pd | 0.020 |
| 19 | Melanoma | 462NL | Xenograft | mm, amelanotic | 0.978 |
| 20 | Melanoma | 514L | Xenograft | mm, melanotic | 0.110 |
| 21 | Melanoma | 520L | Xenograft | mm, melanotic | 0.085 |
| 22 | Ovarian | 1619L | Xenograft | adeno ca, md | 0.579 |
| 23 | Ovarian | 899L | Xenograft | pap serous ca, md | 0.238 |
| 24 | Ovarian | OVCAR3 | NCI | adeno ca, md | 0.139 |
| 25 | Pancreas | 1657L | Xenograft | adeno ca, md | 1.777 |
| 26 | Pancreas | PANC1 | ATCC | nd | 0.125 |
| 27 | Prostate | 22RV1 | ATCC | adeno ca, md | 0.142 |
| 28 | Prostate | DU145 | NCI | adeno ca, md | 0.158 |
| 29 | Prostate | LNCAP | DSMZ | adeno ca, md | 0.485 |
| 30 | Prostate | PC3M | NCI | adeno ca, pd | 0.114 |
| 31 | Pleuramesot. | 1752L | Xenograft | pleuromesothelioma | 1.503 |
| 32 | Renal | 1781L | Xenograft | renal ca | 0.172 |
| 33 | Renal | 393NL | Xenograft | hypernephroma, wd | 0.527 |
| 34 | Renal | 486L | Xenograft | hypernephroma, pd | 1.144 |
| 35 | Renal | 944L | Xenograft | hypernephroma | 0.230 |
| 36 | Uterus | 1138L | Xenograft | carcinosarcoma, wd | 0.139 |
| | | | | Mean of all cell lines: | 0.407 | ca = carcimoma;
pd = poorly differentiated;
pap = papillary;
md = moderately differentiated;
wd = well differentiated;
mm = malignant melanoma;
nd = not determined Example 11

In Vivo Efficacy of Compounds 1 and 2 a) In Vivo Efficacy of Compounds 1 and 2 in a Glioma Model:

The aim of this study was to test whether Compound 1 administered by the i.p. route prevents or delays tumor growth in C6 glioblastoma cell-bearing mice, and to determine an effective dosage regimen.

Animals: A total of 60 six-week-old female mice (*Mus musculus* nude mice), ranging between 18 to 25 g in weight, were observed for 7 days before treatment. Animal experiments were performed according to ethical guidelines of animal experimentation (*Charte du comité d'éthique du CNRS, juillet* 2003) and the English guidelines for the welfare of animals in experimental neoplasia (WORKMAN, P., TWENTYMAN, P., BALKWILL, F., et al. (1998). *United Kingdom Coordinating Committee on Cancer Research* (*UKCCCR*) *Guidelines for the welfare of animals in experimental neoplasia* (Second Edition, July 1997; *British Journal of Cancer*, 77:1-10). Any dead or apparently sick mice were promptly removed and replaced with healthy mice. Sick mice were euthanized upon removal from the cage. Animals were maintained in rooms under controlled conditions of temperature (23±2° C.), humidity (45±5%), photoperiodicity (12 hrs light/12 hrs dark) and air exchange. Animals were housed in polycarbonate cages (5/single cage) that were equipped to provide food and water. Animal bedding consisted of sterile wood shavings that were replaced every other day. Food was provided ad libitum, being placed in the metal lid on the top of the cage. Autoclaved tap water was provided ad libitum. Water bottles were equipped with rubber stoppers and sipper tubes. Water bottles were cleaned, sterilized and replaced once a week. Two different numbers engraved on two earrings identified the animals. Each cage was labeled with a specific code.

Tumor Cell Line: The C6 cell line was cloned from a rat glial tumor induced by N-nitrosomethyurea (NMU) according to Premont et al. (Premont J, Benda P, Jard S., [*3H] norepinephrine binding by rat glial cells in culture. Lack of correlation between binding and adenylate cyclase activation. Biochim Biophys Acta.* 1975 Feb. 13; 381(2):368-76.) after series of alternate culture and animal passages. Cells were grown as adherent monolayers at 37° C. in a humidified atmosphere (5% $CO_2$, 95% air). The culture medium was DMEM supplemented with 2 mM L-glutamine and 10% fetal bovine serum. For experimental use, tumor cells were detached from the culture flask by a 10 min treatment with trypsin-versen. The cells were counted in a hemocytometer and their viability assessed by 0.25% trypan blue exclusion.

Preparation of the Test Article: for the Test Article, the Following Procedure was followed for reconstitution (performed immediately preceding injection). The vehicle consisted of a mixture of benzyl alcohol (1.5%), ethanol (8.5%), propylene glycol (27%), PEG 400 (27%), dimethylacetamide (6%) and water (30%). The vehicle solution was first vortexed in order to obtain a homogeneous liquid. 0.6 mL of the vortexed vehicle solution was added to each vial containing the test article (Compound 1). Vials were mixed thoroughly by vortexing for 1 minute and inverted and shaken vigorously. Vials were mixed again prior to injection into each animal.

Animal Inoculation with tumor cells: Experiment started at day 0 ($D_0$). On $D_0$, mice received a superficial intramuscular injection of C6 tumor cells ($5 \times 10^5$ cells) in 0.1 mL of DMEM complete medium into the upper right posterior leg.

Treatment Regimen and Results:

First Series of Experiments:

In a first series of experiments, treatment started 24 hrs following inoculation of C6 cells. On the day of the treatment, each mouse was slowly injected with 100 μL of test or control articles by the i.p. route. For all groups, treatment was performed until the tumor volume of the saline-treated mice (group 1) reached approximately 3 cm³ (around day 16). Mice of group 1 were treated daily with a saline isosmotic solution for 16 days. Mice of group 2 were treated daily with the vehicle solution for 16 days. Mice of group 3 were treated daily with 10 mg/kg of Compound 1 for 16 days. Mice of group 4 were treated every two days with 30 mg/kg of Compound 1 and received 8 treatments. Mice of group 5 were treated every three days with 30 mg/kg of Compound 1 and received 6 treatments. Measurement of tumor volume started as soon as tumors became palpable (>100 mm³; day 11 post-inoculation) and was evaluated every second day until the end of the treatment using calipers. As shown in Table 19 and FIG. 1, the mean value of the tumor volume of all Compound 1 treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 19 indicates a statistically significant value, while "ns" signifies not significant.

TABLE 19

Compound 1 in vivo antitumor efficacy against C6 glioblastoma

| Treatment | Treatment regimen | Tumor volume (mm³) (mean ± SEM) | % Inhibition | P value |
|---|---|---|---|---|
| Saline | Q1 × 16 | 3,004.1 ± 249.64 | — | — |
| Vehicle solution | Q1 × 16 | 2,162.0 ± 350.0 | 28.0% | >0.05 ns |
| Compound 1 (10 mg/kg) | Q1 × 16 | 1,220.4 ± 283.46 | 59.4% | <0.01 * |
| Compound 1 (30 mg/kg) | Q2 × 8 | 1,236.9 ± 233.99 | 58.8% | <0.01 * |
| Compound 1 (30 mg/kg) | Q3 × 6 | 1,184.1 ± 221.45 | 60.6% | <0.01 * |

Figure 2:
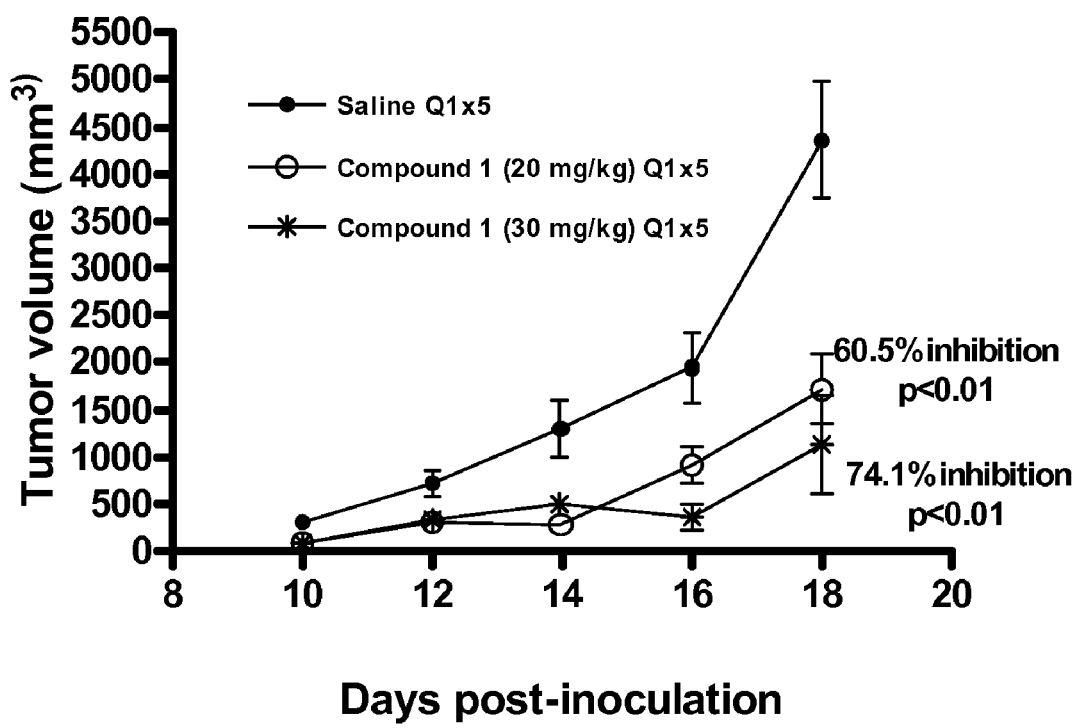
FIG. 2: shows inhibition of tumor growth resulting from bolus administration of 20-30 mg/kg of Compound 1 to glioblastoma-bearing mice ten days after tumor cell inoculation.

Second Series Experiments:

In a second series of experiments, treatment started at day 10 following inoculation of C6 cells when tumors became palpable (around 100 to 200 mm³). Treatment was repeated daily for 5 consecutive days. On the day of the treatment, each mouse was slowly injected with 100 µL of Compound 1 by i.p. route. Mice of group 1 were treated daily with saline isosmotic solution. Mice of group 2 were treated daily with the vehicle solution. Mice of group 3 were treated daily with 20 mg/kg of Compound 1. Mice of group 4 were treated daily with 30 mg/kg of Compound 1. Mice were treated until the tumor volume of the saline-treated control mice (group 1) reached around 4 cm³. Tumor volume was measured every second day until the end of the treatment using calipers. As shown in Table 20 and FIG. 2, the mean value of the tumor volume of all Compound 1 treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 20 indicates a statistically significant value, while "ns" signifies not significant.

Figure 3:
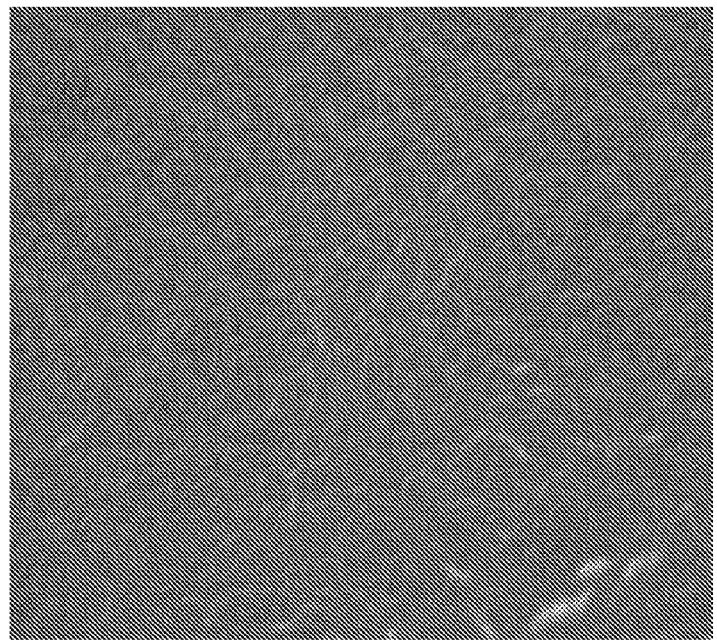
FIG. 3: shows micrographs of tumor sections from mice bearing glioblastoma tumors and treated with saline or Compound 1. The cell density of tumor treated with Compound 1 appears decreased and nuclei from tumor cells are larger and pycnotic suggesting a cytotoxic effect.
Figure 3:
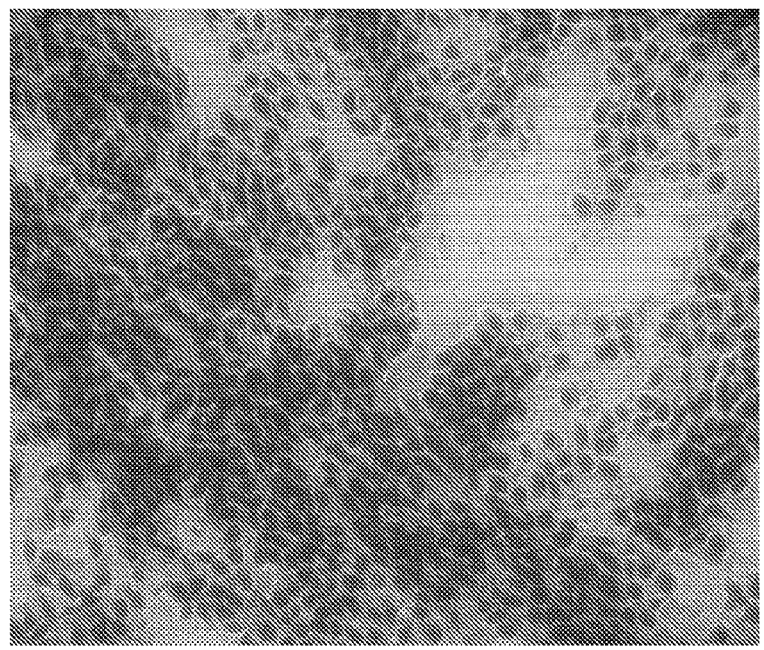

Histological analysis of tumor sections showed pronounced morphological changes between tumors from Compound 1-treated mice and those from mice in the control groups. In tumors from mice treated with Compound 1 (20-30 mg/kg), cell density was decreased and the nuclei of remaining tumor cells appeared larger and pycnotic while no such changes were observed for tumors from vehicle-treated mice (FIG. 3).

TABLE 20

Compound 1 in vivo antitumor efficacy against C6 glioblastoma

| Treatment | Treatment regimen | Tumor volume (mm³) (mean ± SEM) | % Inhibition | P value |
|---|---|---|---|---|
| Saline | Q1 × 5 | 4,363.1 ± 614.31 | — | — |
| Vehicle solution | Q1 × 5 | 3,205.0 ± 632.37 | 26.5% | >0.05 ns |
| Compound 1 (20 mg/kg) | Q1 × 5 | 1,721.5 ± 374.79 | 60.5% | <0.01 * |
| Compound 1 (30 mg/kg) | Q1 × 5 | 1,131.6 ± 525.21 | 74.1% | <0.01 * |

Figure 4:
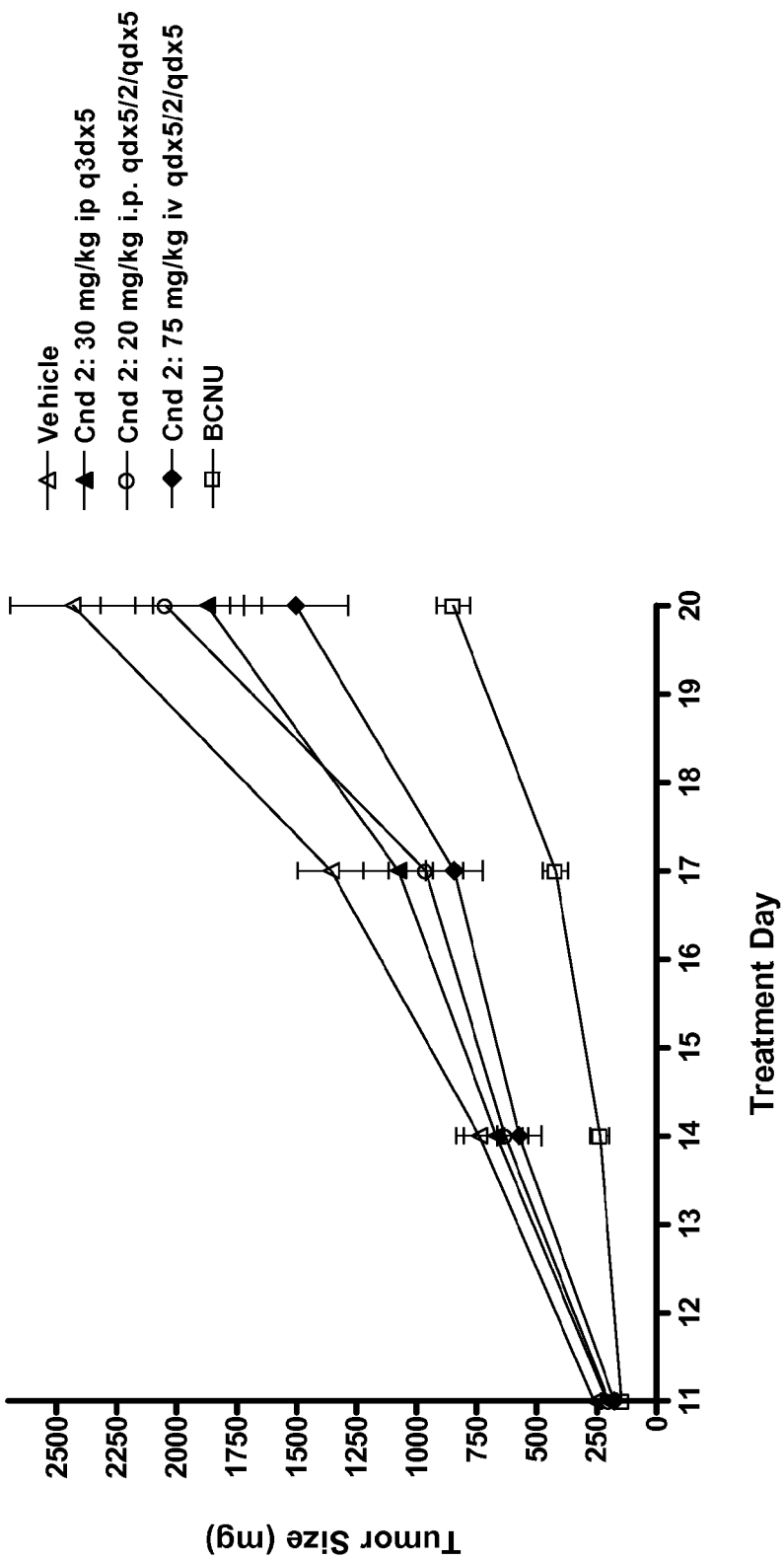
FIG. 4: inhibition of tumor growth resulting from bolus administration of 20 to 75 mg/kg of Compound 2 to C6 glioblastoma-bearing mice from day 11 to day 20 of treatment.

Antitumor Efficacy of Compound 2 against C6 Glioblastoma:

Antitumor efficacy of Compound 2 against rat glioblastoma tumor (C6) xenografts in female swiss nude mice was accomplished as described above. The results and dosage regimen are summarized in FIG. 4. Significant efficacy was shown following intravenous administration, at a dosage regimen of 75 mg/kg (qd5/2/qd5).

Example 12

Pharmacokinetic Profiles

Compounds 1 and 2 were separately dissolved in ethanol (5%), Polysorbate 80 (15%), PEG 400 (5%) and dextrose (5%) at a final concentration of 6 mg/ml (for all parenteral administration routes). For oral administration, Compound 1 was solubilized in Cremophor® EL/Ethanol (50%:50%) at a final concentration of 6 mg/ml. Prior to dosing, animals (female Crl: CD1 mice; 6 weeks of age, 22-24 g) were weighed, randomly selected and assigned to the different treatment groups. Compound 1 was administered by the intravenous (iv), subcutaneous (sc), intraperitoneal (ip), or oral (po) route to the assigned animals. Compound 2 was administered by the intravenous (iv), or intraperitoneal (ip) route to the assigned animals. The dosing volume of Compounds 1 and 2 was 5 mL per kg body weight. Animals were anesthetized with 5% isoflurane prior to bleeding. Blood was collected into microtainer tubes containing the anticoagulant $K_2EDTA$ by cardiac puncture from each of 4 animals per bleeding timepoint (2 min, 5 min, 15 min, 30 min, 1 h, 2 h, 4 h and 8 h). Following collection, the samples were centrifuged and the plasma obtained from each sample was recovered and stored frozen (at approximately −80° C.) pending analysis. At the 5 min and 30 min time points, the following organs were harvested from each animal: brain, lungs, skeletal muscle, fat tissue, kidneys, spleen, thymus and liver. Tissues were frozen (at approximately −80° C.) pending analysis. Samples were analysed by LC/MS/MS. Standard curve ranged from 25 to 2000 ng/mL with limit of quantitation (LOQ)≦25 ng/mL and limit of detection (LOD) of 10 ng/mL.

Plasma values of Compounds 1 and 2 falling below the limit of quantitation (LOQ) were set to zero. Mean concentration values and standard deviation (SD) were calculated at each timepoints of the pharmacokinetic study (n=4 animals/timepoint). The following pharmacokinetic parameters were calculated: area under the plasma concentration versus time curve from time zero to the last measurable concentration time point ($AUC_{0-t}$), area under the plasma concentration versus time curve extrapolated to infinity ($AUC_{inf}$), maximum observed plasma concentration ($C_{max}$), time of maximum plasma concentration ($t_{max}$), apparent first-order terminal elimination rate constant ($k_{el}$), apparent first-order terminal elimination half-life will be calculated as 0.693/kel ($t_{1/2}$). The systemic clearance (CL) of Compound 1 after intravenous administration was calculated using Dose/AUCinf. Pharmacokinetic parameters were calculated using Kinetica™ 4.1.1 (InnaPhase Corporation, Philadelphia, Pa.).

Figure 5:
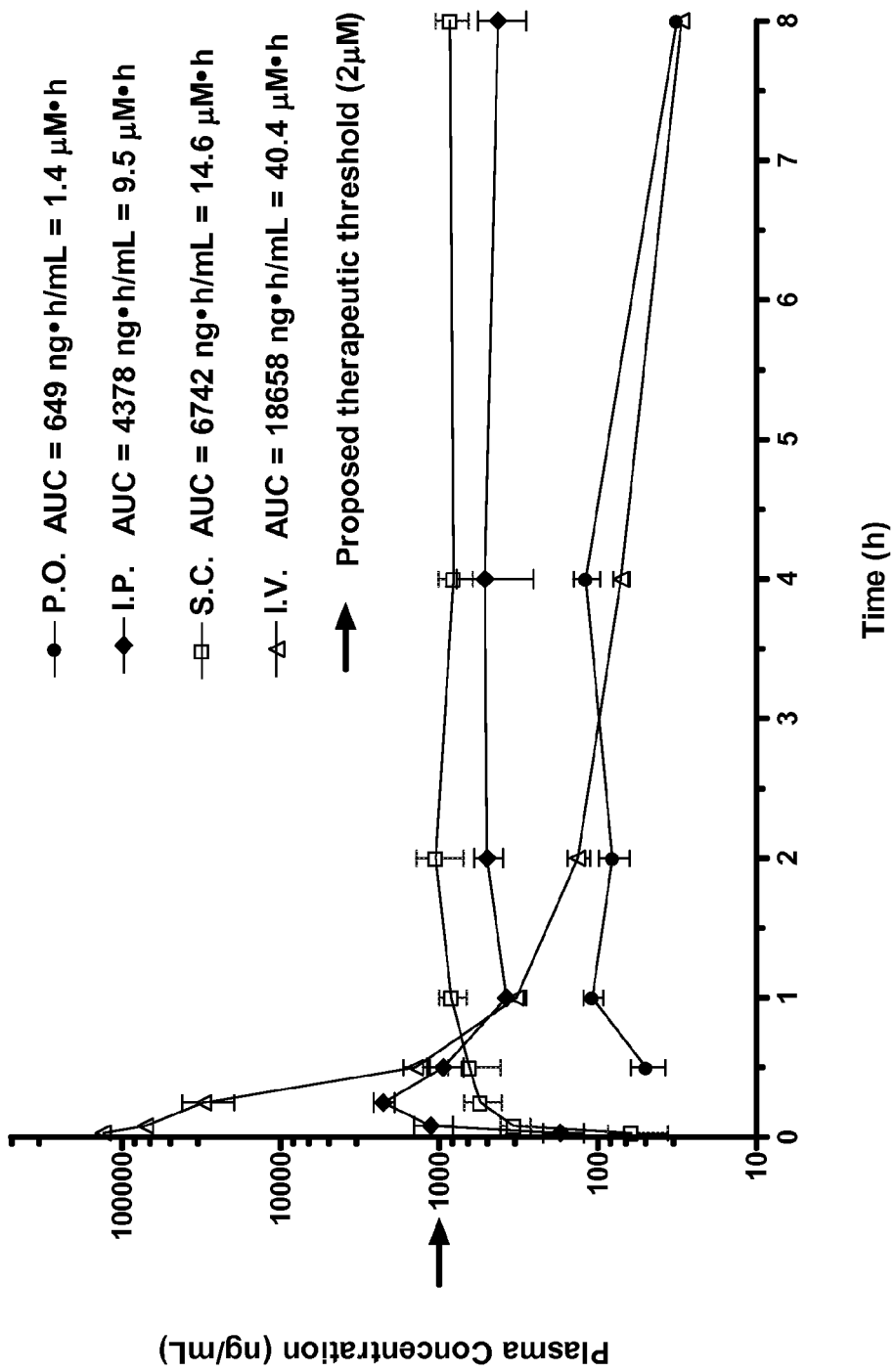
FIG. 5: shows the mean (±SD) plasma concentrations of Compound 1 in Swiss mice following bolus 30 mg/kg intravenous (iv), intraperitoneal (ip), subcutaneous (sc) and oral (po) administrations.
Figure 6:
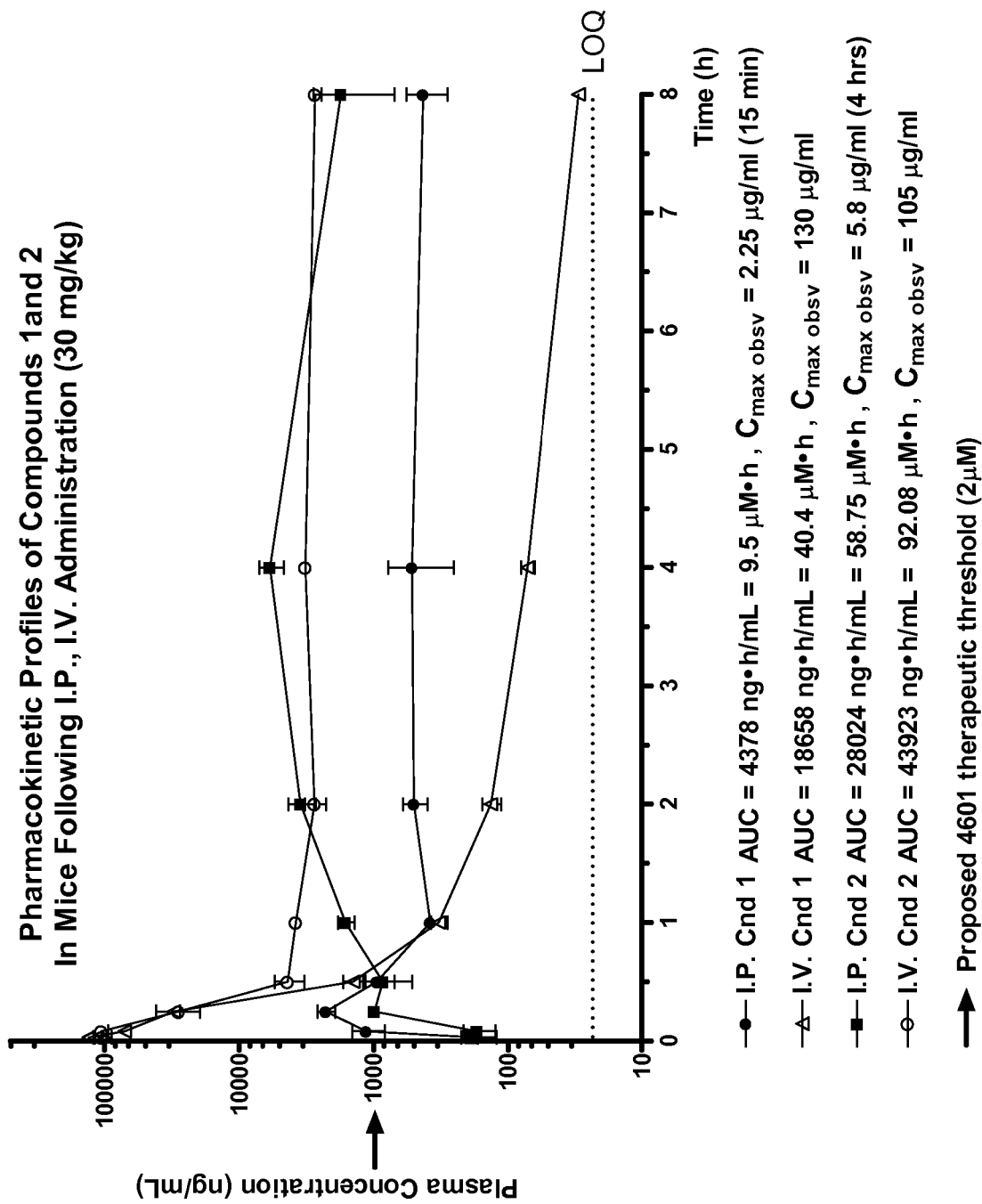
FIG. 6: shows the mean (±SD) plasma concentrations of Compounds 1 and 2 in CD-1 mice following bolus 30 mg/kg intravenous (iv) and intraperitoneal (ip) administrations.

Results:

Mean plasma concentrations of Compound 1 following intravenous (iv), intraperitoneal (ip), subcutaneous (sc), and oral (po) administrations at 30 mg/kg are presented in FIG. 5. Mean plasma concentrations of Compound 2 following iv and ip administrations at 30 mg/kg, compared with Compound 1 via the same routes of administration, are presented in FIG. 6. When administered iv, Compound 2 had an AUC of 92.08 µM·h and an observed $C_{max}$ of 105 µg/mL, compared to an AUC of 40.4 µM·h and an observed $C_{max}$ of 130 µg/mL for Compound 1. When administered ip, Compound 2 had an AUC of 58.75 µM·h and an observed $C_{max}$ of 5.8 µg/mL, compared to an AUC of 9.5 µM·h and an observed $C_{max}$ of 2.25 µg/mL for Compound 1.

Mean (±SD) plasma concentrations of Compound 1 following I.V. administration of a 30 mg/kg dose declined rapidly in a biexponential manner resulting in very short half lives ($t_{1/2}$ α and β of 4.6 min and 2.56 h, respectively). The pharmacokinetics of Compound 1 following intraperitoneal and subcutaneous administrations, and Compound 2 following intraperitoneal and intravenous administration, showed a PK profile suggestive of slow release. With these routes of administration, the compound plasma concentration was sustained and maintained at therapeutically relevant levels for over 8 hours. Compound 2 showed a half life ($t_{1/2}$) of more than 40 hours following both IP and IV administrations. Oral administration of Compound 1 resulted in moderate but sustained drug levels. These data indicated that Compound 1 was orally bioavailable at a 5-8% level.

Figure 7:
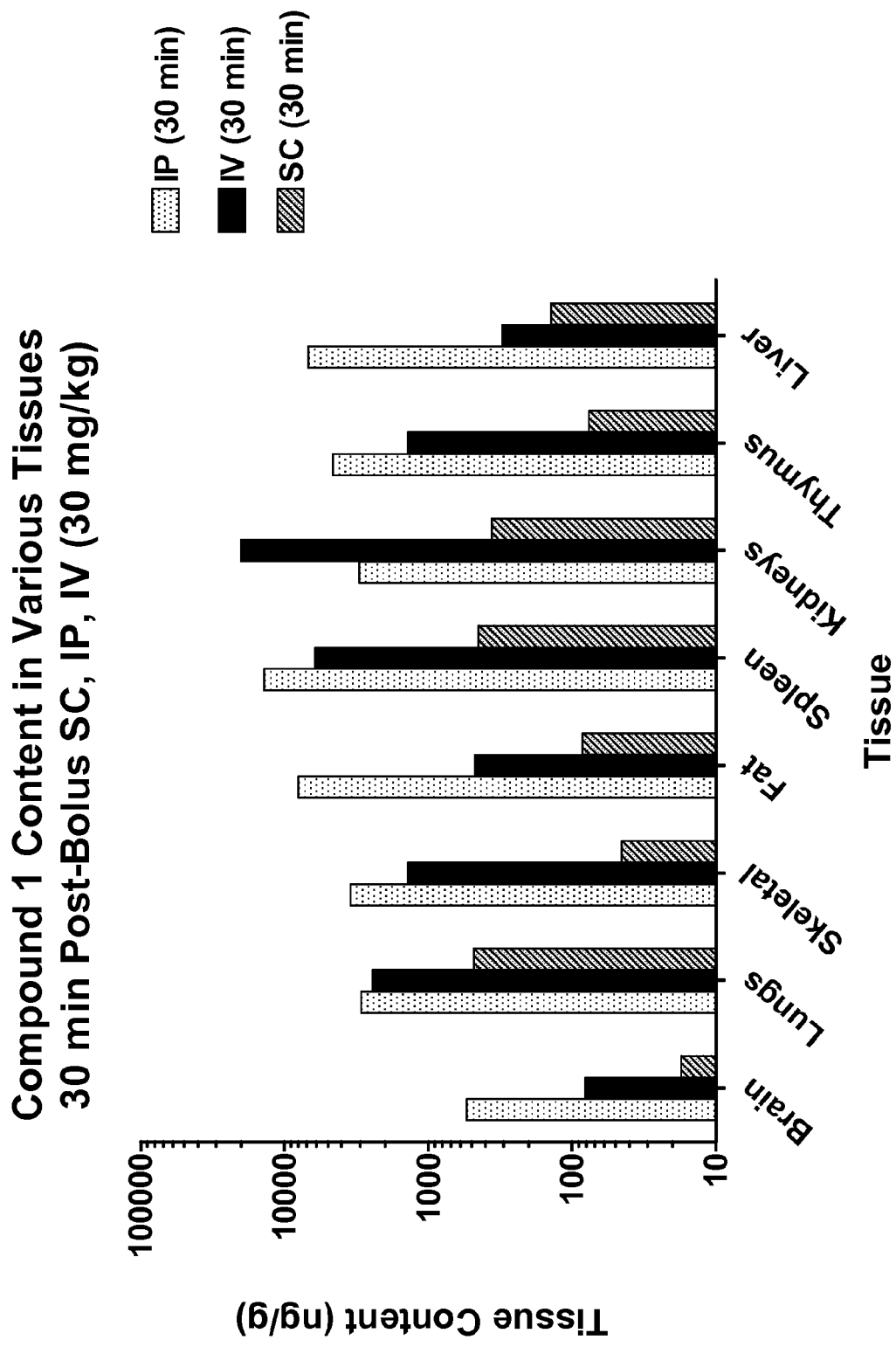
FIG. 7: shows the mean concentration of Compound 1 in various tissues, 30 minutes after 30 mg/kg intravenous (iv), intraperitoneal (ip) and subcutaneous (sc) administrations.

Mean tissue concentrations of Compound 1, 30 min after intravenous (iv), intraperitoneal (ip) or subcutaneous (sc) administrations at 30 mg/kg are presented in FIG. 7. The 30 min time point was chosen since plasma concentrations were similar with all three routes of administration. Compound 1 is well distributed following iv and ip dosing. Surprisingly, although ip and sc administrations resulted in a similar PK profile, tissue levels were significantly lower following sc dosing. This could be explained by the absence of peak levels following sc administration compared with iv and ip administrations.

Acute toxicity studies in CD-1 nu/nu mice for Compound 2, using the same formulation, gave an MTD≧50 mg/kg (ip, NOAEL: 30 mg/kg) and ≧100 mg/kg (iv, NOAEL: 75 mg/kg), with weight losses of about 7% for several days post-injection. Compound 1 had an MTD of 150 mg/kg when administered iv. Acute toxicity studies with Compound 46 gave an MTD of 30 mg/kg (ip).

Example 13

Dibenzodiazepinone Analogs General Procedures a) O-Alkylation:

Alkylation Compounds 4-8 are also produced using the procedure presented in Example 6. Compounds 38 and 39 are also produced using the procedure of Example 6, by controlling the amount of diazomethane, the reaction temperature and/or the reaction time. Compound 38 is also prepared in two steps, from Compound 10, using the procedure of Example 6, the resulting mono-methyl-diacetate compound is subsequently hydrolyzed using aqueous acidic or basic (mild) conditions to obtain Compound 38. Compounds 4, 5, 6, 7 and 39 are also prepared in a similar two-step procedure, when using the appropriate Compound as starting material, which are respectively Compounds 9, 11, 35, 37 and 36.

Syntheses of Compounds 6, 7 and 38 by methylation of Compound 1

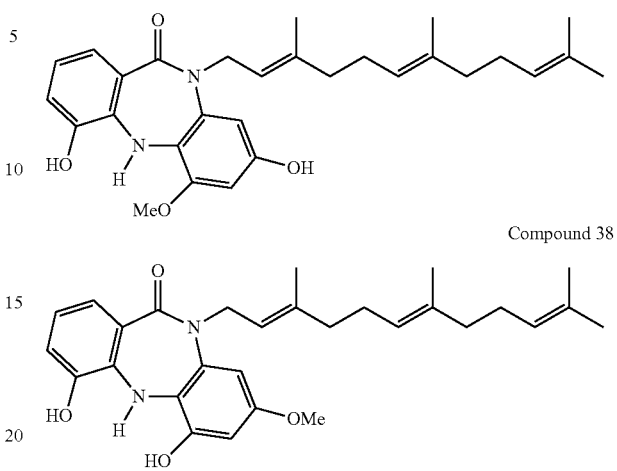

A solution of Compound 1 (1 g) in methanol 50 (ml) is treated with 1.5 equivalents of diazomethane. The mixture is stirred at room temperature for one hour and dried by nitrogen gas stream. The mixture is then redissolved in methanol (10 mL) and poured into a mixture of ethyl acetate (200 ml) and water (200 ml). The layers are separated and the aqueous layer is extracted once more with an equal portion of ethyl acetate. The combined ethyl acetate layers are washed once with 1N aqueous acetic acid and then concentrated to a crude product, which is predominantly a mixture of Compounds 6, 7 and 38 with some starting material and over-methylated derivatives. The desired products may be separated and purified by HPLC or HSCC chromatography or preparative TLC, using the systems as described in any of Examples 2 and 4-9 above, to obtain approximately 200 mg of each of Compounds 6, 7 and 38.

b) O-Acylations:

O-acetylated compounds 35-37 are also produced using the procedures presented in Example 7, using a lower quantity of acetic anhydride, lower temperature, and/or shorter reaction times.

Syntheses of Compounds 35, 36 and 37 by esterification of Compound 1.

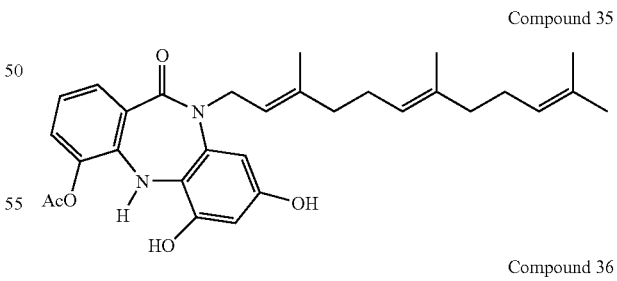

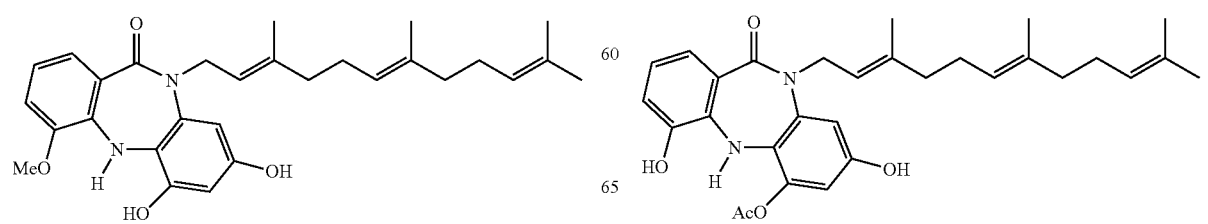

Compound 37

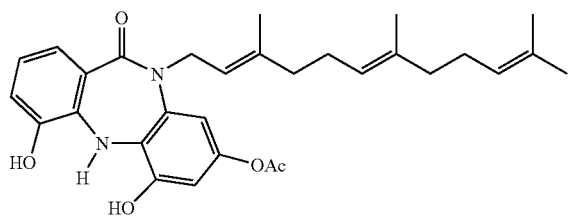

To a solution of Compound 1 dissolved in toluene (9 parts) tetrahydrofuran (1 part), cooled in an ice-bath is added 1.1 equivalents of acetic anhydride and two drops of boron trifluoride etherate. The reaction is maintained cool in an ice bath and stirred at 0° C. for 1-2 hours. The reaction mixture is then poured into aqueous 5% sodium bicarbonate solution shaken and the toluene layer is removed. The aqueous layer is re-extracted with toluene and the combined toluene layers are concentrated to a mixture of predominantly Compounds 35, 36 and 37, contaminated with some unchanged starting material and some diacetates. Compounds 35, 36 and 37 are separated and purified by HPLC or HSCC using one of the systems described in Examples 2 and 4-9. In a typical experiment yields of 25% to 30% are obtained for each of Compounds 35, 36 and 37.

Compounds 9-12 are also produced using the same procedure, with appropriate numbers of molar equivalents (2.2 and 3.3).

c) N-alkylations:

N-Alkylations are accomplished using either an alkyl halide (iodide, bromide, chloride) or another alkylating agent, such as a dialkylsulfate, or an alkylsulfonate (triflate, mesylate, tosylate, and the like). Compounds 2, 3, 14, and 60 to 77 are also produced using the procedures exemplified in Examples 4 and 5.

Syntheses of Compounds 2, 3 and 14 by N-alkylation of Compound 1.

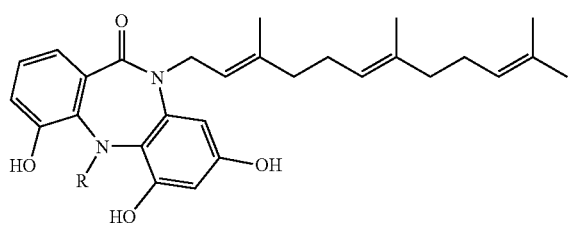

Compound 2   R = methyl
Compound 3   R = benzyl
Compound 14  R = ethyl

To a solution of Compound 1 (50 mg) dissolved in an excess of the appropriate alkyl halide (iodomethane for Compound 2, benzyl chloride for Compound 3 or ethyl bromide for Compound 14) is added a few drops of pyridine (catalytic amount). The reaction mixture is stirred for 72 hours, or refluxed for 1 to 2 hours, and then evaporated to dryness under reduced pressure to obtain Compound 2, 3 or 14 respectively, in an essentially pure form in an almost quantitative yield. The crude compound is further purified by HPLC or Preparative TLC, using the procedures described in Examples 2 and 4-9.

Compounds 60 to 77 are also prepared via this procedure, or the procedures of Example 5, by reaction of Compound 1 respectively with 3-chloro-1-butene, 1-chloro-2-methylpropane, crotylchloride, 1-bromopropane, 1-bromobutane, 1-bromo-2-methylbutane, 2-chloro-2-methylpropane, 1-bromohexane, 1-chlorooctane, trifluoromethyl iodide, heptafluoro-1-iodopropane, heptafluoro-2-iodopropane, 2-iodo-1,1,1-trifluoroethane, bromocyclopropane, 1-chloro-3-phenylpropane, and 2-bromobutane. Compound 78 is also prepared by this procedure, by reacting Compound 46 with iodomethane.

Compounds 60 to 77 are also prepared by the procedures of Example 4, by reaction of Compound 1 with their respective dialkylsulfate (or alkylsulfonate), which is either commercially available or can be prepared, for example by the reaction of the appropriate alcohol with a activated sulfate or sulfonate (e.g. chloride, anhydride, and the like). As an example, 1-hexane triflate is prepared just prior to use by the reaction of 1-hexanol with trifluoromethanesulfonic anhydride (Tf$_2$O) in tetrahydrofuran, using an equimolar amount (vs Tf$_2$O) of base, such as triethylamine. The reaction is worked up by careful treatment with water (containing 1% triethylamine), extracted with ether, dried with magnesium sulfate and concentrated in vacuo. Other examples of procedures for the preparation of alkyl sulfates and sulfonates are described in *Advanced Organic Chemistry*, Jerry March, supra (e.g. page 404).

d) N-Acylation:

Synthesis of Compound 13 by N-acetylation of Compound 1.

Compound 13

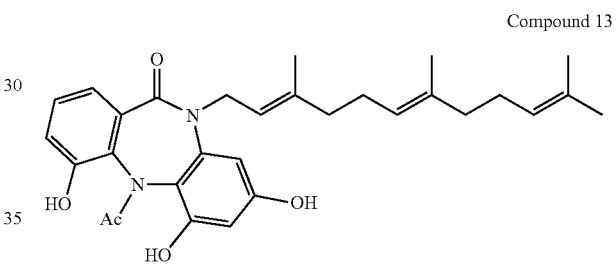

To a solution of Compound 1 dissolved in tetrahydrofuran (THF) is added 1.2 equivalents of acetyl chloride and a few drops of pyridine. The reaction mixture is allowed to stand at room temperature for 1-2 hours and then evaporated to dryness under reduced pressure to obtain a crude mixture containing Compound 13. Compound 13 is purified using HPLC or preparative TLC plates and the procedure described in any one of Examples 2, and 4-9.

e) Peracetylation:

Syntheses of Compound 15 by peracetylation of Compound 1.

Compound 15

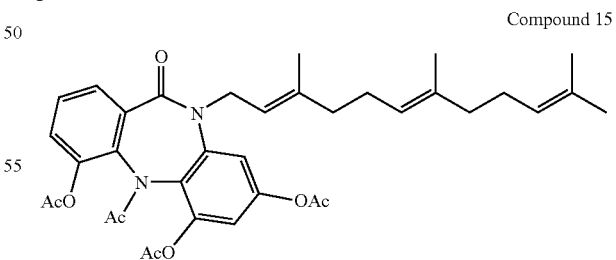

A solution of Compound 1 (100 mg) in acetic anhydride (5 ml) is treated with pyridine (250 µl). The reaction mixture is allowed to stand overnight at room temperature and is then diluted with toluene (100 ml). The toluene solution is washed well with aqueous 5% sodium bicarbonate solutions, then with water and is finally concentrated under reduced pressure to give an essentially pure sample of Compound 15 in almost quantitative yield.

f) Epoxidations:

The epoxide compounds of the present invention (e.g., compounds according to exemplary Compounds 16-22 are made from Compound 1, and Compounds 23 to 34 from the appropriate starting material, by treatment with any of a number of epoxidizing reagents such as perbenzoic acid, monoperphthalic acid or more preferably by m-chloroperbenzoic acid in an inert solvent such as tetrahydrofuran. It will be appreciated by one of ordinary skill in the art that slightly greater than one molecule equivalent of epoxidizing agent will result in the maximal yield of mono-epoxides, and that the reagent, solvent, concentration and temperature of the reaction will dictate the ratio of specific mono-epoxides formed. It will also be appreciated that the mono-epoxides will be enantiomeric mixtures, and that the di-epoxides and the tri-epoxide can be prepared as diastereomers and that the conditions of the reaction will determine the ratios of the products. One skilled in the art will appreciate that under most conditions of reactions the product will be a mixture of all possible epoxides and that these may be separated by standard methods of chromatography. Exemplary approaches to the generation of mono-, di-, and tri-epoxides are provided below.

1) Mono-epoxides Compounds, 16, 17 and 18 prepared by epoxidation of Compound 1 (as also shown in Example 8(c)):

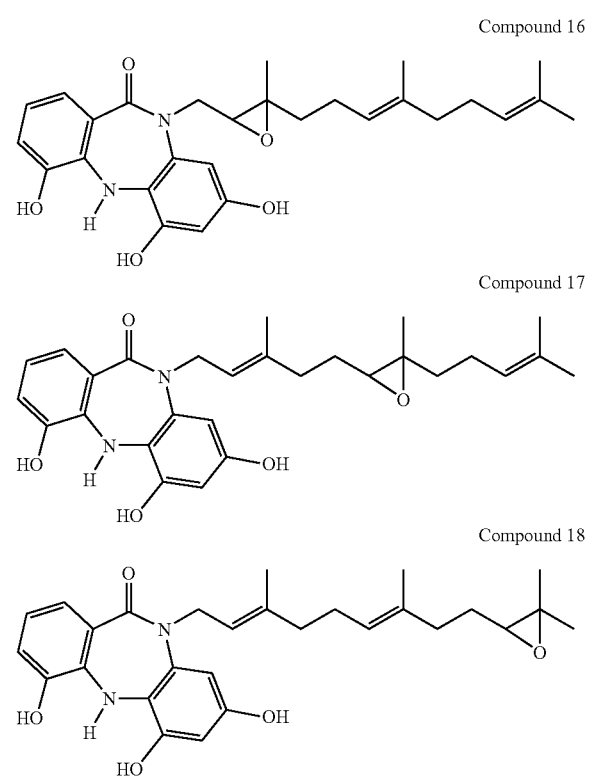

To a solution of Compound 1 dissolved in tetrahydrofuran (THF) is added 1.1 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex™ LH-20 to isolate a mixture of predominantly Compounds 16, 17 and 18, contaminated with some unchanged starting material and some di- and tri-epoxides. Compounds 16, 17 and 18 are separated and purified by HPLC using the system described in Examples 2 and 4-9. In a typical experiment yields of 15% to 25% are obtained for each of Compounds 16, 17 and 18.

2) Synthesis of Compounds 19, 20 and 21 by Di-Epoxidation of Compound 1:

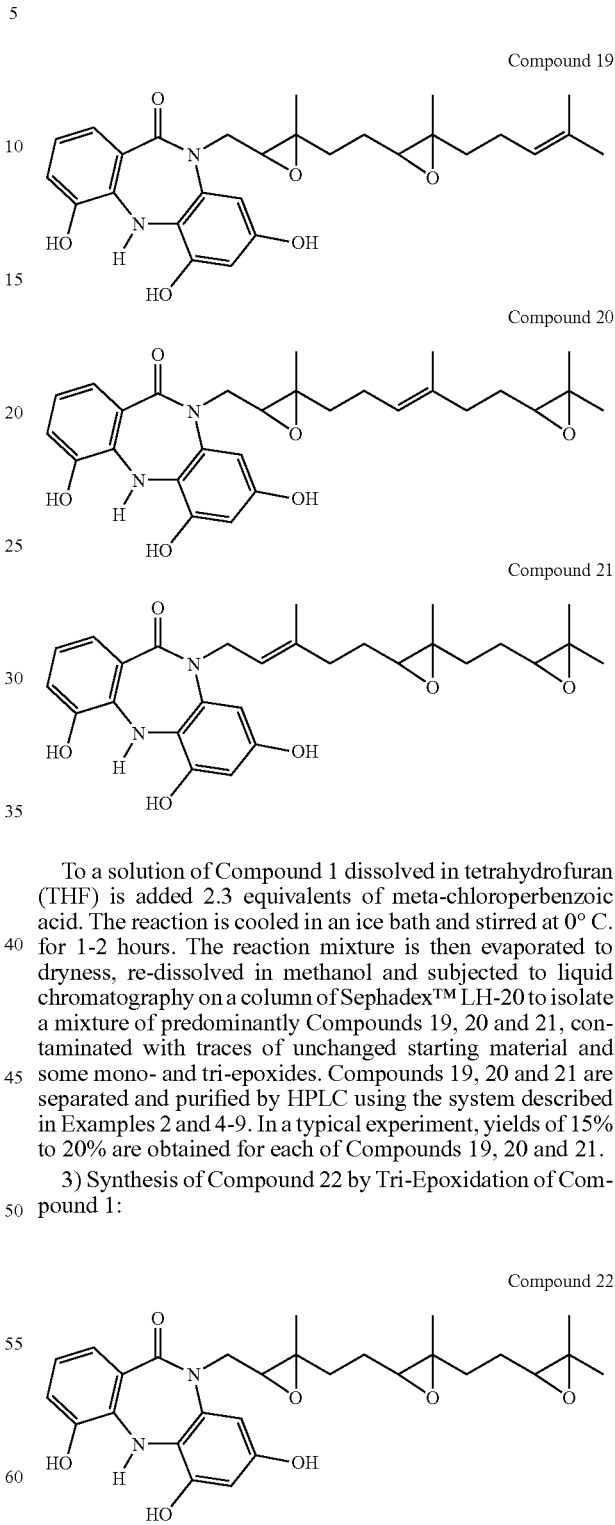

To a solution of Compound 1 dissolved in tetrahydrofuran (THF) is added 2.3 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex™ LH-20 to isolate a mixture of predominantly Compounds 19, 20 and 21, contaminated with traces of unchanged starting material and some mono- and tri-epoxides. Compounds 19, 20 and 21 are separated and purified by HPLC using the system described in Examples 2 and 4-9. In a typical experiment, yields of 15% to 20% are obtained for each of Compounds 19, 20 and 21.

3) Synthesis of Compound 22 by Tri-Epoxidation of Compound 1:

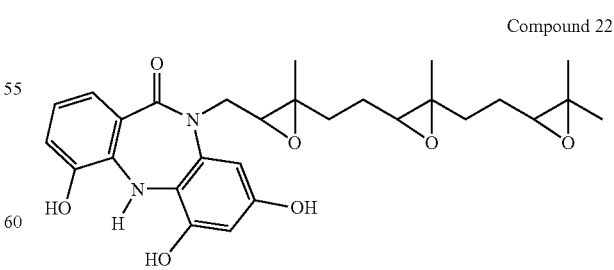

To a solution of Compound 1, dissolved in tetrahydrofuran (THF), is added 3.5 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex™ LH-20 to isolate Compound 22 in an essentially pure form in a yield of 80+%.

4) Syntheses of Compounds 23 and 24 by Epoxidation of Compound 42.

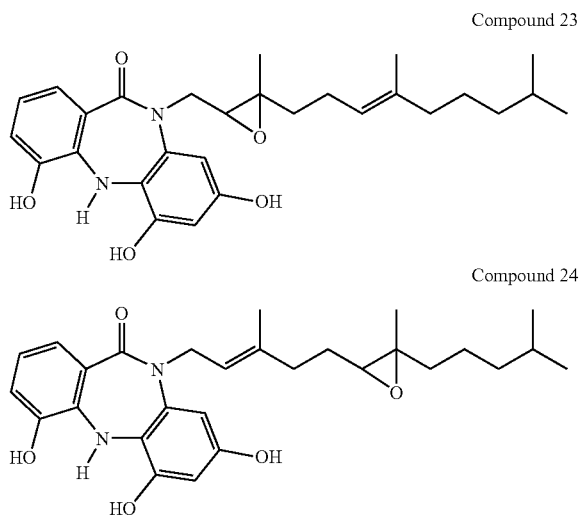

Compound 23

Compound 24

To a solution of Compound 42 dissolved in tetrahydrofuran (THF) is added 1.1 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid chromatography on a column of Sephadex™ LH-20 to isolate a mixture of predominantly Compounds 23 and 24, contaminated with some unchanged starting material and some diepoxide. Compounds 23 and 24 are separated and purified by HPLC or HSCC using one of the systems described in Examples 2 and 4-9. In a typical experiment yields of 35% to 40% are obtained for each of Compounds 23 and 24.

Compounds 25 and 29 to 34 are prepared using this procedure. In each procedure, Compound 42 is replaced by the appropriate starting material. More specifically, Compounds 25 and 29 are prepared using Compound 41 as starting material; Compounds 30 and 31 are prepared using Compound 40 as starting material; and Compounds 32, 33, and 34 are prepared respectively from Compounds 45, 44 and 43.

5) Synthesis of Compound 28 by Epoxidation of Compound 40.

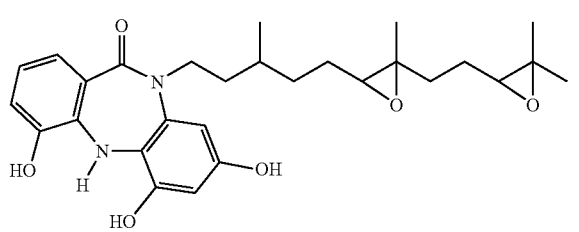

Compound 28 chromatography on a column of Sephadex™ LH-20 to isolate essentially pure Compound 28 in good yield.

Compounds 26 and 27 are prepared using the same procedure, but using respectively from Compounds 42 and 41 as starting material, instead of Compound 40.

g) Epoxide Opening:

Syntheses of Compound 53 by Opening the Epoxide of Compound 16.

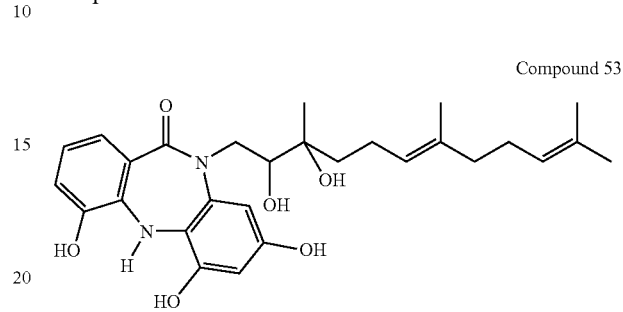

Compound 53

A solution of Compound 16 (100 mg) in tetrahydrofuran (50 ml) is treated with 1N aqueous hydrochloric acid (5 ml). The reaction mixture is stirred overnight at room temperature and is then diluted with toluene (100 ml) and water (200 ml). The toluene layer is separated and the aqueous layer is extracted with a further 100 ml of toluene. The combined toluene layers are washed once more with water (50 ml) and the separated and dried under vacuum to give the vicinal glycol Compound 53.

The same procedure is used to prepare Compounds 54 to 59, using respectively Compounds 17 to 22 as starting material.

h) Hydrogenation:

Compounds 40 to 46 (from Compound 1) and 78 (from Compound 2) are produced by catalytic hydrogenation using a source of hydrogen (hydrogen, formic acid, and the like), and a catalyst (palladium on charcoal, platinum oxide, Raney-Nickel, and the like). Hydrogen uptake is optionally measured or controlled.

1) Syntheses of Compounds 40, 41 and 42 by Hydrogenation of Compound 1.

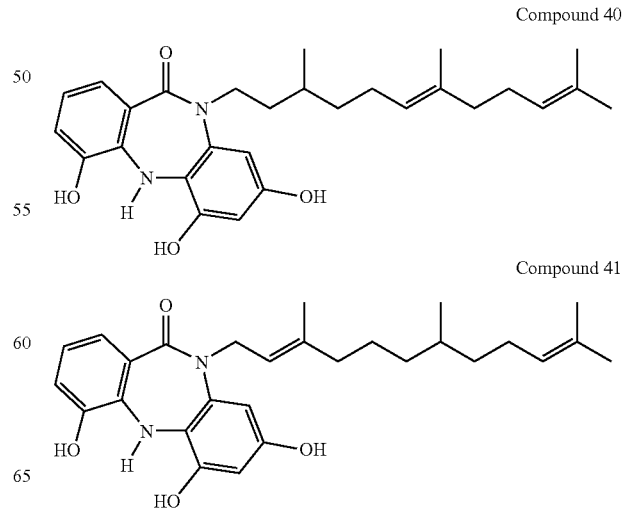

Compound 40

Compound 41

To a solution of Compound 40 dissolved in tetrahydrofuran (THF) is added 2.2 equivalents of meta-chloroperbenzoic acid. The reaction is cooled in an ice bath and stirred at 0° C. for 1-2 hours. The reaction mixture is then evaporated to dryness, re-dissolved in methanol and subjected to liquid Compound 42

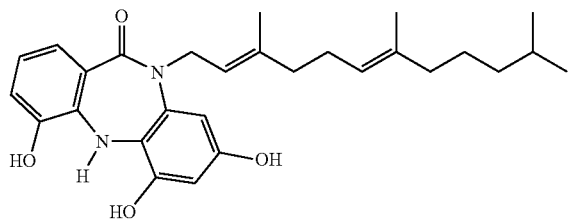

A solution Compound 1 (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where one millimole of hydrogen has been consumed, shaking is stopped, the vessel is rapidly evacuated and the atmosphere is replaced with nitrogen. The catalyst is removed by filtration and the filtrate is concentrated to obtain a crude mixture of Compounds 40, 41 and 42 contaminated by unreacted starting material and minor amounts of over reduced products. The desired products may be separated and purified by HPLC or HSCC chromatography using the systems as described in Examples 2 and 4-9 above, to obtain approximately 100 mg of each of Compounds 40, 41 and 42.

2) Syntheses of Compounds 43, 44 and 45 by Hydrogenation of Compound 1.

Compound 43

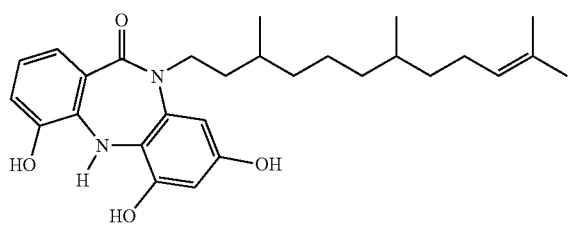

Compound 44

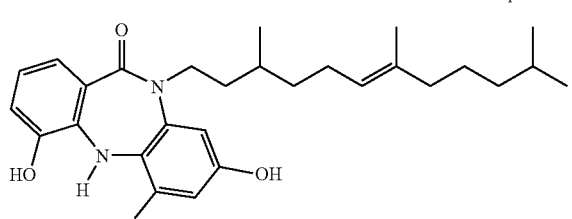

Compound 45

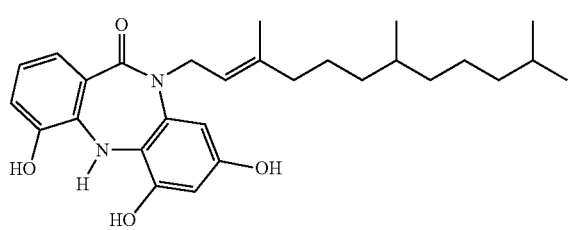

A solution of Compound 1 (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where two millimoles of hydrogen has been consumed, shaking is stopped, the vessel is rapidly evacuated and the atmosphere is replaced with nitrogen. The catalyst is removed by filtration and the filtrate is concentrated to obtain a crude mixture of Compounds 43, 44 and 45 contaminated by trace amounts unreacted starting material and minor amounts of under and over reduced products. The desired products may be separated and purified by HPLC or HSCC chromatography using the systems as described in Examples 2 and 4-9 above, to obtain approximately 100 mg of each of Compounds 43, 44 and 45.

3) Syntheses of Compound 46 by Hydrogenation of Compound 1 (Also Produced Using the Procedure of Example 8(a) and 8(b)).

Compound 46

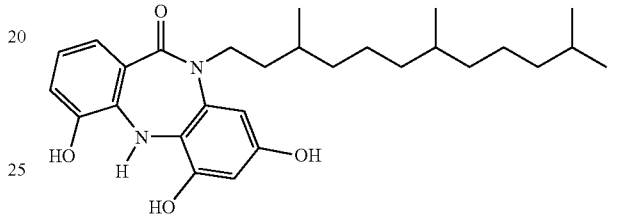

A solution of Compound 1 (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where three millimoles of hydrogen have been consumed, shaking is stopped, the vessel is rapidly evacuated and the atmosphere is replaced with nitrogen. The catalyst is removed by filtration and the filtrate is concentrated to obtain an essentially pure sample of Compound 46.

Compound 78 is prepared from the same procedure, using Compound 2 as starting material, instead of Compound 1.

i) Ozonolysis:

Syntheses of Compounds 47, 49 and 51 by Ozonolysis of Compound 1.

Compound 47

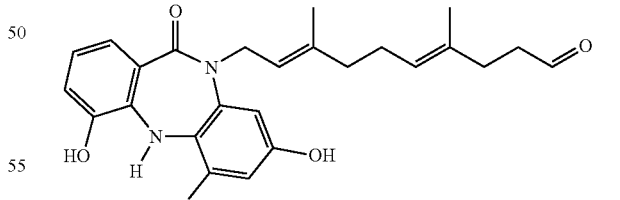

Compound 49

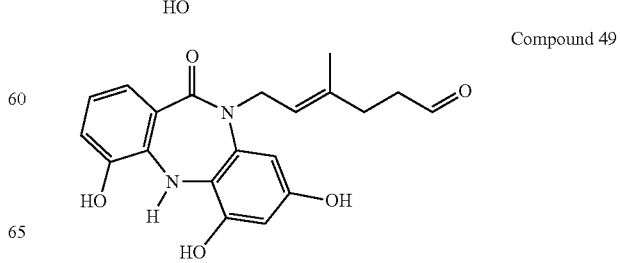

-continued

Compound 51

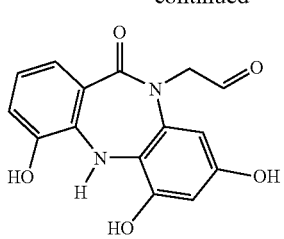

A solution of Compound 1 (462 mg) in dry ethyl acetate (200 ml) in an ozonolysis apparatus is cooled to below −20° C. A stream of ozone containing oxygen is passed into the solution from an ozone generator, which has been precalibrated such that the rate of ozone generation is known. To obtain predominantly Compound 47 the passage of ozone is halted after 0.9 millimole have been generated. To obtain predominantly Compound 49 the ozone passage is halted after 2 millimoles have been generated and to obtain Compound 51 as the predominant product 3.3 millimoles of ozone are generated.

At the completion of the ozonolysis, the reaction mixture is transferred to an hydrogenation apparatus, 5% palladium on calcium carbonate catalyst (0.2 g) is added to the reaction mixture which is maintained at less than −20° C. and is hydrogenated. When hydrogen uptake is complete the hydrogen atmosphere is replaced with nitrogen and the reaction mixture is allowed to come to room temperature, filtered to remove catalyst and the filtrate is concentrated. The crude product may be purified by chromatography using either HPLC or HSCC with the systems as described in Examples 2 and 4-9 to give, dependent on the amount of ozone used, Compounds 47, 49 and 51.

Dimethyl acetal compounds, for example, Compounds 94 to 96, are also produced by ozonolysis in methanol, followed by treatment with dimethyl sulfide. Aldehyde Compounds 47, 49 and 51, are obtained by hydrolysis (standard aqueous acidic conditions) of Compounds 94 to 96.

j) Reduction:

Synthesis of Compound 48 by Reduction of the Aldehyde of Compound 47.

Compound 48

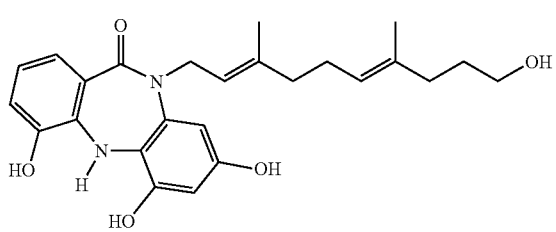

A solution of Compound 47 (50 mg) in isopropanol (5 ml) is cooled in an ice-salt bath and sodium borohydride (10 mg) is added and the mixture is stirred for 20 minutes. It is then diluted with water (20 ml) and extracted twice with toluene (10 ml portions) at ambient temperature. The combined toluene extracts are filtered and the filtrate is concentrated to give Compound 48.

Compounds 50 and 52 are produced by the same procedure, when replacing Compound 47 by Compounds 51 and 53 respectively as starting material.

k) Phosphorylation:

Compounds 114 to 120 and 124 to 130 are prepared according to the procedure described in Silverberg et al. (1996), *Tetreahedron Letters*, vol 37, 711-774. For example, Compounds 120 and 130 are produced as follows:

Compound 1 is treated, in carbon tetrachloride at −10° C., with 3.3 equivalents of dibenzylphosphite and N,N-diisopropylethylamine and a catalytic amount of 4-dimethylamino pyridine, and the reaction mixture stirred at this temperature for 1 hour or until disappearance of the starting material. The mixture is washed with water and the layers separated. The organic layer is dried and concentrated in vacuo. The residue obtained is further purified (as described in Examples 4-9) if necessary to give pure Compound 120.

Compound 120 is then hydrogenolyzed under standard conditions, such as hydrogen gas with wet palladium on carbon as catalyst, under controlled conditions.

Compounds 124 to 130 are also prepared using the above procedure but by using bis(2,2,2-trichloroethyl)phosphorochloridate, to produce bis(2,2,2-trichloroethyl)phosphate intermediates, which are cleaved using zinc dust and glacial acetic acid in pyridine as described in U.S. Pat. No. 5,561,122 (issued to Pettit et al) to produce the desired free mono-, bis- or triphosphate compound (i.e., Compound 124-130), depending on the excess of zinc used, and the time and temperature of reaction.

l) Biotinilation:

Compound 122 is prepared from Compound in three chemical steps: 1. epoxidation of Compound 1 (to produce Compound 18); 2. epoxide opening with HBr (to produce Compound 121); and 3, Reaction with Biotin (Aldrich). Step 1 is described in Example 8(d). Step 2 is accomplished as follows:

Compound 18 in tetrahydrofuran is treated at −10° C. with hydrobromic acid (1 eq) and stirred at this temperature for 1 hour or until completion by TLC. The reaction is diluted with water and neutralized with sodium bicarbonate. The mixture is extracted with ethyl acetate, dried and concentrated in vacuo. The residue is optionally purified as described in Examples 4 to 9 to give pure Compound 121.

Step 3 is accomplished as follows:

Compound 121, Biotin (1 eq) and HOBt (1-hydroxybenzotriazole hydrate, 1 eq) are dissolved in tetrahydrofuran and cooled to 0° C., DCC (dicyclohexylcarbodiimide, 1 eq) is added and the reaction mixture stirred for 1 hour or until completion. The reaction mixture is filtered to eliminate the produced DCU (dicyclohexylurea). The filtrate is concentrated in vacuo, and the residue is purified as described in Examples 4 to 9 to give pure Compound 122.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:
1. A compound selected from the group consisting of Compounds 131 to 161, or a pharmaceutically acceptable salt thereof:
Compound 131
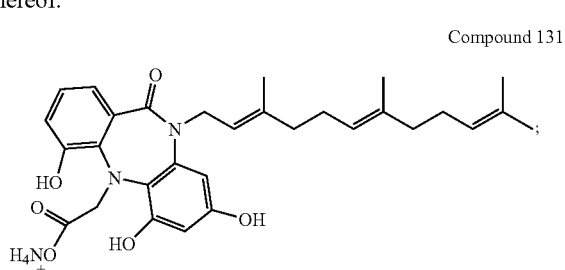
Compound 132
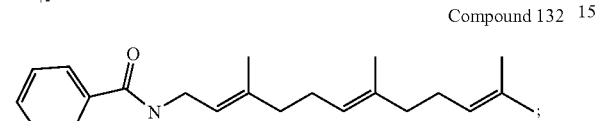
Compound 133
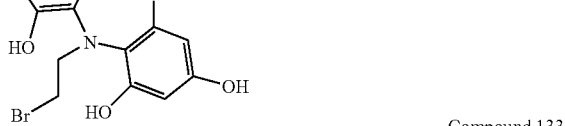
Compound 134
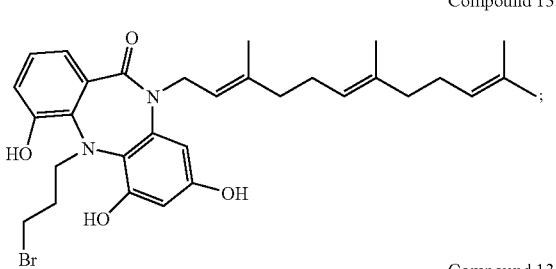
Compound 135
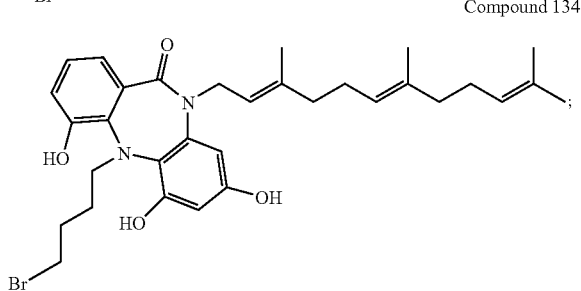
Compound 136
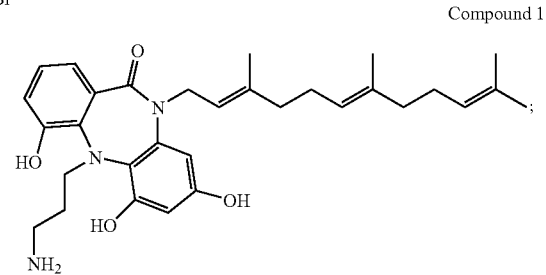
-continued
Compound 137
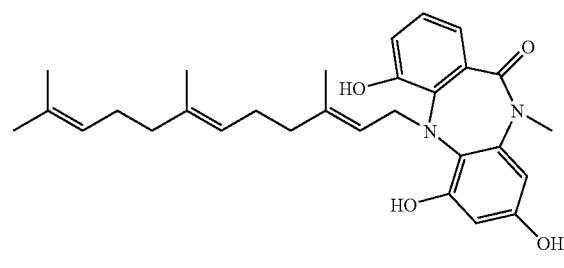
Compound 138
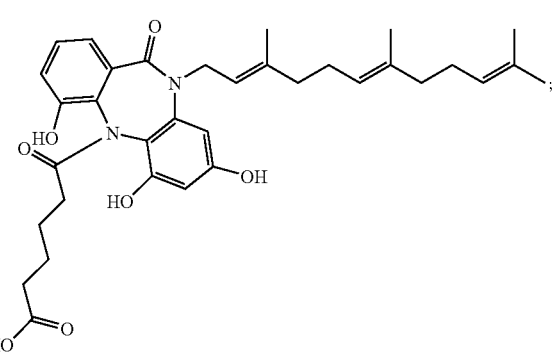
Compound 139
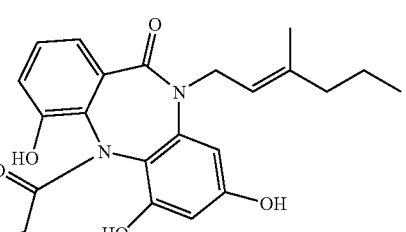
Compound 140
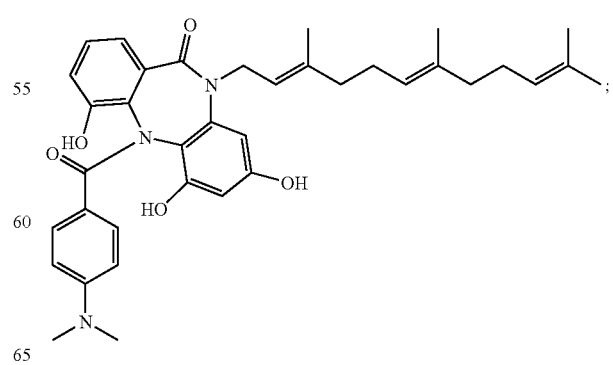

-continued
Compound 141
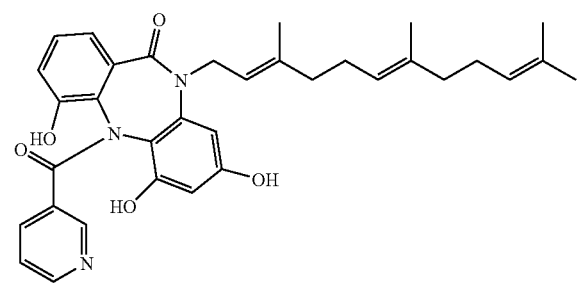
Compound 142
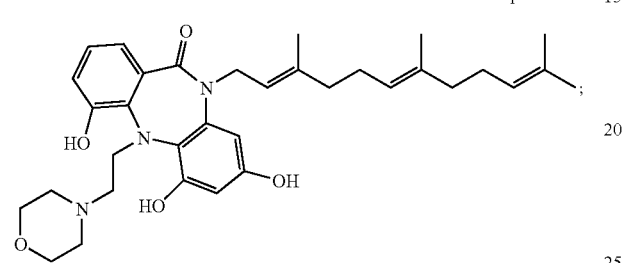
Compound 143
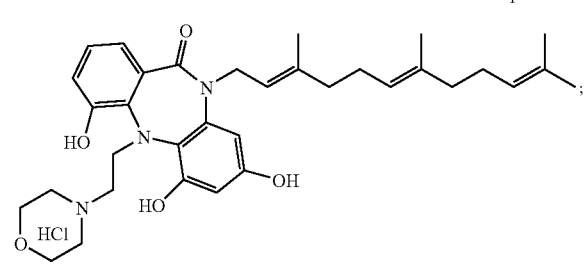
Compound 144
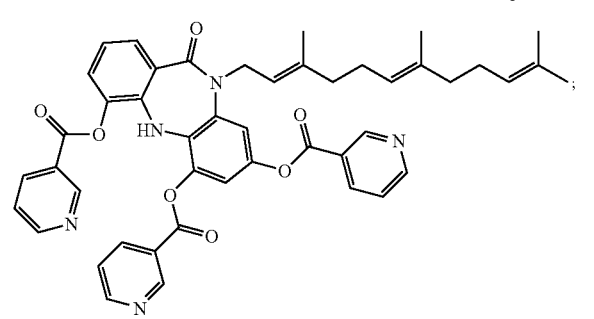
Compound 145
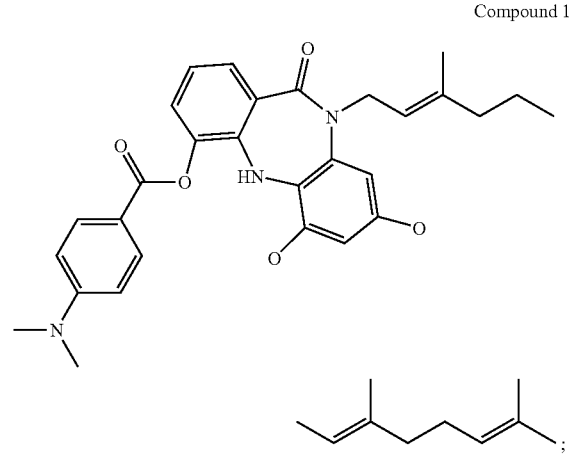
-continued
Compound 146
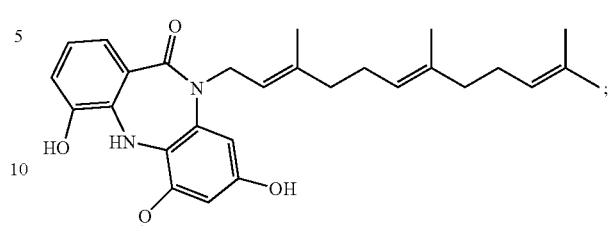
Compound 147
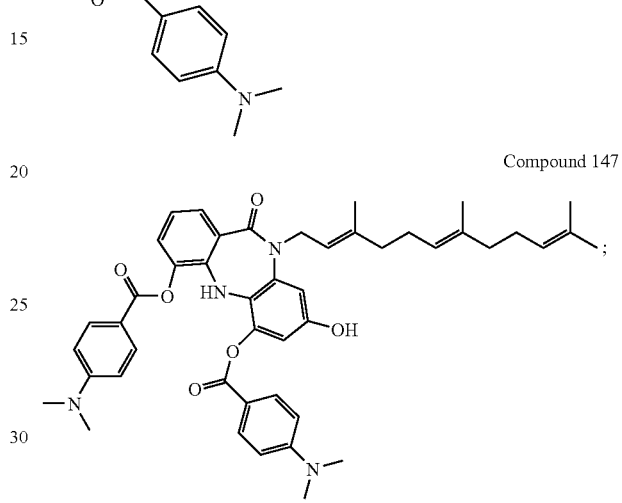
Compound 148
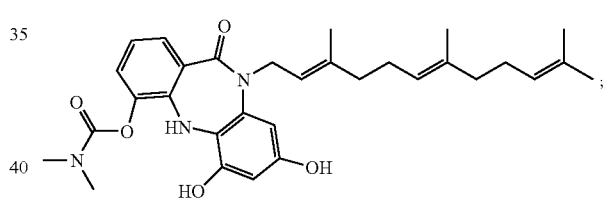
Compound 149
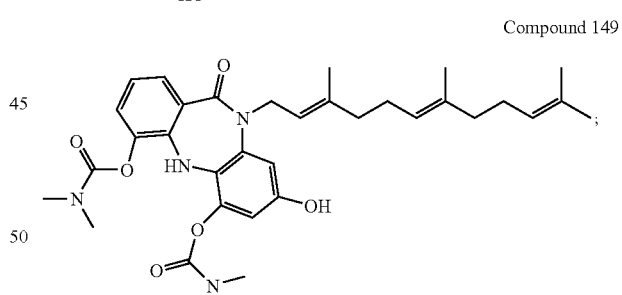
Compound 150
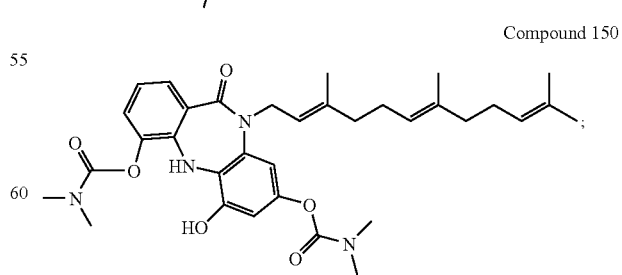

Compound 151
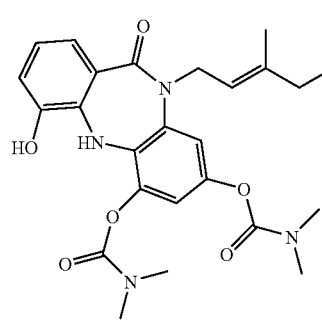
Compound 152
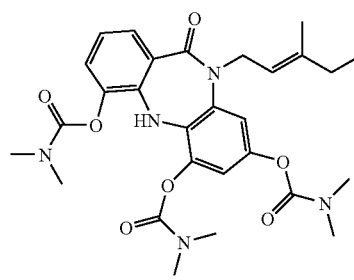
Compound 153
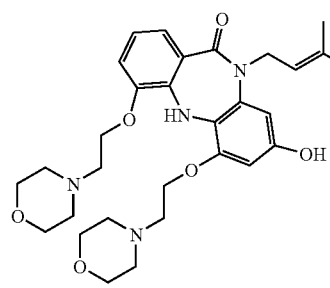
Compound 154
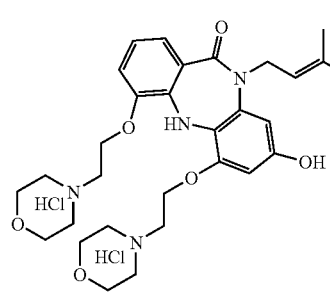
Compound 155
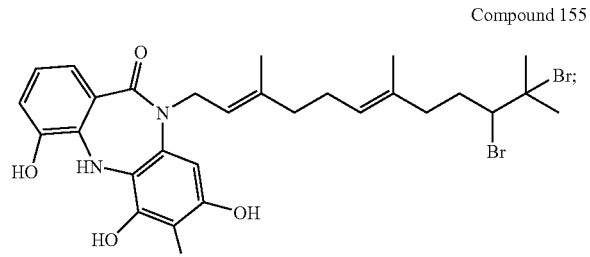
Compound 156
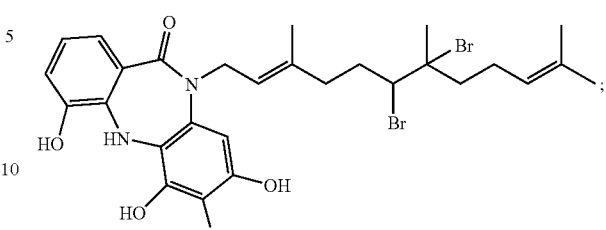
Compound 157
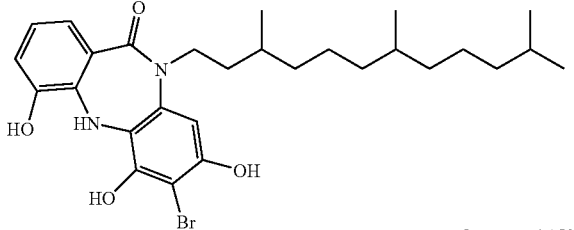
Compound 158
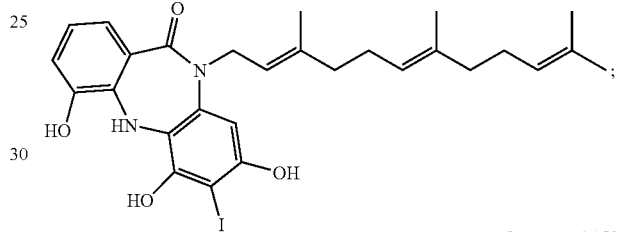
Compound 159
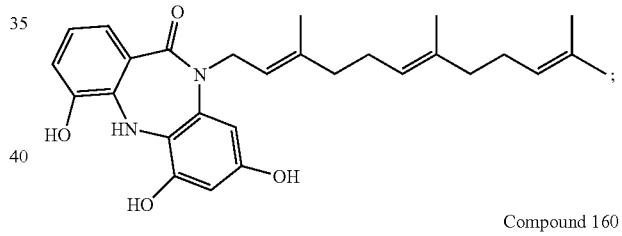
Compound 160
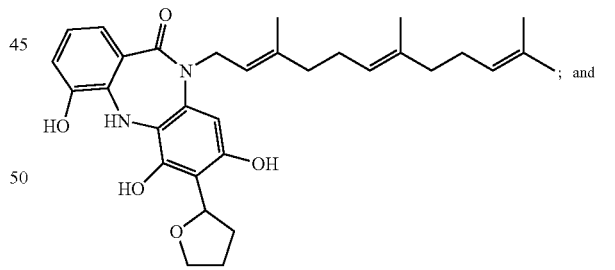
; and
Compound 161
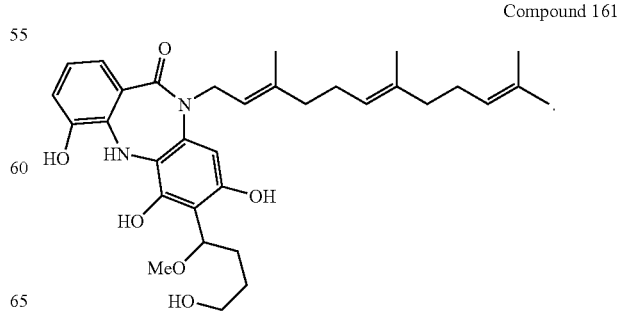

2. The compound of claim 1, wherein said compound is selected from the group consisting of Compounds 131, 132, 133, 134, 135, 136, 137, 138, 139, 140, 141, 142 and 143, or a pharmaceutically acceptable salt thereof.

3. The compound of claim 1, wherein said compound is selected from the group consisting of Compounds 144, 145, 146, 147, 148, 149, 150, 151, 152, 153 and 154, or a pharmaceutically acceptable salt thereof.

4. The compound of claim 1, wherein said compound is selected from the group consisting of Compounds 155, 156, 157 and 158, or a pharmaceutically acceptable salt thereof.

5. The compound of claim 1, wherein said compound is selected from the group consisting of Compounds 159, 160 and 161, or a pharmaceutically acceptable salt thereof.

6. A process for producing a compound of claim 1, said process comprising chemically modifying Compound 1:

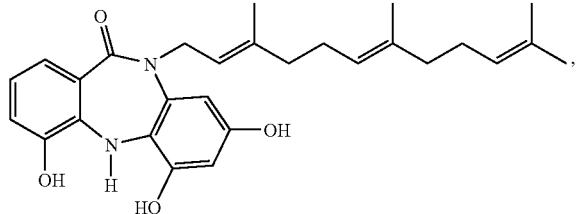

wherein said chemical modification comprises at least one step selected from the group consisting of: N-alkylations, N-acylations, O-alkylations, O-acylations, aromatic halogenation, farnesyl hydrogenation, farnesyl epoxidation, farnesyl dihydroxylation, farnesyl hydration, farnesyl hydroalkoxylation, farnesyl hydroamidation, and farnesyl ozonolysis.

7. The process of claim 6, wherein said chemical modification comprises at least one step selected from the group consisting of: N-alkylations, O-acylations, farnesyl hydrogenation, and farnesyl hydroalkoxylation.

8. A pharmaceutical composition comprising a compound of claim 1 and a pharmaceutically acceptable carrier.

9. A pharmaceutical composition comprising a compound of claim 2 and a pharmaceutically acceptable carrier.

10. A pharmaceutical composition comprising a compound of claim 3 and a pharmaceutically acceptable carrier.

11. A pharmaceutical composition comprising a compound of claim 4 and a pharmaceutically acceptable carrier.

12. A pharmaceutical composition comprising a compound of claim 5 and a pharmaceutically acceptable carrier.

* * * * *